(12) United States Patent
Ma et al.

(10) Patent No.: US 6,998,390 B2
(45) Date of Patent: Feb. 14, 2006

(54) OXOLIDE ANTIBACTERIALS

(76) Inventors: Zhenkun Ma, 7215 Marquette St., Dallas, TX (US) 75225; Stevan Djuric, 621 Paddock La., Libertyville, IL (US) 60048; Alan S. Florjancic, 4007 13th Pl., Kenosha, WI (US) 53144; Hong Yong, 312 Cambridge Dr., Grayslake, IL (US) 60030

(*) Notice: Subject to any disclaimer, the term of this patent is extended or adjusted under 35 U.S.C. 154(b) by 0 days.

(21) Appl. No.: 10/420,390

(22) Filed: Apr. 22, 2003

(65) Prior Publication Data
US 2004/0014688 A1   Jan. 22, 2004

Related U.S. Application Data

(60) Provisional application No. 60/375,373, filed on Apr. 25, 2002.

(51) Int. Cl.
*A61K 31/70* (2006.01)
*C07H 17/09* (2006.01)

(52) U.S. Cl. .................. 514/29; 536/7.2; 536/7.3; 536/7.4

(58) Field of Classification Search ............ 536/7.2, 536/7.3, 7.4; 514/29
See application file for complete search history.

(56) References Cited

U.S. PATENT DOCUMENTS 5,439,890 A * 8/1995 Agouridas et al. ............ 514/29
6,124,269 A * 9/2000 Phan et al. .................... 514/29

* cited by examiner

*Primary Examiner*—Elli Peselev
(74) *Attorney, Agent, or Firm*—B. Gvegong Donner

(57) ABSTRACT

Antibacterial compounds having formula (I)

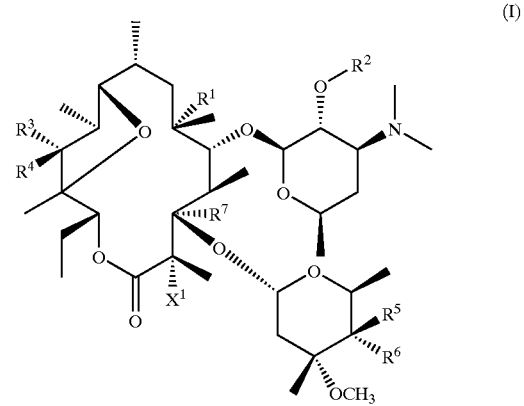

and formula (II)

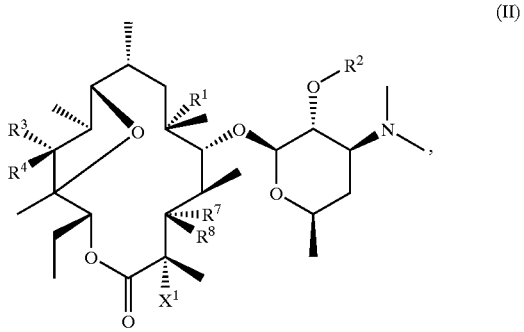

and salts, prodrugs, and salts of prodrugs thereof, processes for making the compounds and intermediates employed in the processes, compositions containing the compounds, and methods for prophylaxis or treatment of bacterial infections in a fish or a mammal using the compounds are disclosed.

18 Claims, No Drawings

OXOLIDE ANTIBACTERIALS

This application claims benefit of co-pending U.S. Provisional Application Ser. No. 60/375,373, filed Apr. 25, 2002, the specification of which is hereby incorporated by reference into this specification.

TECHNICAL FIELD

This invention is directed to compounds which are useful as antibacterials, processes for making the compounds and intermediates useful in the process, compositions containing the compounds, and methods for prophylaxis or treatment of bacterial infections using the compounds.

BACKGROUND OF THE INVENTION

Because the effectiveness of many drugs currently available for prophylaxis or treatment of bacterial infections is being compromised by the emergence of drug-resistant bacteria, novel antibacterials would be beneficial for their therapeutic value and their contribution to the antibacterial arts.

SUMMARY OF THE INVENTION

A first embodiment of this invention, therefore, is directed to compounds which are useful as antibacterials, and salts, prodrugs, and salts of prodrugs thereof, the compounds having formula (I)

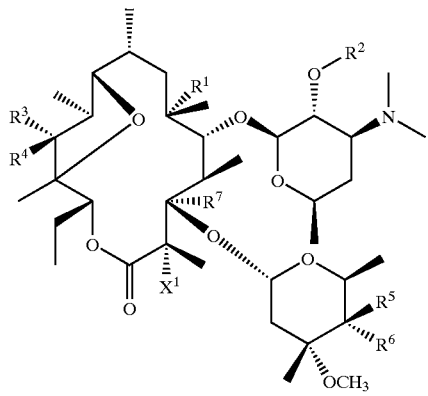

(I)

or formula (II)

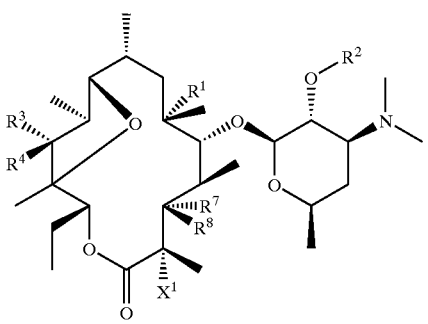

(II)

in which
$R^1$ is hydrogen, —OH, —$OR^9$, —OC(O)$OR^9$, —OC(O)$NH_2$, —OC(O)$NHR^{10}$, —OC(O)$NR^{10}R^{11}$, —$OCH_2R^{12}$, —OC(O)$OCH_2R^{12}$, —OC(O)$NHCH_2R^{12}$, or —OC(O)N($CH_2R^{12}$)$_2$;

$R^2$ is hydrogen or $R^P$, in which $R^P$ is a hydroxyl protecting moiety;

one of $R^3$ and $R^4$ is hydrogen, and the other is —OH, —$OR^{13}$, —OC(O)$OR^{13}$, —$NH_2$, —NHC(O)$OR^{14}$, —$NHR^{15}$, —$NR^{15}R^{16}$, —OC(O)$NH_2$, —OC(O)$NHR^{15}$, —OC(O)$NR^{15}R^{16}$, —N($R^{17}$)C(O)$NH_2$, —($R^{17}$)C(O)$NHR^{15}$, —N($R^{17}$)C(O)$NR^{15}R^{16}$, —$OCH_2R^{18}$, —$NHCH_2R^{18}$, —N($CH_2R^{18}$)$_2$, —OC(O)$OCH_2R^{18}$, —OC(O)$NHCH_2R^{18}$, —OC(O)N($CH_2R^{18}$)$_2$, —N($R^{17}$)C(O)$NHCH_2R^{18}$, or —N($R^{17}$)C(O)N($CH_2R^{18}$)$_2$; or
$R^3$ and $R^4$ together are =O or =$NOR^{19}$;

one of $R^5$ and $R^6$ is hydrogen, and the other is —OH, —$OR^{20}$, —OC(O)$OR^{20}$, —$NH_2$, —NHC(O)$OR^{14}$, —$NHR^{21}$, —$NR^{21}R^{22}$, —OC(O)$NH_2$, —OC(O)$NHR^{21}$, —OC(O)$NR^{21}NR^{22}$, —N($R^{23}$)C(O)$NH_2$, —N($R^{23}$)C(O)$NHR^{21}$, —N($R^{23}$)C(O)$NR^{21}R^{22}$, —$OCH_2R^{24}$, —$NHCH_2R^{24}$, —N($CH_2R^{24}$)$_2$, —OC(O)$OCH_2R^{24}$, —OC(O)$NHCH_2R^{24}$, —OC(O)N($CH_2R^{24}$)$_2$, —N($R^{23}$)C(O)$NHCH_2R^{24}$, or —N($R^{23}$)C(O)N($CH_2R^{24}$)$_2$; or
$R^5$ and $R^6$ together are =O;

$R^7$ is hydrogen and $R^8$ is —OH, —$OR^{25}$, —OC(O)$R^{25}$, —OC(O)$OR^{25}$, —OC(O)$NH_2$, —OC(O)$NHR^{26}$, —OC(O)$NR^{26}R^{27}$, —$OCH_2R^{28}$, or —OC(O)$OCH_2R^{28}$; or
$R^7$ and $R^8$ together are =O;

$R^9$, $R^{13}$, $R^{19}$, $R^{20}$, and $R^{25}$ are independently alkyl, cycloalkyl, —($CH_2$)alkenyl, —($CH_2$)alkynyl, alkyl substituted with one substituent selected from the group consisting of cycloalkyl, aryl, heteroaryl, and heterocyclyl, —($CH_2$)alkenyl substituted with one substituent selected from the group consisting of cycloalkyl, aryl, heteroaryl, and heterocyclyl, or —($CH_2$)alkynyl substituted with one substituent selected from the group consisting of cycloalkyl, aryl, heteroaryl, and heterocyclyl;

$R^{10}$, $R^{11}$, $R^{15}$, $R^{16}$, $R^{21}$, $R^{22}$, $R^{26}$, and $R^{27}$ are independently alkyl, cycloalkyl, —($CH_2$)alkenyl, —($CH_2$)alkynyl, aryl, heteroaryl, heterocyclyl, alkyl substituted with one substituent selected from the group consisting of cycloalkyl, aryl, heteroaryl, heterocyclyl, —$NH_2$, —$NHR^{31}$, and —$NR^{31}R^{32}$, —($CH_2$)alkenyl substituted with one substituent selected from the group consisting of cycloalkyl, aryl, heteroaryl, heterocyclyl, —$NH_2$, —$NHR^{31}$, and —$NR^{31}R^{32}$, or —($CH_2$)alkynyl substituted with one substituent selected from the group consisting of cycloalkyl, aryl, heteroaryl, heterocyclyl, —$NH_2$, —$NHR^{31}$, and —$NR^{31}R^{32}$; or $R^{10}$ and $R^{11}$ together, $R^{15}$ and $R^{16}$ together, $R^{21}$ and $R^{22}$ together, or $R^{26}$ and $R^{27}$ together are independently $C_3$–$C_6$-alkylene, $C_5$–$C_6$-alkylene interrupted with one moiety selected from the group consisting of —O—, —NH—, —N(alkyl)-, —S—, —S(O)—, and —$SO_2$—, $C_3$–$C_6$-alkylene substituted with one substituent selected from the group consisting of —OH, —O(alkyl), =O, —$NH_2$, —NH(alkyl), and —N(alkyl)$_2$, or $C_5$–$C_6$-alkylene interrupted with one moiety selected from the group consisting of —O—, —NH—, —N(alkyl)-, —S—, —S(O)—, and —$SO_2$— and substituted with one substituent selected from the group consisting of —OH, —O(alkyl), =O, —$NH_2$, —NH(alkyl), and —N(alkyl)$_2$;

$R^{12}$, $R^{18}$, $R^{24}$, and $R^{28}$ are independently alkyl interrupted with one, two, or three moieties independently selected from the group consisting of —O—, —NH—, —N(alkyl)-, —S—, —S(O)—, and —$SO_2$— or alkyl interrupted with one, two, or three moieties independently selected from the group consisting of —O—, —NH—, —N(alkyl)-, —S—, —S(O)—, and —SO$_2$— and substituted with one, two, or three substituents independently selected from the group consisting of cycloalkyl, halo, aryl, heteroaryl, heterocyclyl —OH, =O, —O(alkyl), —NH$_2$, —NH(alkyl), and —N(alkyl)$_2$;

$R^{14}$ is alkyl or alkyl substituted with one or two independently selected aryl substituents;

$R^{17}$ and $R^{23}$ are independently hydrogen or alkyl;

$R^{31}$ and $R^{32}$ are independently alkyl, cycloalkyl, aryl, heteroaryl, heterocyclyl, —(CH$_2$)alkenyl, —(CH$_2$)alkynyl, alkyl substituted with one substituent selected from the group consisting of cycloalkyl, aryl, heteroaryl, heterocyclyl, —NH$_2$, —NH(alkyl), and —N(alkyl)$_2$, —(CH$_2$)alkenyl substituted with one substituent selected from the group consisting of cycloalkyl, aryl, heteroaryl, heterocyclyl, —NH$_2$, —NH(alkyl), and —N(alkyl)$_2$, or —(CH$_2$)alkynyl substituted with one substituent selected from the group consisting of cycloalkyl, aryl, heteroaryl, heterocyclyl, —NH$_2$, —NH(alkyl), and —N(alkyl)$_2$; or $R^{31}$ and $R^{32}$ together are $C_3$–$C_6$-alkylene, $C_5$–$C_6$-alkylene interrupted with one moiety selected from the group consisting of —O—, —NH—, —N(alkyl)-, —S—, —S(O)—, and —SO$_2$—, $C_3$–$C_6$-alkylene substituted with one substituent selected from the group consisting of —OH, —O(alkyl), =O, —NH$_2$, —NH(alkyl), and —N(alkyl)$_2$, or $C_5$–$C_6$-alkylene interrupted with one moiety selected from the group consisting of —O—, —NH—, —N(alkyl)-, —S—, —S(O)—, and —SO$_2$— and substituted with one substituent selected from the group consisting of —OH, —O(alkyl), =O, —NH$_2$, —NH(alkyl), and —N(alkyl)$_2$; and $X^1$ is hydrogen, fluoride, chloride, or bromide.

A second embodiment of this invention is directed to the compounds of the first embodiment, and the salts, prodrugs, and salts of the prodrugs thereof, having the stereochemistry shown in the compounds having formula (I)-f,

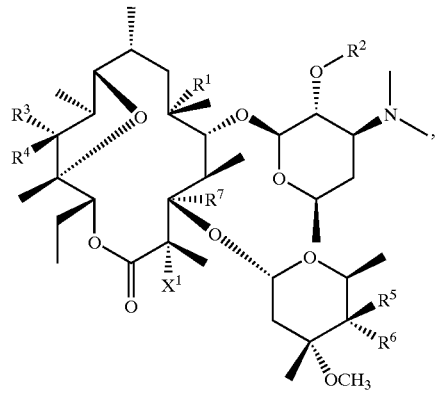

formula (I)-f,

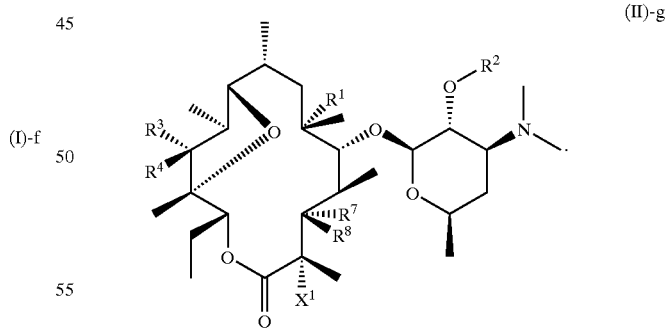

formula (I)-g,

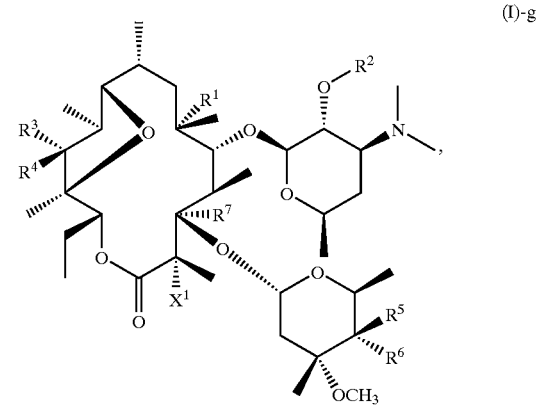

formula (II)-f,

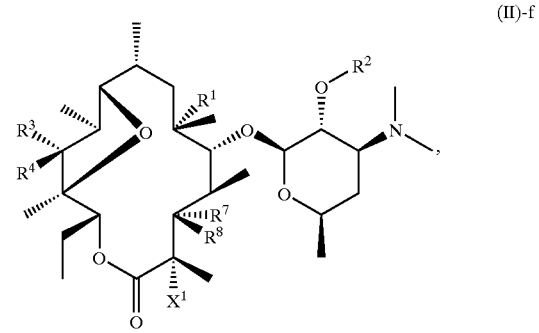

or formula (II)-g,

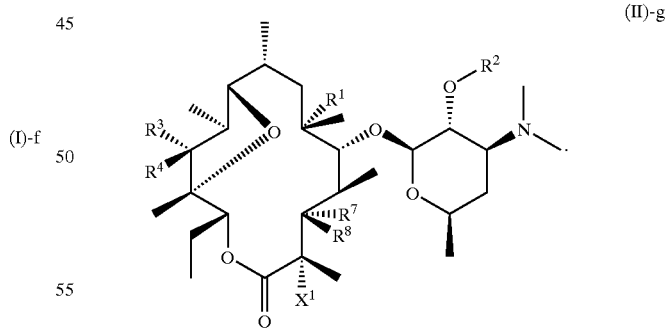

A third embodiment of this invention is directed to a process for making the compounds of the first and second embodiments.

A fourth embodiment of this invention is directed to intermediates which are useful in the second embodiment.

A fifth embodiment of this invention is directed to compositions for the prophylaxis or treatment of bacterial infections in a fish or a mammal, the compositions comprising a therapeutically effective amount of one or more of the compounds of the first or second embodiment and an excipient.

A sixth embodiment of this invention is directed to methods for prophylaxis or treatment of bacterial infections in a fish or a mammal comprising administering to the fish or the mammal a therapeutically effective amount of one or more of the compounds of the first or second embodiment.

DETAILED DESCRIPTION OF THE INVENTION

Compounds of this invention, also referred to as "the compounds," comprise of both fixed and variable moieties, which variable moieties are identified by a capital letter and accompanying numerical or alphabetical superscript, and for which the following terms have the meanings indicated.

"Alkenyl" means monovalent, straight-chain and branched-chain hydrocarbon moieties, having two to eight carbon atoms and at least one carbon-carbon double bond. Alkenyl moieties include but-1,3-dienyl, butenyl, but-2-enyl, ethenyl, 1-ethylhexen-2-yl, hex-3-enyl, 1-methylbutenyl, 2-methylbutenyl, 1-methylbut-2-enyl, 1-methylbut-1,3-dienyl, pentenyl, pent-2-enyl, pent-3-enyl, and propenyl.

"Alkyl" means monovalent, saturated, straight-chain and branched-chain hydrocarbon moieties, having one to six carbon atoms. Alkyl moieties include butyl, 1,1,-dimethylethyl (tert-butyl), 1,1-dimethylpropyl, 1,2-dimethylpropyl, ethyl, 1-ethylpropyl, 2-ethylpropyl, hexyl, methyl, 2-methylpropyl, 3-methylbutyl, 1-methylpentyl, 2-methylpent-3-yl, and pentyl.

"Alkylene" means divalent, saturated, straight-chain and branched-chain hydrocarbon moieties, having one to eight carbon atoms. Alkylene moieties include butylene, 1,1,-dimethylethylene, 1,1-dimethylpropylene, 1,2-dimethylpropylene, ethylene, 1-ethylpropylene, 2-ethylpropylene, hexylene, methylene, 2-methylpropylene, 3-methylbutylene, 1-methylpentylene, 2-methylpent-3-ylene, and pentylene.

"Alkynyl" means monovalent, straight-chain and branched-chain hydrocarbon moieties, having two to six carbon atoms and at least one carbon-carbon triple bond. Alkynyl moieties include ethynyl (acetylenyl), pentynyl, pent-2-ynyl, pent-3-ynyl, pent-4-ynyl, 1-methylbut-2-ynyl, 2-methylbut-3-ynyl, hexynyl, hex-2-ynyl, hex-3-ynyl, hex-4-ynyl, 1-methyl-pent-2-ynyl, 1-methylenepent-3-ynyl, 1-methyl-pent-2,4-diynyl, and prop-2-ynyl (propargyl).

"Aryl" means monovalent, unsubstituted or substituted phenyl which is unfused or fused with another phenyl moiety or a cycloalkyl, cycloalkenyl, heteroaryl, heterocyclyl, naphthyl, or saturated part of an indanyl moiety.

Phenyl moieties fused with phenyl, naphthyl, or the saturated part of an indanyl moieties are unsubstituted and substituted naphthyl, anthracen-(1- to 4-)yl, or fluoren-(1- to 4-)yl, respectively.

Phenyl moieties fused with cycloalkyl moieties are unsubstituted and substituted indan-(4- to 7-)yl and 1,2,3,4-tetrahydronaphth-(5- to 8-)yl.

Phenyl moieties fused with cycloalkenyl moieties are unsubstituted and substituted inden-(4- to 7-)yl, 1,2-dihydronaphth-(5- to 8-)yl and 1,2-dihydronaphth-(5- to 8-)yl.

Phenyl moieties fused with heteroaryl moieties include unsubstituted and substituted benzimidazol-(4- to 7-)yl, 1-benzofuran-(4- to 7-)yl, 1,2-benzisothiazol-(4- to 7-)yl, benzthiazol-(4- to 7-)yl, 1-benzothiophen-(4- to 7-)yl, cinnolin-(5- to 8-)yl, indol-(4- to 7-)yl, isoquinolin-(5- to 8-)yl, phthalazin-(5- to 8-)yl, quinazolin-(5- to 8-)yl, quinolin-(5- to 8-)yl, and quinoxalin-(5- to 8-)yl.

Phenyl moieties fused with heterocyclyl moieties include unsubstituted and substituted 1,3-benzodioxa(4- to 7-)yl, 1,4-benzodioxa(5- to 8-)yl, 1,3-dihydro-2-benzofuran-(4- to 7-)yl, 2,3-dihydro-1-benzofuran-(4- to 7-)yl, 1,3-dihydro-2-benzothiophen-(4- to 7-)yl, 2,3-dihydro-1-benzothiophen-(4- to 7-)yl, and indolin-(4- to 7-)yl.

"Cycloalkyl" means monovalent, unsubstituted and substituted, saturated cyclic hydrocarbon moieties, having three to six carbon atoms. Cycloalkyl moieties are unsubstituted and substituted cyclopropyl, cyclobutyl, cyclopentyl, and cyclohexyl.

"Cycloalkenyl" means means monovalent, unsubstituted and substituted, cyclic hydrocarbon moieties having four to six carbon atoms and at least one carbon-carbon double bond. Cycloalkenyl moieties are unsubstituted and substituted 1,3-cyclohexadienyl, 1,4-cyclohexadienyl, cyclohexenyl, cyclopentadienyl, and cyclopentenyl.

"Halo" means fluoro (—F), chloro (—Cl), bromo (—Br), and iodo (—I).

"Heteroaryl" means monovalent, aromatic, unsubstituted and substituted five-membered ring moieties having two double bonds and (a) one oxygen or one sulfur atom, (b) one, two, three, or four nitrogen atoms, or (c) one or two nitrogen atoms and one oxygen or one sulfur atom and the remaining atoms are carbon atoms, each of which is attached through a carbon atom or a nitrogen atom; and monovalent six-membered ring moieties having three double bonds and one, two, or three nitrogen atoms and the remaining atoms are carbon atoms, attached through a carbon atom; in which the foregoing heteroaryl moieties are unfused or fused with another heteroaryl moiety or an aryl moiety.

Five-membered heteroaryl moieties are unsubstituted and substituted furanyl, imidazolyl, isothiazolyl, isoxazolyl, 1,2,3-oxadiazolyl, oxazolyl, pyrazolyl, pyrrolyl, tetrazolyl, 1,3,4-thiadiazolyl, thiazolyl, thiophenyl (thienyl), 2H-tetraäzolyl, and 1,2,3-triazolyl.

Five-membered heteroaryl moieties fused with aryl moieties include unsubstituted and substituted benzimidazol-(1- or 2-)yl, 1-benzofuran-(2- to 3-)yl, 1,2-benzisothiazol-3-yl, benzthiazol-2-yl, 1-benzothiophen-(2- to 3-)yl, cinnolin-(3- or 4-)yl, indol-(1- to 3-)yl, isoquinolin-(1-, 3-, or 4-)yl, phthalazin-(1- or 4-)yl, quinazolin-(2- or 4-)yl, quinolin-(2- to 4-)yl, and quinoxalin-(2- or 3-)yl.

Five-membered heteroaryl moieties fused with other five-membered heteroaryl moieties include unsubstituted and substituted [1,3]thiazolo[4,5-d][1,3]oxazolyl, [1,3]thiazolo[4,5-d][1,3]thiazolyl, thieno[3,2-d][1,3]oxazolyl, thieno[3,2-d][1,3]thiazolyl, and thieno[2,3-b]thiophenyl.

Five-membered heteroaryl moieties fused with six-membered heteroaryl moieties include unsubstituted and substituted furo[2,3-b]pyridin-(2- or 3-)yl, 3H-imidazo[4,5-b]pyridin-(2- or 3-)yl, [1,3]thiazolo[4,5-b]pyrazin-2-yl, [1,3]thiazolo[4,5-b]pyridin-2-yl, and thieno[2,3-b]pyridin-(2- or 3-)yl.

Six-membered heteroaryl moieties are unsubstituted and substituted pyrazinyl, pyridazinyl, pyridyl, pyrimidinyl, and 1,3,5-triazinyl.

Six-membered heteroaryl moieties fused with aryl moieties include unsubstituted and substituted cinnolin-(3- or 4-)yl, isoquinolin-(1-, 3-, or 4-)yl, phthalazin-(1- or 4-)yl, quinazolin-(2- or 4-)yl, quinolin-(2- to 4-)yl, and quinoxalin-(2- or 3-)yl.

Six-membered heteroaryl moieties fused with five-membered heteroaryl moieties include unsubstituted and substituted furo[2,3-b]pyridin-(4- to 6-)yl, 3H-imidazo[4,5-b]pyridin-(5- to 7-)yl, [1,3]thiazolo[4,5-b]pyrazin-(5- or 6-)yl, [1,3]thiazolo[4,5-b]pyridin-(5- to 7-)yl, and thieno[2,3-b]pyridin-(4- to 6-)yl.

Six-membered heteroaryl moieties fused with other six-membered heteroaryl moieties include unsubstituted and substituted 1,5-naphthyridinyl, 1,7-naphthyridinyl, 1,8-naphthyridinyl, pteridinyl, pyridazino[4,5-d]pyridazinyl, pyrido[2,3-d]pyridazinyl, and pyrido[3,4-d]pyridazinyl.

"Heterocyclyl" means (a) monovalent, non-aromatic, unsubstituted and substituted four-membered ring moieties having one nitrogen, oxygen, or sulfur atom and the remaining atoms are carbon atoms, zero double bonds, attached through a carbon atom or a nitrogen atom, (b) monovalent, non-aromatic, unsubstituted and substituted five-membered ring moieties having one or two nitrogen, oxygen, or sulfur atoms and the remaining atoms are carbon atoms, and zero or one double bonds, attached through a carbon atom or a nitrogen atom, and (c) monovalent, non-aromatic, unsubstituted and substituted six-membered ring moieties having one, two, or three nitrogen, oxygen, or sulfur atoms and the remaining atoms are carbon atoms, and zero, one, or two double bonds, attached through a carbon atom or a nitrogen atom.

Four-membered heterocyclyl moieties are unsubstituted and substituted oxetane, thietane, and azetidine.

Five-membered heterocyclyl moieties include unsubstituted and substituted 1,4-dioxanyl, 1,3-dioxolanyl, imidazolidinyl, 2-imidazolinyl, 4,5-dihydroisoxazolyl, pyrazolidinyl, 2-pyrazolinyl, pyrrolidinyl, 2-pyrrolinyl, 3-pyrrolinyl, and 2H-pyrrolyl.

Six-membered heterocyclyl moieties include unsubstituted and substituted 1,3-dithianyl, 1,4-dithianyl, morpholinyl, piperidinyl, piperazinyl, pyranyl, 2H-pyranyl, 4H-pyranyl, and thiomorpholinyl.

Substituted aryl and heteroaryl moieties are those moieties substituted with one, two, three, four, or five substituents independently selected from the group consisting of alkyl, alkenyl, alkynyl, cycloalkyl, halo, —CN, —OH, —SH, —NH$_2$, —NO$_2$, —CF$_3$, —CH$_2$CF$_3$, —CF$_2$CF$_3$, —OCF$_3$, —OCH$_2$CF$_3$, —OCF$_2$CF$_3$, —OR$^{30}$, —SR$^{30}$, —S(O)(alkyl), —SO$_2$(alkyl), —C(O)H, —C(O)(alkyl), —C(O)OH, —C(O)O(alkyl), —NH(alkyl), —N(alkyl)$_2$, —C(O)NH$_2$, —C(O)NH(alkyl), —C(O)N(alkyl)$_2$, —OC(O)(alkyl), —OC(O)O(alkyl), —OC(O)NH$_2$, —OC(O)NH(alkyl), —OC(O)N(alkyl)$_2$, —NHC(O)H, —NHC(O)(alkyl), —NHC(O)O(alkyl), —NHC(O)NH$_2$, —NHC(O)NH(alkyl), —NHC(O)N(alkyl)$_2$, —SO$_2$NH$_2$, —SO$_2$NH(alkyl), —SO$_2$N(alkyl)$_2$, and R$^{40}$, in which R$^{30}$ is alkyl or alkyl substituted with one substituent selected from the group consisting of halo, —O(alkyl), and —S(alkyl), and R$^{40}$ is furyl, imidazolyl, indazolidinyl, isoquinolyl, isothiazolyl, isoxazolyl, morpholinyl, naphthyl, naphthyridyl, 1,2,3-oxadiazolyl, oxazolyl, phenyl, piperidinyl, piperazinyl, pyrazinyl, pyrazolyl, pyridyl, pyrimidinyl, pyrrolidinyl, pyrrolyl, quinazolyl, quinolyl, quinoxalyl, tetrazolyl, 1,2,3-thiadiazolyl, 1,3,4-thiadiazolyl, thiazolyl, thienyl, 1,2,3-triazolyl, or thiomorpholinyl, in which each R$^4$ moiety is unsubstituted or substituted with one, two, or three substituents independently selected from the group consisting of alkyl, alkenyl, alkynyl, cycloalkyl, halo, =O, —CN, —OH, —SH, —NO$_2$, —CF$_3$, —CH$_2$CF$_3$, —CF$_2$CF$_3$, —OCF$_3$, —OCH$_2$CF$_3$, —OCF$_2$CF$_3$, —O(alkyl), —S(alkyl), —S(O)(alkyl), —SO$_2$(alkyl), —C(O)H, —C(O)(alkyl), —C(O)OH, —C(O)O(alkyl), —NH$_2$, —NH(alkyl), —N(alkyl)$_2$, —C(O)NH$_2$, —C(O)NH(alkyl), —C(O)N(alkyl)$_2$, —OC(O)(alkyl), —OC(O)O(alkyl), —OC(O)NH$_2$, —OC(O)NH(alkyl), —OC(O)N(alkyl)$_2$, —NHC(O)H, —NHC(O)(alkyl), —NHC(O)O(alkyl), —NHC(O)NH$_2$, —NHC(O)NH(alkyl), —NHC(O)N(alkyl)$_2$, —SO$_2$NH$_2$, —SO$_2$NH(alkyl), and —SO$_2$N(alkyl)$_2$.

Substituted cycloalkyl, cycloalkenyl, and heterocyclyl moieties are those moieties substituted with one, two, or three substituents independently selected from the group consisting of alkyl, halo, —CN, —OH, —NH$_2$, —CF$_3$, —OR$^{30}$, —SR$^{30}$, —S(O)(alkyl), —SO$_2$(alkyl), —C(O)H, —C(O)(alkyl), —C(O)OH, —C(O)O(alkyl), —NH(alkyl), —N(alkyl)$_2$, —C(O)NH$_2$, —C(O)NH(alkyl), —C(O)N(alkyl)$_2$, and R$^{40}$, in which the phenyl is unsubstituted or substituted with one, two, or three substituents independently selected from the group consisting of halo, —CN, —OH, —NH$_2$, and —CF$_3$.

"Hydroxyl protecting moiety" means selectively introducible and removable moieties which protect —OH moieties against undesirable side reactions. Hydroxyl protecting moieties include 4-nitrobenzyloxycarbonyl, 4-bromobenzyloxycarbonyl, 4-methoxybenzyloxycarbonyl, 3,4-dimethoxybenzyloxycarbonyl, tert-butoxycarbonyl, diphenylmethoxycarbonyl, 2,2,2-trichloroethoxycarbonyl, 2,2,2-tribromoethoxycarbonyl, 2-(trimethylsilyl)ethoxycarbonyl, 2-(phenylsulfonyl)ethoxycarbonyl, allyloxycarbonyl, acetyl, chloroacetyl, dichloroacetyl, trichloroacetyl, trifluoroacetyl, methoxyacetyl, phenoxyacetyl, pivaloyl, propionyl, 2-methylpropionyl, benzoyl, tert-butyl, 2,2,2-trichloroethyl, 2-trimethylsilylethyl, 1,1-dimethyl-2-propenyl, 3-methyl-3-butenyl, para-methoxybenzyl, 3,4-dimethoxybenzyl, diphenylmethyl, triphenylmethyl, tetrahydrofuryl, benzyloxymethyl, 2-methoxyethoxymethyl, 2,2,2-trichloroethoxymethyl, 2-(trimethylsilyl)ethoxymethyl, methanesulfonyl, para-toluenesulfonyl, trimethylsilyl, triethylsilyl, triisopropylsilyl, diethylisopropylsilyl, tert-butyldimethylsilyl, tert-butyldiphenylsilyl, diphenylmethylsilyl, and tert-butylmethoxyphenylsilyl.

These variable moieties may combine to provide a seventh embodiment of this invention, which embodiment is directed to compounds having formula (I), formula (I)-f, formula (I)-g, formula (II), formula (II)-f, and formula (II)-g, and pharmaceutically acceptable salts, prodrugs, and salts of prodrugs thereof, in which R$^1$ is —OH, —OR$^9$, —OC(O)OR$^9$, —OC(O)NH$_2$, —OC(O)NHR$^{10}$, or —OC(O)NR$^{10}$R$^{11}$;

R$^2$ is hydrogen or R$^P$, in which R$^P$ is a hydroxyl protecting moiety;

one of R$^3$ and R$^4$ is hydrogen, and the other is —OH, —OR$^{13}$, —OC(O)OR$^{13}$, —NH$_2$, —NHC(O)OR$^{14}$, —NHR$^{15}$, —NR$^{15}$R$^{16}$, —OC(O)NH$_2$, —OC(O)NHR$^{15}$, —OC(O)NR$^{15}$R$^{16}$, —N(R$^{17}$)C(O)NH$_2$, —N(R$^{17}$)C(O)NHR$^{15}$, or —N(R$^{17}$)C(O)NR$^{15}$R$^{16}$; or R$^3$ and R$^4$ together are =O or =NOR$^{19}$;

one of R$^5$ and R$^6$ is hydrogen, and the other is —OH, —OR$^{20}$, —OC(O)OR$^{20}$, —NH$_2$, —NHC(O)OR$^{14}$, —NHR$^{21}$, —NR$^{21}$R$^{22}$, —OC(O)NH$_2$, —OC(O)NHR$^{21}$, —OC(O)NR$^{21}$R$^{22}$, —N(R$^{23}$)C(O)NH$_2$, —N(R$^{23}$)C(O)NHR$^{21}$, or —N(R$^{23}$)C(O)NR$^{21}$R$^{22}$; or R$^5$ and R$^6$ together are =O;

R$^7$ is hydrogen and R$^8$ is —OH, —OR$^{25}$, —OC(O)R$^{25}$, —OC(O)OR$^{25}$, —OC(O)NH$_2$, —OC(O)NHR$^{26}$, or —OC(O)NR$^{26}$R$^{27}$; or R$^7$ and R$^8$ together are =O;

R$^9$, R$^{13}$, R$^{19}$, R$^{20}$, and R$^{25}$ are independently alkyl, cycloalkyl, —(CH$_2$)alkenyl, —(CH$_2$)alkynyl, alkyl substituted with one substituent selected from the group consisting of cycloalkyl, aryl, heteroaryl, and heterocyclyl, —(CH$_2$)alkenyl substituted with one substituent selected from the group consisting of cycloalkyl, aryl, heteroaryl, and heterocyclyl, or —(CH$_2$)alkynyl substituted with one substituent selected from the group consisting of cycloalkyl, aryl, heteroaryl, and heterocyclyl;

R$^{10}$, R$^{11}$, R$^{15}$, R$^{16}$, R$^{21}$, R$^{22}$, R$^{26}$, and R$^{27}$ are independently alkyl, cycloalkyl, —(CH$_2$)alkenyl, —(CH$_2$)alkynyl, aryl, heteroaryl, heterocyclyl, alkyl substituted with one substituent selected from the group consisting of cycloalkyl, aryl, heteroaryl, heterocyclyl, —NH$_2$, —NHR$^{31}$, and —NR$^{31}$R$^{32}$, —(CH$_2$)alkenyl substituted with one substituent selected from the group consisting of cycloalkyl, aryl, heteroaryl, heterocyclyl, —NH$_2$, —NHR$^{31}$, and —NR$^{31}$R$^{32}$, or —(CH$_2$)alkynyl substituted with one substituent selected from the group consisting of cycloalkyl, aryl, heteroaryl, heterocyclyl, —NH$_2$, —NHR$^{31}$, and —NR$^{31}$R$^{32}$;

R$^{14}$ is alkyl or alkyl substituted with one or two independently selected aryl substituents;

R$^{17}$ and R$^{23}$ are independently hydrogen or alkyl;

R$^{31}$ and R$^{32}$ are independently alkyl, cycloalkyl, aryl, heteroaryl, heterocyclyl, —(CH$_2$)alkenyl, —(CH$_2$)alkynyl, alkyl substituted with one substituent selected from the group consisting of cycloalkyl, aryl, heteroaryl, heterocyclyl, —NH$_2$, —NH(alkyl), and —N(alkyl)$_2$, —(CH$_2$)alkenyl substituted with one substituent selected from the group consisting of cycloalkyl, aryl, heteroaryl, heterocyclyl, —NH$_2$, —NH(alkyl), and —N(alkyl)$_2$, or —(CH$_2$)alkynyl substituted with one substituent selected from the group consisting of cycloalkyl, aryl, heteroaryl, heterocyclyl, —NH$_2$, —NH(alkyl), and —N(alkyl)$_2$; and X$^1$ is hydrogen, fluoride, chloride, or bromide;

compounds having formula (I), formula (I)-f, formula (I)-g, formula (II), formula (II)-f, or formula (II)-g, and pharmaceutically acceptable salts, prodrugs, and salts of prodrugs thereof, in which R$^1$ is —OH or —OR$^9$;

R$^2$ is hydrogen or R$^P$, in which R$^P$ is a hydroxyl protecting moiety;

one of R$^3$ and R$^4$ is hydrogen, and the other is —OH, —OR$^{13}$, —OC(O)OR$^{13}$, —NH$_2$, —NHC(O)OR$^{14}$, —NHR$^{15}$, —NR$^{15}$R$^{16}$, —OC(O)NH$_2$, —OC(O)NHR$^{15}$, —OC(O)NR$^{15}$R$^{16}$, —N(R$^{17}$)C(O)NH$_2$, —N(R$^{17}$)C(O)NHR$^{15}$, or —N(R$^{17}$)C(O)NR$^{15}$R$^{16}$; or R$^3$ and R$^4$ together are =O;

one of R$^5$ and R$^6$ is hydrogen, and the other is —OH, —OR$^{20}$, —OC(O)OR$^{20}$, —NH$_2$, —NHC(O)OR$^{14}$, —NHR$^{21}$, —NR$^{21}$R$^{22}$, —OC(O)NH$_2$, —OC(O)NHR$^{21}$, —OC(O)NR$^{21}$R$^{22}$, N(R$^{23}$C(O)NH$_2$, —N(R$^{23}$)C(O)NHR$^{21}$, or —N(R$^{23}$)C(O)NR$^{21}$R$^{22}$; or R$^5$ and R$^6$ together are =O;

R$^7$ is hydrogen and R$^8$ is —OH, —OR$^{25}$, —OC(O)R$^{25}$, —OC(O)OR$^{25}$, —OC(O)NH$_2$, —OC(O)NHR$^{26}$, or —OC(O)NR$^{26}$R$^{27}$; or R$^7$ and R$^8$ together are =O;

R$^9$, R$^{13}$, R$^{20}$, and R$^{25}$ are independently alkyl, cycloalkyl, —(CH$_2$)alkenyl, —(CH$_2$)alkynyl, alkyl substituted with one substituent selected from the group consisting of cycloalkyl, aryl, heteroaryl, and heterocyclyl, —(CH$_2$)alkenyl substituted with one substituent selected from the group consisting of cycloalkyl, aryl, heteroaryl, and heterocyclyl, or —(CH$_2$) alkynyl substituted with one substituent selected from the group consisting of cycloalkyl, aryl, heteroaryl, and heterocyclyl;

R$^{15}$, R$^{16}$, R$^{21}$, R$^{22}$, R$^{26}$, and R$^{27}$ are independently alkyl, cycloalkyl, —(CH$_2$)alkenyl, —(CH$_2$)alkynyl, aryl, heteroaryl, heterocyclyl, alkyl substituted with one substituent selected from the group consisting of cycloalkyl, aryl, heteroaryl, heterocyclyl, —NH$_2$, —NHR$^{31}$, and —NR$^{31}$R$^{32}$, —(CH$_2$)alkenyl substituted with one substituent selected from the group consisting of cycloalkyl, aryl, heteroaryl, heterocyclyl, —NH$_2$, —NHR$^{31}$, and —NR$^{31}$R$^{32}$, or —(CH$_2$)alkynyl substituted with one substituent selected from the group consisting of cycloalkyl, aryl, heteroaryl, heterocyclyl, —NH$_2$, —NHR$^{31}$, and —NR$^{31}$R$^{32}$;

R$^{14}$ is alkyl or alkyl substituted with one or two independently selected aryl substituents;

R$^{17}$ and R$^{23}$ are independently hydrogen or alkyl;

R$^{31}$ and R$^{32}$ are independently alkyl, cycloalkyl, aryl, heteroaryl, heterocyclyl, —(CH$_2$)alkenyl, —(CH$_2$)alkynyl, alkyl substituted with one substituent selected from the group consisting of cycloalkyl, aryl, heteroaryl, heterocyclyl, —NH$_2$, —NH(alkyl), and —N(alkyl)$_2$, —(CH$_2$)alkenyl substituted with one substituent selected from the group consisting of cycloalkyl, aryl, heteroaryl, heterocyclyl, —NH$_2$, —NH(alkyl), and —N(alkyl)$_2$, or —(CH$_2$)alkynyl substituted with one substituent selected from the group consisting of cycloalkyl, aryl, heteroaryl, heterocyclyl, —NH$_2$, —NH(alkyl), and —N(alkyl)$_2$; and X$^1$ is hydrogen, fluoride, chloride, or bromide;

compounds having formula (I), formula (I)-f, formula (I)-g, formula (II), formula (II)-f, and formula (II)-g, and pharmaceutically acceptable salts, prodrugs, and salts of prodrugs thereof, in which R$^1$ is —OH or —OR$^9$;

R$^2$ is hydrogen;

one of R$^3$ and R$^4$ is hydrogen, and the other is —OH, —OR$^{13}$, —NH$_2$, —NHC(O)OR$^{14}$, —NHR$^{15}$, —NR$^{15}$R$^{16}$, —OC(O)NH$_2$, —OC(O)NHR$^{15}$, or —OC(O)NR$^{15}$R$^{16}$; or R$^3$ and R$^4$ together are =O;

one of R$^5$ and R$^6$ is hydrogen, and the other is —OH, —OR$^{20}$, —OC(O)OR$^{20}$, —OC(O)NH$_2$, —OC(O)NHR$^{21}$, or —OC(O)NR$^{21}$R$^{22}$;

or

R$^5$ and R$^6$ together are =O;

R$^7$ is hydrogen and R$^8$ is —OH, —OR$^{25}$, —OC(O)R$^{25}$, —OC(O)OR$^{25}$, —OC(O)NH$_2$, —OC(O)NHR$^{26}$, or —OC(O)NR$^{26}$R$^{27}$; or R$^7$ and R$^8$ together are =O;

R$^9$, R$^{13}$, R$^{20}$, and R$^{25}$ are independently alkyl, —(CH$_2$) alkenyl, —(CH$_2$)alkynyl, alkyl substituted with one substituent selected from the group consisting of aryl, heteroaryl, and heterocyclyl, —(CH$_2$)alkenyl substituted with one substituent selected from the group consisting of aryl, heteroaryl, and heterocyclyl, or —(CH$_2$)alkynyl substituted with one substituent selected from the group consisting of aryl, heteroaryl, and heterocyclyl;

R$^{15}$, R$^{16}$, R$^{21}$, R$^{22}$, R$^{26}$, and R$^{27}$ are independently alkyl, cycloalkyl, —(CH$_2$)alkenyl, —(CH$_2$)alkynyl, aryl, heteroaryl, heterocyclyl, alkyl substituted with one substituent selected from the group consisting of aryl, heteroaryl, heterocyclyl, —NH$_2$, —NHR$^{31}$, and —NR$^{31}$R$^{32}$, (CH$_2$)alkenyl substituted with one substituent selected from the group consisting of aryl, heteroaryl, heterocyclyl, —NH$_2$, —NHR$^{31}$, and —NR$^{31}$R$^{32}$, or —(CH$_2$)alkynyl substituted with one substituent selected from the group consisting of aryl, heteroaryl, heterocyclyl, —NH$_2$, —NHR$^{31}$, and —NR$^{31}$R$^{32}$;

R$^{14}$ is alkyl or alkyl substituted with phenyl;

R$^{31}$ and R$^{32}$ are independently alkyl, —(CH$_2$)alkenyl, —(CH$_2$)alkynyl, alkyl substituted with one substituent selected from the group consisting of aryl and heteroaryl, —(CH$_2$)alkenyl substituted with one substituent selected from the group consisting of aryl and heteroaryl, or —(CH$_2$) alkynyl substituted with one substituent selected from the group consisting of aryl and heteroaryl; and X$^1$ is hydrogen, fluoride, chloride, or bromide;

compounds having formula (I), formula (I)-f, formula (I)-g, formula (II), formula (II)-f, and formula (II)-g, and pharmaceutically acceptable salts, prodrugs, and salts of prodrugs thereof, in which $R^1$ is —OH or —$OR^9$;

$R^2$ is hydrogen;

one of $R^3$ and $R^4$ is hydrogen, and the other is —OH, —$NH_2$, —$NHR^{15}$, —$NR^{15}R^{16}$ or —NHC(O)$OR^{14}$; or $R^3$ and $R^4$ together are =O;

$R^5$ is hydrogen, and $R^6$ is —OH, —OC(O)$NH_2$, —OC(O)$NHR^{21}$, or —OC(O)$NR^{21}R^{22}$;

$R^7$ is hydrogen and $R^8$ is —OH, —$OR^{25}$, —OC(O)$R^{25}$, —OC(O)$NH_2$, —OC(O)$NHR^{26}$, or —OC(O)$NR^{26}R^{27}$;

$R^{21}$ and $R^{22}$ are independently methyl, ethyl, propyl, butyl, prop-2-enyl, or prop-2-ynyl, each of which is independently unsubstituted or substituted with one substituent selected from the group consisting of —$NH_2$ and —$NHR^{31}$;

$R^{15}$, $R^{16}$, $R^{26}$ and $R^{27}$ are independently methyl, ethyl, propyl, butyl, prop-2-enyl, prop-2-ynyl, cyclopropyl, cyclopentyl, cyclohexyl, cyclopropyl substituted with phenyl, phenyl substituted with two independently selected halo substituents, or methyl, ethyl, propyl, butyl, prop-2-enyl, or prop-2-ynyl, each of which is substituted with one substitutent selected from the group consisting of (4,5-dihydroisoxazol-5-yl), phenyl, pyridyl, pyrimidinyl, thienyl, isoxazolyl, oxazolyl, quinolyl and isoquinolyl, in which substituent is unsubstituted or substituted with one substituent selected from the group consisting of —F, —Cl, —Br, methyl, —OH, (methyl)O—, phenyl, pyridyl, pyrimidinyl, thienyl and isoxazolyl;

$R^9$ and $R^{25}$ are independently methyl, ethyl, propyl, butyl, prop-2-enyl, or prop-2-ynyl, each of which is independently unsubstituted or substituted with one substituent selected from the group consisting of thienyl, isoxazolyl, 4,5-dihydroisoxazol-5-yl, phenyl, pyridyl, pyrimidinyl, quinolyl, and isoquinolyl, in which each substituent is independently unsubstituted or substituted with one substituent selected from the group consisting of phenyl, pyridyl, pyrimidinyl, thienyl, isoxazolyl, quinolyl, isoquinolyl, and phenyl substituted with one substituent selected from the group consisting of methyl, —OH, (methyl)O—, —F, —Cl, and —Br;

$R^{14}$ is tert-butyl or phenylmethyl;

$R^{31}$ is methyl, ethyl, or propyl, each of which is independently unsubstituted or substituted with one substituent selected from the group consisting of phenyl, pyridyl, quinolyl, isoquinolyl, thienyl, pyrimidinyl, isoxazolyl, and oxazolyl, in which each substituent is unsubstituted or substituted with one or two or three substituents independently selected from the group consisting of —F, —Cl, —Br, —I, methyl, —OH, and (methyl)O—; and $X^1$ is hydrogen, fluoride, chloride, or bromide; and compounds having formula (I), formula (I)-f, formula (I)-g, formula (II), formula (II)-f, or formula (II)-g, and pharmaceutically acceptable salts, prodrugs, and salts of prodrugs thereof, in which $R^1$ is —OH, (methyl)O—, (ethyl)O—, (prop-2-ynyl)O—, (prop-2-enyl)O—, (phenylmethyl)O—, (3-(5-pyridin-2-ylthien-2-yl)prop-2-ynyl)O—, (3-(quinolin-3-yl)prop-2-enyl)O—, (3-(3-(pyridin-2-yl)isoxazol-5-yl)prop-2-ynyl)O—, or (3-(5-(pyrimidin-2-yl)thien-2-yl)prop-2-ynyl)O—;

$R^2$ is hydrogen;

$R^3$ is hydrogen, and $R^4$ is —OH, —$NH_2$, (tert-butyl)OC(O)NH—, (phenylmethyl)OC(O)NH—, (methyl)NH—, (methyl)$_2$N—, (ethyl)NH—, (propyl)NH—, (butyl)NH—, (prop-2-ynyl)NH—, (prop-2-enyl) NH—, (methyl)(phenylmethyl)N—, (3-(quinolin-3-yl)prop-2-enyl)NH—, (3-(3-pyridin-2-ylisoxazol-5-yl)prop-2-ynyl)NH—(3-(5-(pyrimidin-2-yl)thien-2-yl)prop-2-ynyl)NH—(3-(quinolin-3-yl)propyl)NH— (3-(quinolin-3-yl)butyl)NH— or (4-(quinolin-3-yl)butyl)NH—; or $R^3$ and $R^4$ together are =O;

$R^5$ is hydrogen, and $R^6$ is (2-aminoethyl)NHC(O)O—, (2-(dimethylamino)ethyl)NHC(O)O—, (3-aminopropyl) NHC(O)O—, (4-aminobutyl)NHC(O)O—, (2-((1-(2-methoxyphenyl)ethyl)amino)ethyl)NHC(O)O—, (2-((quinolin-3-ylmethyl)amino)ethyl)NHC(O)O—, (2-((quinolin-4-ylmethyl)amino)ethyl)NHC(O)O—, or (2-((pyridin-2-ylmethyl)amino)ethyl)NHC(O)O—;

$R^7$ is hydrogen;

$R^8$ is —OH, (methyl)O—, (ethyl)O—, (propyl)O—, (prop-2-ynyl)O—, (prop-2-enyl)O—, (3-(5-(pyridin-2-yl)thien-2-yl)prop-2-ynyl)O—, (3-(quinolin-3-yl)prop-2-enyl)O—, (3-(3-(pyridin-2-yl)isoxazol-5-yl)prop-2-ynyl)O—, (3-(5-(pyrimidin-2-yl)thien-2-yl)prop-2-ynyl)O—, (3-phenyl-4,5-dihydroisoxazol-5-yl)CH$_2$O—, (3-(pyridin-2-yl)-4,5-dihydroisoxazol-5-yl)CH$_2$O—, (3-(4-fluorophenyl)-4,5-dihydroisoxazol-5-yl)CH$_2$O—, ((pyridin-2-yl)methyl)C(O)O—, (2-(pyridin-3-yl)ethyl)C(O)O—, (ethyl)NHC(O)O—, (propyl)NHC(O)O—, (isopropyl)NHC(O)O—, (3,5-dichlorophenyl)NHC(O)O—, (cyclopropyl)NHC(O)O—, (cyclopentyl)NHC(O)O—, (cyclohexyl)NHC(O)O—, (2-phenylcyclopropyl)NHC(O)O—, (phenylmethyl)NHC(O)O—, (2-fluorophenylmethyl)NHC(O)O—, (3-fluorophenylmethyl)NHC(O)O—, (4-fluorophenylmethyl)NHC(O)O—, ((4-methylphenyl)methyl)NHC(O)O—, ((4-methoxyphenyl)methyl)NHC(O)O—, ((pyridin-2-yl)methyl)NHC(O)O—, ((pyridin-3-yl)methyl)NHC(O)O—, ((pyridin-4-yl)methyl)NHC(O)O—, ((3-(phenyl)-4,5-dihydroisoxazol-5-yl)methyl)NHC(O)O—, (2-(pyridin-2-yl)ethyl)NHC(O)O—, (2-(pyridin-3-yl)ethyl)NHC(O)O—, (2-(pyridin-4-yl)ethyl)NHC(O)O—, or (quinolin-4-ylmethyl)NHC(O)O—; and $X^1$ is hydrogen or fluoride, chloride, or bromide.

An example of an $R^1$ moiety for the practice of this invention using compounds having formula (I), formula (I)-f, formula (I)-g, formula (II), formula (II)-f, or formula (II)-g, is —OH.

An example of $R^2$ moiety for the practice of this invention using compounds having formula (I), formula (I)-f, formula (I)-g, formula (II), formula (II)-f, or formula (II)-g, is hydrogen.

Examples of $R^3$ and $R^4$ moieties for the practice of this invention using compounds having formula (I), formula (I)-f, or formula (I)-g are hydrogen and —$NH_2$, respectively, or taken together are =O.

An example of an $R^3$ moiety for the practice of this invention using compounds having formula (II), formula (II)-f, or formula (II)-g is hydrogen.

Examples of $R^4$ moieties for the practice of this invention using compounds having formula (II), formula (II)-f, or formula (II)-g are —$NH_2$, (tert-butyl)OC(O)NH—, and (phenylmethyl)OC(O)NH—.

An example of an $R^5$ moiety for the practice of this invention using compounds having formula (I), formula (I)-f, or formula (I)-g is hydrogen.

Examples of $R^6$ moieties for the practice of this invention using compounds having formula (I), formula (I)-f, or formula (I)-g are (2-((1-(2-methoxyphenyl)ethyl)amino) ethyl)NHC(O)O—, (2-aminoethyl)NHC(O)O—, (2-((quinolin-3-ylmethyl)amino)ethyl)NHC(O)O—, (2-((quinolin-4-ylmethyl)amino)ethyl)NHC(O)O—, and (2-((pyridin-2-ylmethyl)amino)ethyl)NHC(O)O—.

An example of an $R^7$ moiety for the practice of this invention using compounds having formula (I), formula (I)-f, formula (I)-g, formula (II), formula (II)-f, or formula (II)-g is hydrogen.

Examples of an $R^8$ moiety for the practice of this invention using compounds having formula (II), formula (II)-f, or formula (II)-g are —OH, (propyl)O—, (3-phenyl-4,5-dihydroisoxazol-5-yl)methoxy, (3-(pyridin-2-yl)-4,5-dihydroisoxazol-5-yl)methoxy, (3-(4-fluorophenyl)-4,5-dihydroisoxazol-5-yl)methoxy, ((pyridin-2-yl)methyl)C(O)O—, (2-(pyridin-3-yl)ethyl)C(O)O—, (propyl)NHC(O)O—, (isopropyl)NHC(O)O—, (cyclopentyl)NHC(O)O—, (cyclohexyl)NHC(O)O—, (2-phenylcyclopropyl)NHC(O)O—, (3,5-dichlorophenyl)NHC(O)O—, (phenylmethyl)NHC(O)O—, ((2-fluorophenyl)methyl)NHC(O)O—, ((3-fluorophenyl)methyl)NHC(O)O—, ((4-fluorophenyl)methyl)NHC(O)O—, ((4-methylphenyl)methyl)NHC(O)O—, ((4-methoxyphenyl)methyl)NHC(O)O—, ((pyridin-2-yl)methyl)NHC(O)O—, ((pyridin-3-yl)methyl)NHC(O)O—, ((pyridin-4-yl)methyl)NHC(O)O—, ((3-(phenyl)-4,5-dihydroisoxazol-5-yl)methyl)NHC(O)O—, (2-(pyridin-2-yl)ethyl)NHC(O)O—, (2-(pyridin-3-yl)ethyl)NHC(O)O—, and (2-(pyridin-4-yl)ethyl)NHC(O)O—.

An example of an $X^1$ moiety for the practice of this invention using compounds having formula (I), formula (I)-f, formula (I)-g, formula (II), formula (II)-f, or formula (I)-g, is hydrogen.

These specific moieties of the compounds may combine with the fixed moieties thereof to form an eighth embodiment of this invention, which embodiment is directed to compounds, and salts, prodrugs, and salts of prodrugs thereof, which are useful as antibacterials, the compounds having formula (I)

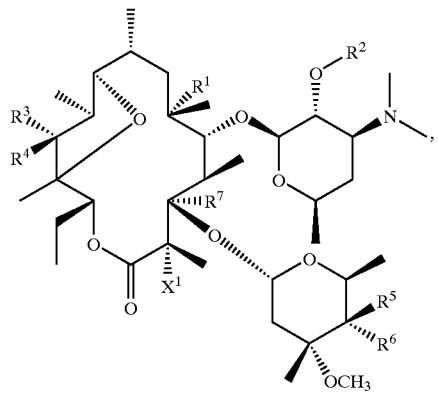

(I)

formula (I)-f,

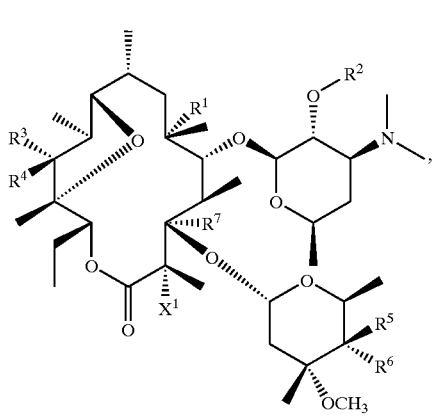

(I)-f and formula (I)-g,

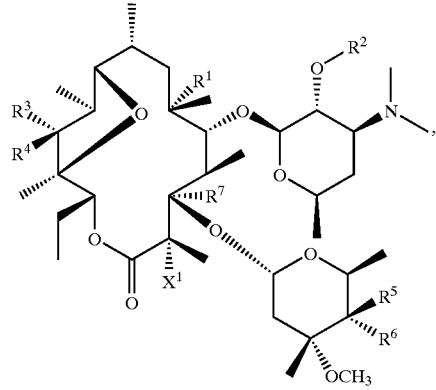

(I)-g in which $R^1$ is —OH; $R^2$ is hydrogen; $R^3$ is hydrogen and $R^4$ is —NH$_2$, or $R^3$ and $R^4$ together are =O; $R^5$ and $R^7$ are hydrogen;

$R^6$ is —OC(O)NHR$^{21}$; $R^{21}$ is alkyl substituted with one substituent selected from the group consisting of —NH$_2$ and —NHR$^{31}$; $R^{31}$ is alkyl substituted with one substituent selected from the group consisting of phenyl and pyridyl, in which the phenyl is substituted with —O(alkyl) and the pyridyl is unfused or fused with phenyl; and $X^1$ is hydrogen;

compounds, and salts, prodrugs, and salts of prodrugs thereof, which are useful as antibacterials, the compounds having formula (I)

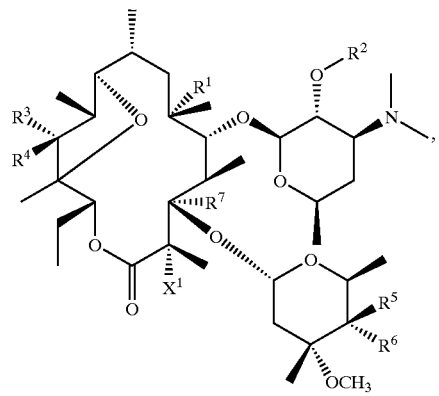

(I)

formula (I)-f,

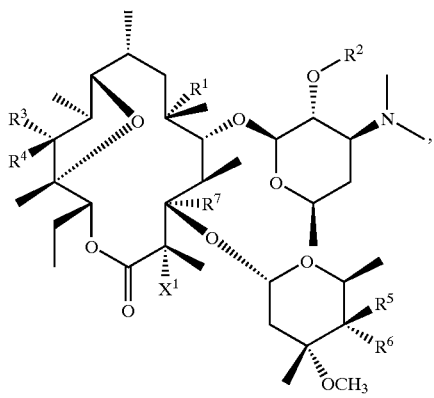

(I)-f and formula (I)-g,

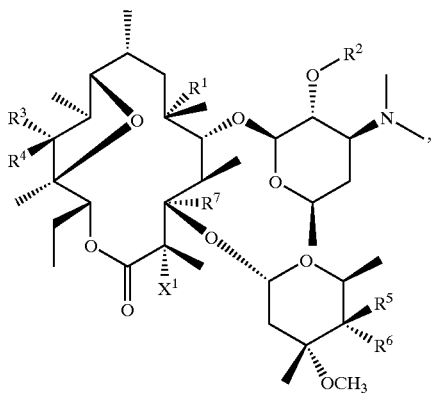

(I)-g in which

R$^1$ is —OH; R$^2$ is hydrogen; R$^3$ is hydrogen and R$^4$ is —NH$_2$, or R$^3$ and R$^4$ together are =O; R$^5$ and R$^7$ are hydrogen; R$^6$ is —OC(O)NHR$^{21}$; R$^{21}$ is C$_2$-alkyl substituted with one substituent selected from the group consisting of —NH$_2$ and —NHR$^{31}$; R$^{31}$ is C$_1$–C$_2$-alkyl substituted with one substituent selected from the group consisting of phenyl and pyridyl, in which the phenyl is substituted with (methyl)O— and the pyridyl is unfused or fused with phenyl; and X$^1$ is hydrogen;

compounds, and salts, prodrugs, and salts of prodrugs thereof, which are useful as antibacterials, the compounds having formula (I), formula (I)-f, or formula (I)-g, in which R$^1$ is —OH; R$^2$ is hydrogen; R$^3$ is hydrogen; R$^4$ is —NH$_2$; R$^5$ and R$^7$ are hydrogen; R$^6$ is (2-((1-(2-methoxyphenyl)ethyl)amino)ethyl)NHC(O)O—, (2-aminoethyl)NHC(O)O—, (2-((quinolin-3-ylmethyl)amino)ethyl)NHC(O)O—, (2-((quinolin-4-ylmethyl)amino)ethyl)NHC(O)O—, or (2-((pyridin-2-ylmethyl)amino)ethyl)NHC(O)O—; and X$^1$ is hydrogen;

compounds having formula (I), formula (I)-f, or formula (I)-g, and salts, prodrugs, and salts of prodrugs thereof, which are useful as antibacterials, in which R$^1$ is —OH; R$^2$ is hydrogen; R$^3$ and R$^4$ together are =O; R$^5$ and R$^7$ are hydrogen; R$^6$ is (2-((1-(2-methoxyphenyl)ethyl)amino)ethyl)NHC(O)O—, (2-aminoethyl)NHC(O)O—, (2-((quinolin-3-ylmethyl)amino)ethyl)NHC(O)O—, (2-((quinolin-4-ylmethyl)amino)ethyl)NHC(O)O—, or (2-((pyridin-2-ylmethyl)amino)ethyl)NHC(O)O—; and X$^1$ is hydrogen;

compounds, and salts, prodrugs, and salts of prodrugs thereof, which are useful as antibacterials, the compounds having formula (II)

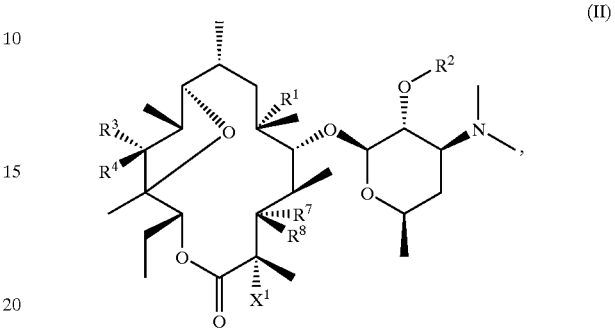

(II)

formula (II)-f,

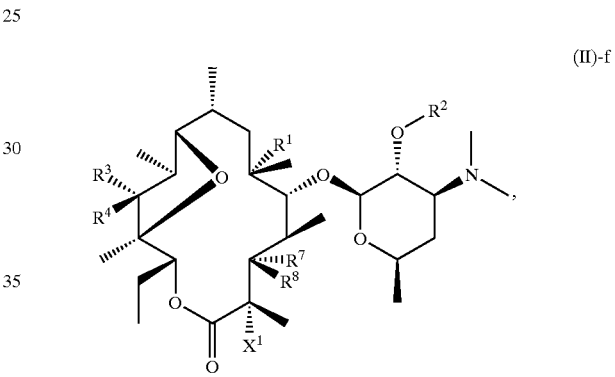

(II)-f or formula (II)-g,

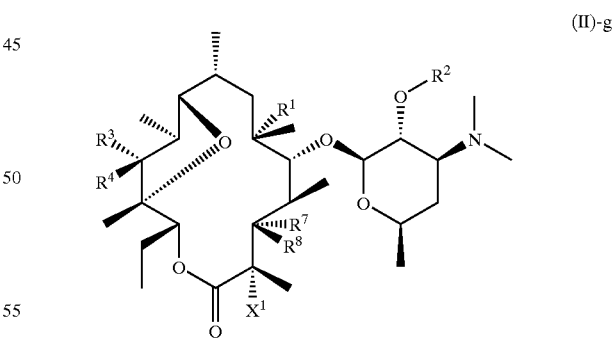

(II)-g in which

R$^1$ is —OH; R$^2$ is hydrogen; R$^3$ and R$^7$ are hydrogen; R$^4$ is —NH$_2$ or —NHC(O)OR$^{14}$; R$^8$ is —OH, —OR$^{25}$, —OC(O)R$^{25}$, or —OC(O)NHR$^{26}$; R$^{14}$ is alkyl substituted with phenyl; R$^{25}$ is alkyl or alkyl substituted with one substituent selected from the group consisting of pyridyl and 4,5-dihydroisoxazolyl, in which the 4,5-dihydroisoxazolyl is substituted with one substituent selected from the group consisting of pyridyl and phenyl, in which the phenyl is unsubstituted or substituted with one halo substituent; $R^{26}$ is alkyl, cycloalkyl, cycloalkyl substituted with phenyl, phenyl substituted with two independently selected halo substituents, or alkyl substituted with one substituent selected from the group consisting of phenyl, pyridyl, and 4,5-dihydroisoxazolyl, in which the phenyl is unsubstituted or substituted with one substituent selected from the group consisting of alkyl, halo and —O(alkyl), and the 4,5-dihydroisoxazolyl is substituted with phenyl; and $X^1$ is hydrogen;

compounds, and salts, prodrugs, and salts of prodrugs thereof, which are useful as antibacterials, the compounds having formula (II)

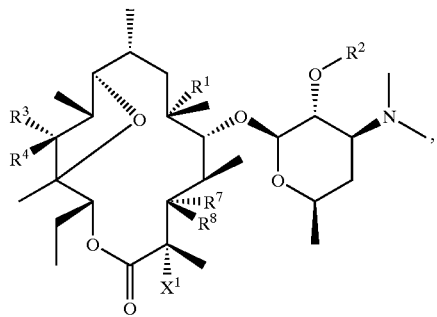

formula (II)-f,

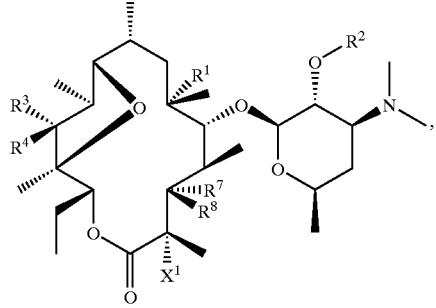

or formula (II)-g,

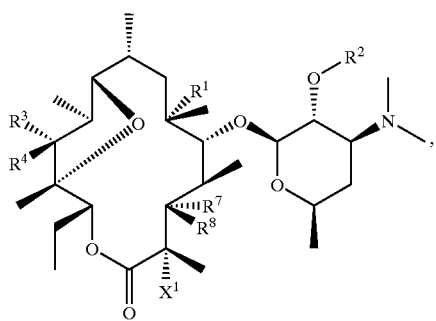

in which $R^1$ is —OH; $R^2$, $R^3$ and $R^7$ are hydrogen; $R^4$ is —NH$_2$ or —NHC(O)OR$^{14}$; $R^8$ is —OH, —OR$^{25}$, —OC(O)R$^{25}$, or —OC(O)NHR$^{26}$; $R^{14}$ is phenylmethyl; $R^{25}$ is $C_3$-alkyl or $C_1$–$C_2$-alkyl substituted with one substituent selected from the group consisting of pyridyl and 4,5-dihydroisoxazolyl, in which the 4,5-dihydroisoxazolyl is substituted with one substituent selected from the group consisting of pyridyl and phenyl, in which the phenyl is unsubstituted or substituted with one halo substituent; $R^{26}$ is $C_3$-alkyl, $C_5$–$C_6$-cycloalkyl, $C_3$-cycloalkyl substituted with phenyl, phenyl substituted with two independently selected halo substituents, or $C_1$–$C_2$-alkyl substituted with one substituent selected from the group consisting of phenyl, pyridyl, and 4,5-dihydroisoxazolyl, in which the phenyl is unsubstituted or substituted with one substituent selected from the group consisting of methyl, halo and (methyl)O—, and the 4,5-dihydroisoxazolyl is substituted with phenyl; and $X^1$ is hydrogen;

compounds having formula (II), formula (II)-f, or formula (II)-g, and salts, prodrugs, and salts of prodrugs thereof, which are useful as antibacterials, in which $R^1$ is —OH; $R^2$, $R^3$ and $R^7$ are hydrogen; $R^4$ is —NH$_2$; $R^8$ is —OH, (propyl)O—, (3-phenyl-4,5-dihydroisoxazol-5-yl)methoxy, (3-(pyridin-2-yl)-4,5-dihydroisoxazol-5-yl)methoxy, (3-(4-fluorophenyl)-4,5-dihydroisoxazol-5-yl)methoxy, ((pyridin-2-yl)methyl)C(O)O—, (2-(pyridin-3-yl)ethyl)C(O)O—, (propyl)NHC(O)O—, (isopropyl)NHC(O)O—, (cyclopentyl)NHC(O)O—, (cyclohexyl)NHC(O)O—, (2-phenylcyclopropyl)NHC(O)O—, (3,5-dichlorophenyl)NHC(O)O—, (phenylmethyl)NHC(O)O—, ((2-fluorophenyl)methyl)NHC(O)O—, ((3-fluorophenyl)methyl)NHC(O)O—, ((4-fluorophenyl)methyl)NHC(O)O—, ((4-methylphenyl)methyl)NHC(O)O—, ((4-methoxyphenyl)methyl)NHC(O)O—, ((pyridin-2-yl)methyl)NHC(O)O—, ((pyridin-3-yl)methyl)NHC(O)O—, ((pyridin-4-yl)methyl)NHC(O)O—, ((3-(phenyl)-4,5-dihydroisoxazol-5-yl)methyl)NHC(O)O—, (2-(pyridin-2-yl)ethyl)NHC(O)O—, (2-(pyridin-3-yl)ethyl)NHC(O)O—, or (2-(pyridin-4-yl)ethyl)NHC(O)O—; and $X^1$ is hydrogen;

compounds having formula (II), formula (II)-f, or formula (II)-g, and salts, prodrugs, and salts of prodrugs thereof, which are useful as antibacterials, in which $R^1$ is —OH; $R^2$, $R^3$ and $R^7$ are hydrogen; $R^4$ is (phenylmethyl)OC(O)NH—; $R^8$ is —OH, (propyl)O—, (3-phenyl-4,5-dihydroisoxazol-5-yl)CH$_2$O—, (3-(pyridin-2-yl)-4,5-dihydroisoxazol-5-yl)CH$_2$O—, (3-(4-fluorophenyl)-4,5-dihydroisoxazol-5-yl)CH$_2$O—, ((pyridin-2-yl)methyl)C(O)O—, (2-(pyridin-3-yl)ethyl)C(O)O—, (propyl)NHC(O)O—, (isopropyl)NHC(O)O—, (cyclopentyl)NHC(O)O—, (cyclohexyl)NHC(O)O—, (2-phenylcyclopropyl)NHC(O)O—, (3,5-dichlorophenyl)NHC(O)O—, (phenylmethyl)NHC(O)O—, ((2-fluorophenyl)methyl)NHC(O)O—, ((3-fluorophenyl)methyl)NHC(O)O—, ((4-fluorophenyl)methyl)NHC(O)O—, ((4-methylphenyl)methyl)NHC(O)O—, ((4-methoxyphenyl)methyl)NHC(O)O—, ((pyridin-2-yl)methyl)NHC(O)O—, ((pyridin-3-yl)methyl)NHC(O)O—, ((pyridin-4-yl)methyl)NHC(O)O—, ((3-(phenyl)-4,5-dihydroisoxazol-5-yl)methyl)NHC(O)O—, (2-(pyridin-2-yl)ethyl)NHC(O)O—, (2-(pyridin-3-yl)ethyl)NHC(O)O—, or (2-(pyridin-4-yl)ethyl)NHC(O)O—; and $X^1$ is hydrogen; and compounds, and salts, prodrugs, and salts of prodrugs thereof, which are useful as antibacterials, including (1-(S or R),2R,5R,6S,7S,8R,9S,11R,12S,13S)-2-ethyl-9-hydroxy-1,5,7,9,11,13-hexamethyl-4,14-dioxo-8-((3,4,6-trideoxy-3-(dimethylamino)-β-D-xylo-hexopyranosyl) oxy)-3,15-dioxabicyclo(10.2.1)pentadec-6-yl 4-O-(((2-aminoethyl)amino)carbonyl)-2,6-dideoxy-3-C-methyl-3-O-methyl-α-L-ribo-hexopyranoside;

(1-(S or R),2R,5R,6S,7S,8R,9S,11R,12S,13R,14S)-14-amino-2-ethyl-9-hydroxy-1,5,7,9,11,13-hexamethyl-4-oxo-8-((3,4,6-trideoxy-3-(dimethylamino)-β-D-xylo-hexopyranosyl)oxy-3,15-dioxabicyclo(10.2.1)pentadec-6-yl 2,6-dideoxy-4-O-(((2-((1-(2-methoxyphenyl)ethyl)amino)ethyl)amino)carbonyl)-3-C-methyl-3-O-methyl-α-L-ribo-hexopyranoside;

(1-(S or R),2R,5R,6S,7S,8R,9S,11R,12S,13S)-2-ethyl-9-hydroxy-1,5,7,9,11,13-hexamethyl-4,14-dioxo-8-((3,4,6-trideoxy-3-(dimethylamino)-β-D-xylo-hexopyranosyl)oxy)-3,15-dioxabicyclo(10.2.1)pentadec-6-yl 2,6-dideoxy-3-C-methyl-3-O-methyl-4-O-(((2-((quinolin-3-ylmethyl)amino)ethyl)amino)carbonyl)-α-L-ribo-hexopyranoside;

(1-(S or R),2R,5R,6S,7S,8R,9S,11R,12S,13S)-2-ethyl-9-hydroxy-1,5,7,9,11,13-hexamethyl-4,14-dioxo-8-((3,4,6-trideoxy-3-(dimethylamino)-β-D-xylo-hexopyranosyl)oxy)-3,15-dioxabicyclo(10.2.1)pentadec-6-yl 2,6-dideoxy-3-C-methyl-3-O-methyl-4-O-(((2-((quinolin-4-ylmethyl)amino)ethyl)amino)carbonyl)-α-L-ribo-hexopyranoside;

(1-(S or R),2R,5R,6S,7S,8R,9S,11R,12S,13S)-2-ethyl-9-hydroxy-1,5,7,9,11,13-hexamethyl-4,14-dioxo-8-((3,4,6-trideoxy-3-(dimethylamino)-β-D-xylo-hexopyranosyl)oxy)-3,15-dioxabicyclo(10.2.1)pentadec-6-yl 2,6-dideoxy-3-C-methyl-3-O-methyl-4-O-(((2-((pyridin-2-ylmethyl)amino)ethyl)amino)carbonyl)-α-L-ribo-hexopyranoside;

(1-(S or R),2R,5R,6S,7S,8R,9S,11R,12S,13R,14S)-14-amino-2-ethyl-9-hydroxy-1,5,7,9,11,13-hexamethyl-4-oxo-8-((3,4,6-trideoxy-3-(dimethylamino)-β-D-xylo-hexopyranosyl)oxy)-3,15-dioxabicyclo(10.2.1)pentadec-6-yl 2,6-dideoxy-3-C-methyl-3-O-methyl-4-O-(((2-((pyridin-2-ylmethyl)amino)ethyl)amino)carbonyl)-α-L-ribo-hexopyranoside;

(1S,2R,4S,5R,6S,7S,8R,11R,12-(S or R),13S,14R)-13-amino-11-ethyl-4,7-dihydroxy-2,4,6,8,12,14-hexamethyl-9-oxo-10,15-dioxabicyclo(10.2.1)pentadec-5-yl 3,4,6-trideoxy-3-(dimethylamino)-β-D-xylo-hexopyranoside;

benzyl (1S,2R,4S,5R,6S,7S,8R,11R,12-(S or R),13S,14R)-11-ethyl-4,7-dihydroxy-2,4,6,8,12,14-hexamethyl-9-oxo-5-((3,4,6-trideoxy-3-(dimethylamino)-β-D-xylo-hexopyranosyl)oxy)-10,15-dioxabicyclo(10.2.1)pentadec-13-ylcarbamate;

(1-(S or R),2R,5R,6S,7S,8R,9S,11R,12S,13R,14S)-14-amino-2-ethyl-9-hydroxy-1,5,7,9,11,13-hexamethyl-4-oxo-8-((3,4,6-trideoxy-3-(dimethylamino)-β-D-xylo-hexopyranosyl)oxy)-3,15-dioxabicyclo(10.2.1)pentadec-6-yl isopropylcarbamate;

(1-(S or R),2R,5R,6S,7S,8R,9S,11R,12S,13R,14S)-14-amino-2-ethyl-9-hydroxy-1,5,7,9,11,13-hexamethyl-4-oxo-8-((3,4,6-trideoxy-3-(dimethylamino)-β-D-xylo-hexopyranosyl)oxy)-3,15-dioxabicyclo(10.2.1)pentadec-6-yl cyclopentylcarbamate;

(1-(S or R),2R,5R,6S,7S,8R,9S,11R,12S,13R,14S)-14-amino-2-ethyl-9-hydroxy-1,5,7,9,11,13-hexamethyl-4-oxo-8-((3,4,6-trideoxy-3-(dimethylamino)-β-D-xylo-hexopyranosyl)oxy)-3,15-dioxabicyclo(10.2.1)pentadec-6-yl cyclohexylcarbamate;

(1-(S or R),2R,5R,6S,7S,8R,9S,11R,12S,13R,14S)-14-amino-2-ethyl-9-hydroxy-1,5,7,9,11,13-hexamethyl-4-oxo-8-((3,4,6-trideoxy-3-(dimethylamino)-β-D-xylo-hexopyranosyl)oxy)-3,15-dioxabicyclo(10.2.1)pentadec-6-yl 4-fluorobenzylcarbamate;

(1-(S or R),2R,5R,6S,7S,8R,9S,11R,12S,13R,14S)-14-amino-2-ethyl-9-hydroxy-1,5,7,9,11,13-hexamethyl-4-oxo-8-((3,4,6-trideoxy-3-(dimethylamino)-β-D-xylo-hexopyranosyl)oxy)- 3,15-dioxabicyclo(10.2.1)pentadec-6-yl 3,5-dichlorophenylcarbamate;

(1-(S or R),2R,5R,6S,7S,8R,9S,11R,12S,13R,14S)-14-amino-2-ethyl-9-hydroxy-1,5,7,9,11,13-hexamethyl-4-oxo-8-((3,4,6-trideoxy-3-(dimethylamino)-β-D-xylo-hexopyranosyl)oxy)-3,15-dioxabicyclo(10.2.1)pentadec-6-yl (1S,2R)-2-phenylcyclopropylcarbamate compound with (1-(S or R),2R,5R,6S,7S,8R,9S,11R,12S,13R,14S)-14-amino-2-ethyl-9-hydroxy-1,5,7,9,11,13-hexamethyl-4-oxo-8-((3,4,6-trideoxy-3-(dimethylamino)-β-D-xylo-hexopyranosyl)oxy)-3,15-dioxabicyclo(10.2.1)pentadec-6-yl (1R,2S)-2-phenylcyclopropylcarbamate (1:1);

(1-(S or R),2R,5R,6S,7S,8R,9S,11R,12S,13R,14S)-14-amino-2-ethyl-9-hydroxy-1,5,7,9,11,13-hexamethyl-4-oxo-8-((3,4,6-trideoxy-3-(dimethylamino)-β-D-xylo-hexopyranosyl)oxy)-3,15-dioxabicyclo(10.2.1)pentadec-6-yl propylcarbamate;

(1S,2R,4S,5R,6S,7S,8R,11R,12-(S or R),13S,14R)-13-amino-11-ethyl-7-((3-(4-fluorophenyl)-4,5-dihydroisoxazol-5-yl)methoxy)-4-hydroxy-2,4,6,8,12,14-hexamethyl-9-oxo-10,15-dioxabicyclo(10.2.1)pentadec-5-yl 3,4,6-trideoxy-3-(dimethylamino)-β-D-xylo-hexopyranoside;

(1S,2R,4S,5R,6S,7S,8R,11R,12-(S or R),13S,14R)-13-amino-11-ethyl-4-hydroxy-2,4,6,8,12,14-hexamethyl-9-oxo-7-((3-pyridin-2-yl-4,5-dihydroisoxazol-5-yl)methoxy)-10,15-dioxabicyclo(10.2.1)pentadec-5-yl 3,4,6-trideoxy-3-(dimethylamino)-β-D-xylo-hexopyranoside;

(1-(S or R),2R,5R,6S,7S,8R,9S,11R,12S,13R,14S)-14-amino-2-ethyl-9-hydroxy-1,5,7,9,11,13-hexamethyl-4-oxo-8-((3,4,6-trideoxy-3-(dimethylamino)-β-D-xylo-hexopyranosyl)oxy)-3,15-dioxabicyclo(10.2.1)pentadec-6-yl pyridin-2-ylmethylcarbamate;

(1-(S or R),2R,5R,6S,7S,8R,9S,11R,12S,13R,14S)-14-amino-2-ethyl-9-hydroxy-1,5,7,9,11,13-hexamethyl-4-oxo-8-(( 3,4,6-trideoxy-3-(dimethylamino)-β-D-xylo-hexopyranosyl)oxy)-3,15-dioxabicyclo(10.2.1)pentadec-6-yl 2-pyridin-4-ylethylcarbamate;

(1S,2R,4S,5R,6S,7S,8R,11R,12-(S or R),13S,14R)-13-amino-11-ethyl-4-hydroxy-2,4,6,8,12,14-hexamethyl-9-oxo-7-propoxy-10,15-dioxabicyclo(10.2.1)pentadec-5-yl 3,4,6-trideoxy-3-(dimethylamino)-β-D-xylo-hexopyranoside;

(1S,2R,4S,5R,6S,7S,8R,11R,12-(S or R),13S,14R)-13-amino-11-ethyl-4-hydroxy-2,4,6,8,12,14-hexamethyl-9-oxo-7-((3-phenyl-4,5-dihydroisoxazol-5-yl)methoxy)-10,15-dioxabicyclo(10.2.1)pentadec-5-yl 3,4,6-trideoxy-3-(dimethylamino)-β-D-xylo-hexopyranoside;

(1-(S or R),2R,5R,6S,7S,8R,9S,11R,12S,13R,14S)-14-amino-2-ethyl-9-hydroxy-1,5,7,9,11,13-hexamethyl-4-oxo-8-((3,4,6-trideoxy-3-(dimethylamino)-β-D-xylohexopyranosyl)oxy)-3,15-dioxabicyclo(10.2.1)pentadec-6-yl (3-phenyl-4,5-dihydroisoxazol-5-yl)methylcarbamate;

(1-(S or R),2R,5R,6S,7S,8R,9S,11R,12S,13R,14S)-14-amino-2-ethyl-9-hydroxy-1,5,7,9,11,13-hexamethyl-4-oxo-8-((3,4,6-trideoxy-3-(dimethylamino)-β-D-xylo-hexopyranosyl)oxy)-3,15-dioxabicyclo(10.2.1)pentadec-6-yl pyridin-4-ylmethylcarbamate;

(1-(S or R),2R,5R,6S,7S,8R,9S,11R,12S,13R,14S)-14-amino-2-ethyl-9-hydroxy-1,5,7,9,11,13-hexamethyl-4-oxo-8-((3,4,6-trideoxy-3-(dimethylamino)-β-D-xylo-hexopyranosyl)oxy)-3,15-dioxabicyclo(10.2.1)pentadec-6-yl pyridin-3-ylmethylcarbamate;

(1-(S or R),2R,5R,6S,7S,8R,9S,11R,12S,13R,14S)-14-amino-2-ethyl-9-hydroxy-1,5,7,9,11,13-hexamethyl-4-oxo-8-((3,4,6-trideoxy-3-(dimethylamino)-β-D-xylo-hexopyranosyl)oxy)-3,15-dioxabicyclo(10.2.1)pentadec-6-yl pyridin-2-ylacetate;

(1-(S or R),2R,5R,6S,7S,8R,9S,11R,12S,13R,14S)-14-amino-2-ethyl-9-hydroxy-1,5,7,9,11,13-hexamethyl-4-oxo-8-(( 3,4,6-trideoxy-3-(dimethylamino)-β-D-xylo-hexopyranosyl)oxy)-3,15-dioxabicyclo(10.2.1)pentadec-6-yl 2-pyridin-3-ylethylcarbamate;

(1-(S or R),2R,5R,6S,7S,8R,9S,11R,12S,13R,14S)-14-amino-2-ethyl-9-hydroxy-1,5,7,9,11,13-hexamethyl-4-oxo-8-((3,4,6-trideoxy-3-(dimethylamino)-β-D-xylo-hexopyranosyl)oxy)-3,15-dioxabicyclo(10.2.1)pentadec-6-yl 2-pyridin-2-ylethylcarbamate;

(1-(S or R),2R,5R,6S,7S,8R,9S,11R,12S,13R,14S)-14-amino-2-ethyl-9-hydroxy-1,5,7,9,11,13-hexamethyl-4-oxo-8-((3,4,6-trideoxy-3-(dimethylamino)-β-D-xylo-hexopyranosyl)oxy)-3,15-dioxabicyclo(10.2.1)pentadec-6-yl 3-fluorobenzylcarbamate;

(1-(S or R),2R,5R,6S,7S,8R,9S,11R,12S,13R,14S)-14-amino-2-ethyl-9-hydroxy-1,5,7,9,11,13-hexamethyl-4-oxo-8-((3,4,6-trideoxy-3-(dimethylamino)-β-D-xylo-hexopyranosyl)oxy)-3,15-dioxabicyclo(10.2.1)pentadec-6-yl 2-fluorobenzylcarbamate;

(1-(S or R),2R,5R,6S,7S,8R,9S,11R,12S,13R,14S)-14-amino-2-ethyl-9-hydroxy-1,5,7,9,11,13-hexamethyl-4-oxo-8-((3,4,6-trideoxy-3-(dimethylamino)-β-D-xylo-hexopyranosyl)oxy)-3,15-dioxabicyclo(10.2.1)pentadec-6-yl 4-methylbenzylcarbamate;

(1-(S or R),2R,5R,6S,7S,8R,9S,11R,12S,13R,14S)-14-amino-2-ethyl-9-hydroxy-1,5,7,9,11,13-hexamethyl-4-oxo-8-((3,4,6-trideoxy-3-(dimethylamino)-β-D-xylo-hexopyranosyl)oxy)-3,15-dioxabicyclo(10.2.1)pentadec-6-yl 3-pyridin-3-ylpropanoate;

(1-(S or R),2R,5R,6S,7S,8R,9S,11R,12S,13R,14S)-14-amino-2-ethyl-9-hydroxy-1,5,7,9,11,13-hexamethyl-4-oxo-8-((3,4,6-trideoxy-3-(dimethylamino)-β-D-xylo-hexopyranosyl)oxy)-3,15-dioxabicyclo(10.2.1)pentadec-6-yl 4-methoxybenzylcarbamate; and (1-(S or R),2R,5R,6S,7S,8R,9S,11R,12S,13R,14S)-14-amino-2-ethyl-9-hydroxy-1,5,7,9,11,13-hexamethyl-4-oxo-8-((3,4,6-trideoxy-3-(dimethylamino)-β-D-xylo-hexopyranosyl)oxy)-3,15-dioxabicyclo(10.2.1)pentadec-6-yl benzylcarbamate.

Compounds of this invention contain asymmetrically substituted carbon atoms in the R or S configuration, in which the terms "R" and "S" are as defined by the IUPAC 1974 Recommendations for Section E, Fundamental Stereochemistry, Pure Appl. Chem. (1976) 45, 13–10. Compounds having asymmetrically substituted carbon atoms with equal amounts of R and S configurations are racemic at those carbon atoms. Atoms with an excess of one configuration over the other are assigned the configuration which is present in the higher amount, preferably an excess of about 85%–90%, more preferably an excess of about 95%–99%, and still more preferably an excess greater than about 99%. Accordingly, this invention is meant to embrace racemic mixtures, relative and absolute stereoisomers, and mixtures of relative and absolute stereoisomers of the compounds thereof.

Compounds of this invention may also contain carbon-carbon double bonds or carbon-nitrogen double bonds in the Z or E configuration, in which the term "Z" represents the larger two substituents on the same side of a carbon-carbon or carbon-nitrogen double bond and the term "E" represents the larger two substituents on opposite sides of a carbon-carbon or carbon-nitrogen double bond. The compounds may also exist as an equilibrium mixture of Z or E configurations.

Compounds of this invention which contain —OH, —NH—, or —CO$_2$H moieties may have attached thereto prodrug-forming moieties. The prodrug-forming moieties are removed by metabolic processes and release the compounds having the freed hydroxyl, amino, or carboxylic acid in vivo. Prodrugs are useful for adjusting such pharmacokinetic properties of the compounds as solubility and/or hydrophobicity, absorption in the gastrointestinal tract, bioavailability, tissue penetration, and rate of clearance.

Compounds of this invention may exist as acid addition salts, basic addition salts, or zwitterions. Salts of the compounds are prepared during their isolation or following their purification. Acid addition salts of the compounds are those derived from the reaction of the compounds with an acid. For example, the acetate, adipate, alginate, bicarbonate, citrate, aspartate, benzoate, benzenesulfonate, bisulfate, butyrate, camphorate, camphorsufonate, digluconate, formate, fumarate, glycerophosphate, glutamate, hemisulfate, heptanoate, hexanoate, hydrochloride, hydrobromide, hydroiodide, lactobionate, lactate, maleate, mesitylenesulfonate, methanesulfonate, naphthylenesulfonate, nicotinate, oxalate, pamoate, pectinate, persulfate, phosphate, picrate, propionate, succinate, tartrate, thiocyanate, trichloroacetic, trifluoroacetic, para-toluenesulfonate, and undecanoate salts of the compounds and prodrugs thereof are contemplated as being embraced by this invention. When the compounds contain carboxylic acids, basic addition salts may be prepared therefrom by reaction with a base such as the hydroxide, carbonate, or bicarbonate of cations such as lithium, sodium, potassium, calcium, and magnesium.

Compounds of this invention may be administered with or without an excipient. Excipients include encapsulating materials or formulation additives such as absorption accelerators, antioxidants, binders, buffers, coating agents, coloring agents, diluents, disintegrating agents, emulsifiers, extenders, fillers, flavoring agents, humectants, lubricants, perfumes, preservatives, propellants, releasing agents, sterilizing agents, sweeteners, solubilizers, wetting agents, and mixtures thereof. Excipients for orally administered compounds in solid dosage forms include agar, alginic acid, aluminum hydroxide, benzyl alcohol, benzyl benzoate, 1,3-butylene glycol, castor oil, cellulose, cellulose acetate, cocoa butter, corn starch, corn oil, cottonseed oil, ethanol, ethyl acetate, ethyl carbonate, ethyl cellulose, ethyl laureate, ethyl oleate, gelatin, germ oil, glucose, glycerol, groundnut oil, isopropanol, isotonic saline, lactose, magnesium hydroxide, magnesium stearate, malt, olive oil, peanut oil, potassium phosphate salts, potato starch, propylene glycol, Ringer's solution, talc, tragacanth, water, safflower oil, sesame oil, sodium carboxymethyl cellulose, sodium lauryl sulfate, sodiumphosphate salts, soybean oil, sucrose, tetrahydrofurfuryl alcohol, and mixtures thereof. Excipients for ophthalmically and orally administered compounds in liquid dosage forms include benzyl alcohol, benzyl benzoate, 1,3-butylene glycol, castor oil, corn oil, cottonseed oil, ethanol, ethyl acetate, ethyl carbonate, fatty acid esters of sorbitan, germ oil, groundnut oil, glycerol, isopropanol, olive oil, polyethylene glycols, propylene glycol, sesame oil, tetrahydrofurfuryl alcohol, water, and mixtures thereof. Excipients for osmotically administered compounds include chlorofluorohydrocarbons, ethanol, isopropanol, water, and mixtures thereof. Excipients for parenterally administered compounds include 1,3-butanediol, castor oil, corn oil, cottonseed oil, germ oil, groundnut oil, liposomes, oleic acid, olive oil, peanut oil, Ringer's solution, safflower oil, sesame oil, soybean oil, U.S.P. or isotonic sodium chloride solution, water, and mixtures thereof. Excipients for rectally and vaginally administered compounds include cocoa butter, polyethylene glycol, wax, and mixtures thereof.

Compounds of this invention may be administered orally, ophthalmically, osmotically, parenterally (subcutaneously, intramuscularly, intrasternally, intravenously), rectally, topically, transdermally, and vaginally. Orally administered compounds in solid dosage forms may be administered as capsules, dragees, granules, pills, powders, and tablets. Ophthalmically and orally administered compounds in liquid dosage forms may be administered as elixirs, emulsions, microemulsions, solutions, suspensions, and syrups. Osmotically and topically administered compounds may be administered as creams, gels, inhalants, lotions, ointments, pastes, powders, solutions, and sprays. Parenterally administered compounds may be administered as aqueous or oleaginous solutions or aqueous or oleaginous suspensions in which the suspensions comprise crystalline, amorphous, or otherwise insoluble forms of the compounds. Rectally and vaginally administered compounds may be administered as creams, gels, lotions, ointments, and pastes.

Therapeutically effective amounts of the compounds of this invention depend on the recepient of treatment, the disorder being treated and the severity thereof, the composition comprising the compounds, the time of administration, the route of administration, the duration of treatment, the potency of the compounds, and the rate of excretion of the compounds. The daily therapeutically effective amount of the compounds administered to a patient in single or divided doses range from about 0.1 to about 200 mg/kg body weight, preferably from about 0.25 to about 100 mg/kg body weight. Single dose compositions contain these amounts of the compounds or combinations of submultiples thereof.

To determine antibacterial activity of compounds of this invention, twelve petri dishes, each containing successive aqueous dilutions of test compounds in sterilized Brain Heart Infusion agar (Difco 0418-01-5) (10 mL), were inoculated with 1:100 dilutions of the representative microorganisms in TABLE 1 using a Steers replicator block (or 1:10 dilutions for slow-growing Streptococcus strains), co-incubated at 35–37° C. for 20–24 hours with a plate having no compound, and inspected visually to provide the minimum inhibitory concentration (MIC), in $\mu$g/mL, by which is meant the lowest concentration of the test compound which yielded no growth, a slight haze, or sparsely isolated colonies on the inoculums spot as compared to growth in the control plate.

TABLE 1

| Microorganism | Code |
| --- | --- |
| *Staphylococcus aureus* NCTC10649M | AA |
| *Staphylococcus aureus* A5177 | BB |
| *Staphylococcus aureus* PIU 2043 | CC |
| *Staphylococcus aureus* 1775 | DD |
| *Streptococcus pyrogenes* EES61 | EE |
| *Streptococcus pyrogenes* 930 | FF |
| *Streptococcus pyrogenes* PIU 2548 | GG |
| *Streptococcus pneumoniae* ATCC 6303 | HH |
| *Streptococcus pneumoniae* 5979 | JJ |
| *Streptococcus pneumoniae* 5649 | KK |
| *Enterococcus faecalis* PIU 1967 | LL |
| *Enterococcus faecium* GYR 1632 | MM |
| *Moraxella catarrhalis* 2604 | NN |
| *Haemophilus influenzae* GYR 1435 | PP |
| *Escherichia coli* JUHL | QQ |

Representative compounds of this invention displayed antibacterial activity superior to the control, which control demonstrated no antibacterial activity. This antibacterial activity demonstrates the usefulness of the compounds as antibacterials.

It is also meant to be understood that certain metabolites of compounds of this invention, which metabolites are produced by in vitro or in vivo metabolic processes, would also be useful as antibacterials and are meant to be embraced by this invention.

It is still also meant to be understood that certain precursor compounds, which precursor compounds may be metabolized in vitro or in vivo to form compounds of this invention, are meant to be embraced by this invention.

Compounds of this invention may also be prepared by synthetic chemical processes, examples of which synthetic chemical processes, and intermediates employed in the processes, are shown hereinbelow. It is meant to be understood that the order of the steps in the processes may be varied, reagents, solvents, and reaction conditions may be substituted for those specifically mentioned, and vulnerable moieties may be protected and deprotected, as necessary, during the process.

Abbreviations used herein are CBZ-NOS for N-(benzyloxycarbonyloxy)succinimide; CDI for 1,1'-carbonyldiimidazole; DBU for 1,8-diazabicyclo(5.4.0)undec-7-ened; dppe for 1,2-bis(diphenylphosphino)ethane; DIEA for N,N-diisopropylethylamine; DMAP for 4-(N,N-dimethylamino)pyridine; DMF for N,N-dimethylformamide; EDCI for 1-(3-dimethylaminopropyl)-3-carbodiimide hydrochloride; THF for tetrahydrofuran.

SCHEME 1

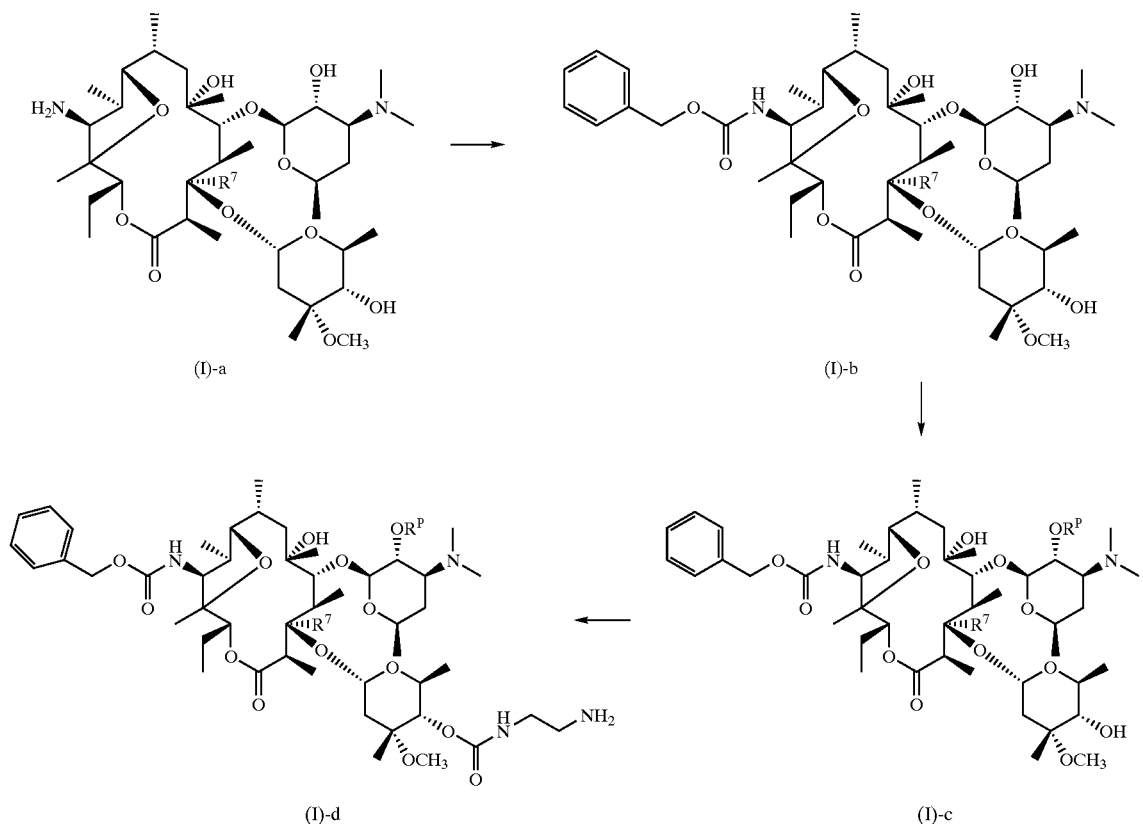

Compound having formula (I)-a may be prepared from erythromycin A as described in Bioorg. & Medicinal Chemistry Letters, Vol. 5, No. 12, 1307–1310.

Compounds having formula (I)-a may be converted to compounds having formula (I)-b by reacting the former, an amino-protecting group precursor, and a first base.

Examples of amino-protecting group precursors include benzyl chloroformate, dibenzyl dicarbonate, and N-(benzyloxycarbonyloxy)succinimide.

Examples of first bases include pyridine, sodium bicarbonate, sodium carbonate, triethylamine, tributylamine, and diisopropylethylamine.

The reaction is typically conducted over about 1 hour to about 3 days, at about −10° C. to about 35° C., in solvents such as dichloromethane, methanol, tetrahydrofuran, ether, N,N-dimethylformamide, acetonitrile, ethyl acetate, acetone, 1,2-dimethoxyethane, dimethylsulfoxide, dioxane, chloroform, and mixtures thereof.

Compounds having formula (I)-b may be converted to compounds having formula (I)-c by reacting the former, a hydroxyl-protecting group precursor, and the first base, with or without 4-(N,N-dimethylamino)pyridine.

Examples of hydroxyl-protecting group precursors include acetic anhydride, benzoic anhydride, benzyl chloroformate, hexamethyldisilazane, trimethylsilyl chloride, and triethylsilyl chloride.

The reaction is typically conducted over about 1 hour to about 48 hours, at about −10° C. to about 75° C., in solvents such as tetrahydrofuran, ether, N,N-dimethylformamide, acetonitrile, ethyl acetate, acetone, 1,2-dimethoxyethane, dichloromethane, chloroform, and mixtures thereof.

Compounds having formula (I)-c may be converted to compounds having formula (I)-d by (a) reacting the former, a carbonylating agent, and a second base, with or without 4-(N,N-dimethylamino)pyridine, and (b) reacting the product of step (a) and 2-aminoethylamine.

Examples of carbonylating agents include 1,1'-carbonyldiimidazole, phosgene, diphosgene, triphosgene and disuccinimidyl carbonate.

Examples of second bases include 1,8-diazabicyclo(5.4.0)undec-7-ene, triethylamine, diisopropylethyl amine, pyridine, and lutidine.

Step (a) is typically conducted at about −78° C. to about 100° C., over about 1 hour to about 24 hours, in solvents such as toluene, ether, tetrahydrofuran, dichloromethane, N,N-dimethylformamids, benzene, pyridine and mixtures thereof.

Step (b) is typically conducted at about 0° C. to about 50° C. over about 1 hour to about 4 days in solvents such as tetrahydrofuran, acetonitrile, dichloromethane, chloroform, toluene, benzene ether, and mixtures thereof.

SCHEME 2

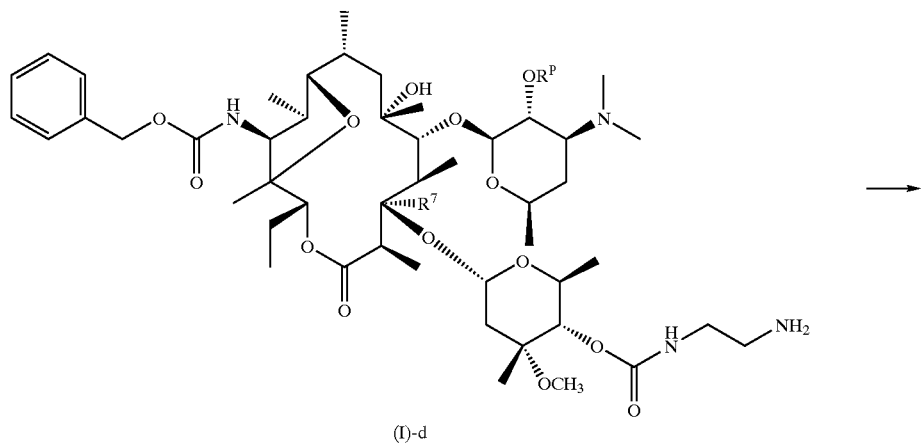

(I)-d

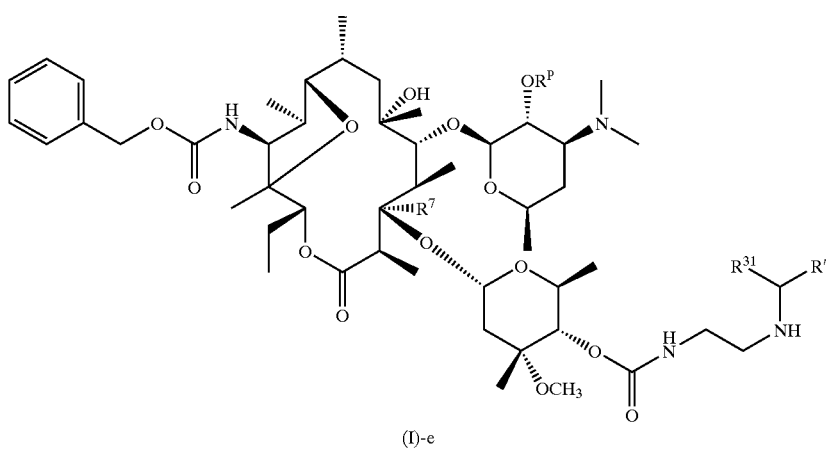

(I)-e

Compounds having formula (I)-d may be converted to compounds having formula (I)-e by (a) reacting the former and a compound having formula $R^{31}C(O)R'$, in which R' is hydrogen or alkyl, and (b) reacting the product of step (a) and a reducing agent, with or without a first acid.

Examples of compounds having formula $R^{31}C(O)R'$ in which R' is hydrogen include pyridine-2-carbaldehyde, pyridine-3-carbaldehyde, pyridine-4-carbaldehyde, pyrimidine-4-carbaldehyde, quinoline-3-carbaldehyde, quinoline-4-carbaldehyde, phenylacetaldehyde, 2-(trifluoromethyl)benzaldehyde, 2-methoxybenzaldehyde, and cinnamaldehyde.

Examples of compounds having formula $R^{31}C(O)R'$ in which R' is alkyl include 1-phenylethanone, 1-(3,4-dichlorophenyl)propan-1-one, 1-(2-methoxyphenyl)propan-1-one, 1-(2-methoxyphenyl)ethanone, 2,2,2-trifluoro-1-(2-methoxyphenyl)ethanone, and 1-(3,5-bis(trifluoromethyl)phenyl)ethanone.

Examples of the reducing agents include sodium borohydride, sodium cyanoborohydride, sodium triacetoxyborohydride, zinc and hydrochloric acid, iron pentacarbonyl and alcoholic potassium hydroxide, borane-pyridine, and formic acid.

Examples of first acids include acetic acid, formic acid, and hydrochloric acid.

Step (a) is typically conducted at about 25° C. to about 150° C., over about 1 hour to about 24 hours, in solvents such as tetrahydrofuran, dichloromethane, toluene, benzene, dimethyl sulfoxide, acetonitrile, xylene, N,N-dimethylformamide, and mixtures thereof.

Step (b) is typically conducted at about −10° C. to about 50° C., over about 1 hour to about 24 hours, in solvents such as acetonitrile, methanol, ethanol, dichloromethane, toluene, benzene, N,N-dimethylformaide, and mixtures thereof.

SCHEME 3

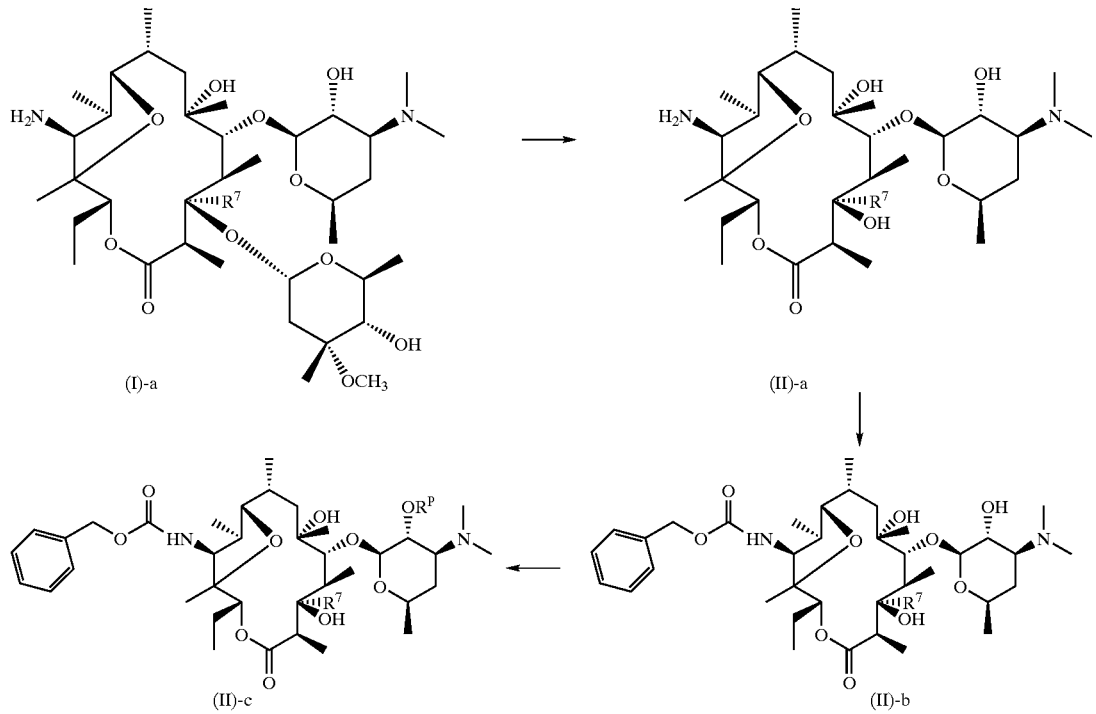

Compounds having formula (I)-a may be converted to compounds having formula (II)-a by reacting the former and a second acid.

Examples of second acids include hydrochloric acid, sulfuric acid, perchloric acid, chloroacetic acid, dichloroacetic acid, and trifluoroacetic acid.

The reaction is typically conducted at about −10° C. to about 70° C., over about 1 hour to about 72 hours, in solvents such as dichloromethane, tetrahydrofuran, methanol, water, ethanol, isopropanol, butanol, and mixtures thereof.

Compounds having formula (II)-a may be converted to compounds having formula (II)-b by using the same reagents and under the same conditions described for the conversion of compounds having formula (I)-a to compounds having formula (I)-b in SCHEME 1.

Compounds having formula (II)-b may be converted to compounds having formula (II)-c by using the same reagents and under the same conditions described for the conversion of compounds having formula (I)-b to compounds having formula (I)-c in SCHEME 1.

SCHEME 4

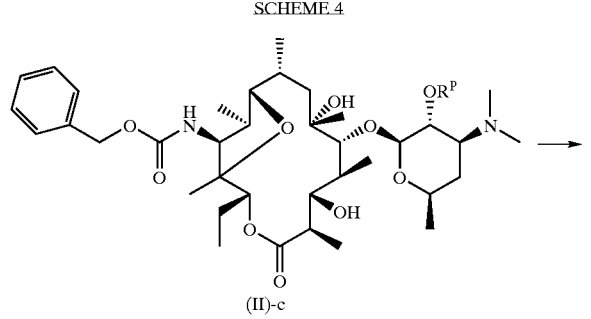

-continued

Compounds having formula (II)-c may be converted to compounds having formula (II)-d by reacting the former, a compound having formula $R^{25}COOH$, an acid activating agent, with or without the second base, and with or without 4-(N,N-dimethylamino)pyridine.

Examples of acid activating agents include 1-(3-dimethylaminopropyl)-3-ethylcarbodiimide hydrochloride, 1,3-dicyclohexylcarbodiimide, and thionyl chloride.

Examples of compounds having formula $R^{25}COOH$ include 2-pyridylacetic acid, 3-pyridylpropanoic acid, phenylacetic acid, 3-quinolin-3-ylacrylic acid, 4-(5-pyridin-2-ylthien-2-yl)but-3-enoic acid, propanoic acid, and butanoic acid.

The reaction is typically conducted at about −10° C. to about 35° C., over about 1 hour to about 3 days, in solvents such as dichloromethane, chloroform, toluene, ethyl acetate, acetonitrile, tetrahydrofuran, and mixtures thereof.

SCHEME 5

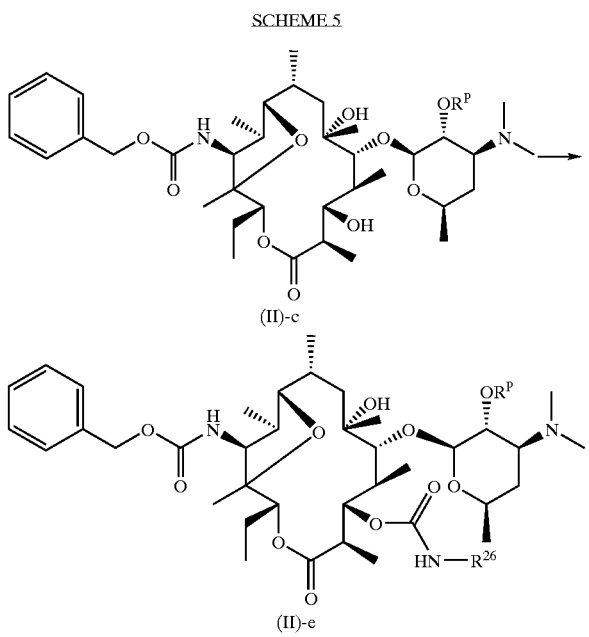

Compounds having formula (II)-c may be converted to compounds having formula (II)-e by reacting the former, a compound having formula $R^{26}NCO$, and 4-(N,N-dimethylamino)pyridine.

Examples of compounds having formula $R^{26}NCO$ include ethyl isocynante, isopropyl isocyanate, allyl isocyanate, cyclopentyl isocyanate, cyclohexyl isocyanate, phenyl isocyanate, 4-fluorobenzylisocyanate, 3,5-dichlorophenyl isocyanate, trans-2-phenylcyclopropyl isocyanate, 2-methoxyphenyl isocyanate, 2-ethylphenyl isocyanate, 3,4-dichlorophenyl isocyanate, and 1-naphthyl isocyanate.

The reaction is typically conducted at about 25° C. to about 150° C., over about 1 hour to about 4 days, in solvents such as toluene, benzene, xylene, dichloromethane, chloroform, tetrahydrofuran, and mixtures thereof.

Alternatively, compounds having formula (II)-c may be converted to compounds having formula (II)-e by (a) reacting the former, the carbonylating agent, and the second base, with or without 4-(N,N-dimethylamino)pyridine, and (b) reacting the product of step (a) and a compound having formula $H_2NR^{26}$ using the same reagents and under the same conditions described for the conversion of compounds having formula (I)-c to compounds having formula (I)-d in SCHEME 1.

Examples of amines having formula $H_2NR$ include ethylamine, propylamine, (prop-2-ynyl)amine, (prop-2-enyl)amine, phenylmethylamine, (3-fluorophenyl)methylamine, (2-fluorophenyl)methylamine, (4-methylphenyl)methylamine, (4-methoxyphenyl)methylamine, (pyridin-2-yl)methylamine, (pyridin-3-yl)methylamine, (pyridin-4-yl)methylamine, 2-(pyridin-2-yl)ethylamine, 2-(pyridin-3-yl)ethylamine, and 2-(pyridin-4-yl)ethylamine.

Compounds having formula (I), formula (I)-f, formula (I)-g, formula (II), formula (II)-f, and formula (II)-g, in which $R^P$ is acetyl or benzoyl, may be converted to compounds having formula (I), formula (I)-f, formula (I)-g, formula (II), formula (II)-f, and formula (II)-g, in which $R^2$ is hydrogen, by reacting the former and a deprotecting agent.

Examples of deprotecting agents include acids such as methanol, ethanol, acetic acid, and formic acid and bases such as lithium hydroxide, sodium hydroxide, potassium hydroxide, potassium carbonate, and ammonia.

The reaction is typically conducted at about 25° C. to about 70° C., over about 1 hour to about 72 hours, in solvents such as water, methanol, ethanol, and mixtures thereof.

Compound having formula (I) or (II), in which $R^3$ or $R^4$ is (phenylmethyl)OC(O)NH—, may be converted to compounds having formula (I) or (II), in which $R^3$ or $R^4$ is —$NH_2$, by reacting the former, a hydride source and a palladium catalyst.

Examples of hydride sources include cyclohexene, 1,4-cyclohexadiene, formic acid, hydrogen, and ammonium formate.

Examples of palladium catalysts include palladium black, palladium on carbon, and palladium hydroxide.

The reaction is typically conducted at about 25° C. to about 70° C., over about 2 hours to about 3 days, in solvents such as ethanol, isopropanol, ethyl acetate, and mixtures thereof.

The compounds and processes of this invention will be better understood in connection with the following examples.

EXAMPLE 1

This example was prepared as described in column 34, lines 34–41 of commonly-owned U.S. Pat. No. 5,288,709.

EXAMPLE 2

A solution of EXAMPLE 1 (14.9 g) in dichloromethane (100 mL) at 0° C. was treated with benzoic anhydride (6.79 g) and triethylamine (4.17 mL), stirred at 25° C. for 17 hours, and concentrated; and the concentrate was flash chromatographed on silica gel with 97:3:0.5 dichloromethane/methanol/ammonium hydroxide.

EXAMPLE 3

A solution of EXAMPLE 2 (820 mg), CDI (405 mg), DMAP (12.2 mg), and DBU (224 µL) in THF (10 mL) and DMF (3 mL) at 25° C. was stirred for 18 hours, treated with ethyl acetate, washed with water and saturated $NaHCO_3$, and dried ($Na_2SO_4$), filtered, and concentrated.

EXAMPLE 4

A solution of the EXAMPLE 3 concentrate and ethylenediamine (667 µL) in acetonitrile (10 mL) and water (1 mL) at 25° C. was stirred for 4 days and concentrated; and the concentrate was flash chromatographed on silica gel with 95:5:0.5 dichloromethane/methanol/ammonium hydroxide.

EXAMPLE 5

(1-(S or R),2R,5R,6S,7S,8R,9S,11R,12S,13S)-2-ethyl-9-hydroxy-1,5,7,9,11,13-hexamethyl-4,14-dioxo-8-((3,4,6-trideoxy-3-(dimethylamino)-β-D-xylo-hexopyranosyl)oxy)-3,15-dioxabicyclo(10.2.1)pentadec-6-yl 4-O-(((2-aminoethyl)amino)carbonyl)-2,6-dideoxy-3-C-methyl-3-O-methyl-α-L-ribo-hexopyranoside This example was prepared by substituting EXAMPLE 4 for EXAMPLE 7 in EXAMPLE 8.

EXAMPLE 6

A solution of EXAMPLE 3 (286 mg) and 1-(2-methoxyphenyl)ethanone (65 µL), in acetonitrile (2 mL) at 80° C. was stirred for 18 hours and concentrated.

EXAMPLE 7

A solution of the EXAMPLE 6 concentrate in methanol (2 mL) at 0° C. was treated with sodium cyanoborohydride (30 mg), stirred for 3 hours, acidified to pH 3 with 1M HCl, stirred for 15 minutes at 25° C., treated with 5% $Na_2CO_3$ until basic, and extracted with dichloromethane; and the extract was dried ($Na_2SO_4$), filtered, and concentrated.

EXAMPLE 8

(1-(S or R),2R,5R,6S,7S,8R,9S,11R,12S,13R,14S)-14-amino-2-ethyl-9-hydroxy-1,5,7,9,11,13-hexamethyl-4-oxo-8-((3,4,6-trideoxy-3-(dimethylamino)-β-D-xylo-hexopyranosyl)oxy-3,15-dioxabicyclo(10.2.1)pentadec-6-yl 2,6-dideoxy-4-O-(((2-((1-(2-methoxyphenyl)ethyl)amino)ethyl)amino)carbonyl)-3-C-methyl-3-O-methyl-α-L-ribo-hexopyranoside A solution of the EXAMPLE 7 concentrate in methanol (5 mL) was refluxed for 4 hours and concentrated; and the concentrate was flash chromatographed on silica gel with 95:5:0.5 dichloromethane/methanol/ammonium hydroxide.

EXAMPLE 9

This example was prepared by substituting quinoline-3-carboxaldehyde for 1-(2-methoxyphenyl)ethanone in EXAMPLE 6.

EXAMPLE 10

This example was prepared by substituting EXAMPLE 9 for in EXAMPLE 6 in EXAMPLE 7.

EXAMPLE 11

(1-(S or R),2R,5R,6S,7S,8R,9S,11R,12S,13S)-2-ethyl-9-hydroxy-1,5,7,9,11,13-hexamethyl-4,14-dioxo-8-((3,4,6-trideoxy-3-(dimethylamino)-β-D-xylo-hexopyranosyl)oxy)-3,15-dioxabicyclo(10.2.1)pentadec-6-yl 2,6-dideoxy-3-C-methyl-3-O-methyl-4-O-(((2-((quinolin-3-ylmethyl)amino)ethyl)amino)carbonyl)-α-L-ribo-hexopyranoside This example was prepared by substituting EXAMPLE 10 for EXAMPLE 7 in EXAMPLE 8.

EXAMPLE 12

This example was prepared by substituting quinoline-4-carboxaldehyde for 1-(2-methoxyphenyl)ethanone in EXAMPLE 6.

EXAMPLE 13

This example was prepared by substituting EXAMPLE 12 for in EXAMPLE 6 in EXAMPLE 7.

EXAMPLE 14

(1-(S or R),2R,5R,6S,7S,8R,9S,11R,12S,13S)-2-ethyl-9-hydroxy-1,5,7,9,11,13-hexamethyl-4,14-dioxo-8-((3,4,6-trideoxy-3-(dimethylamino)-β-D-xylo-hexopyranosyl)oxy)-3,15-dioxabicyclo(10.2.1)pentadec-6-yl 2,6-dideoxy-3-C-methyl-3-O-methyl-4-O-(((2-((quinolin-4-ylmethyl)amino)ethyl)amino)carbonyl)-α-L-ribo-hexopyranoside This example was prepared by substituting EXAMPLE 10 for EXAMPLE 7 in EXAMPLE 8.

EXAMPLE 15

This example was prepared by substituting pyridine-2-carboxaldehyde for 1-(2-methoxyphenyl)ethanone in EXAMPLE 6.

EXAMPLE 16

This example was prepared by substituting EXAMPLE 15 for in EXAMPLE 6 in EXAMPLE 7.

EXAMPLE 17

(1-(S or R),2R,5R,6S,7S,8R,9S,11R,12S,13S)-2-ethyl-9-hydroxy-1,5,7,9,11,13-hexamethyl-4,14-dioxo-8-((3,4,6-trideoxy-3-(dimethylamino)-β-D-xylo-hexopyranosyl)oxy)-3,15-dioxabicyclo(10.2.1)pentadec-6-yl 2,6-dideoxy-3-C-methyl-3-O-methyl-4-O-(((2-((pyridin-2-ylmethyl)amino)ethyl)amino)carbonyl)-α-L-ribo-hexopyranoside This example was prepared by substituting EXAMPLE 16 for EXAMPLE 7 in EXAMPLE 8.

EXAMPLE 18

A solution of EXAMPLE 1 (6.4 g), hydroxylamine hydrochloride (7.33 g), and triethylamine (8.62 mL) in ethanol (80 mL) at 70° C. was stirred for four days, cooled, and concentrated. The concentrate was dissolved in 5% $NaHCO_3$, adjusted to pH 10 with concentrated ammonium hydroxide, and extracted with dichloromethane. The extract was washed with water and 10% $NaHCO_3$ and dried ($Na_2SO_4$), filtered, and concentrated; and the concentrate was purified on silica gel with 97:3:0.5 to 95:5:0.5 dichloromethane/methanol/ammonium hydroxide.

EXAMPLE 19

A solution of EXAMPLE 18 (4.48 g) and ammonium acetate (23.51 g) in methanol (100 mL) at 0° C. was treated with 30% $TiCl_3$ in 2M HCl (5.23 mL), stirred for 1 hour, treated with sodium cyanoborohydride (1.92 g), stirred for 18 hours at 25° C., cooled to 0° C., treated with additional 30% $TiCl_3$ in 2M HCl (5.2 mL), stirred for another 18 hours at 25° C., and concentrated.

EXAMPLE 20

A solution of EXAMPLE 19 (3.93 g) and triethylamine (2.29 mL) in dichloromethane (50 mL) at 25° C. was treated with di-tert-butyl dicarbonate (1.32 g) in dichloromethane (10 mL), stirred for 1 hour at room temperature, diluted with dichloromethane, washed with water and saturated NaHCO$_3$, and dried (Na$_2$SO$_4$), filtered, and concentrated; and the concentrate was purified on silica gel with 97:3:0.5 dichloromethane/methanol/ammonium hydroxide.

EXAMPLE 21

A solution of EXAMPLE 20 (1.9 g) in dichloromethane (10 mL) at 0° C. was treated with benzoic anhydride (789 mg) and triethylamine (485 µL), stirred at 25° C. for 17 hours, and concentrated; and the concentrate was flash chromatographed on silica gel with 97:3:0.5 dichloromethane/methanol/ammonium hydroxide.

EXAMPLE 22

A solution of EXAMPLE 21 (185 mg), CDI (81 mg), DMAP (2.4 mg), and DBU (45 µL) in THF (2 mL) and DMF (0.6 mL) at 25° C. was stirred for 18 hours, treated with ethyl acetate, washed with water and saturated NaHCO$_3$, and dried (Na$_2$SO$_4$), filtered, and concentrated.

EXAMPLE 23

A solution of the EXAMPLE 22 concentrate and ethylenediamine (133 µL) in acetonitrile (10 mL) and water (1 mL) at 25° C. was stirred for 2 days and concentrated; and the concentrate was flash chromatographed on silica gel with 95:5:0.5 dichloromethane/methanol/ammonium hydroxide.

EXAMPLE 24

A solution of EXAMPLE 23 (182 mg) and pyridine-2-carboxaldehyde (29 µL) in acetonitrile (2 mL) at 80° C. was stirred for 18 hours and concentrated.

EXAMPLE 25

A solution of the EXAMPLE 24 concentrate in methanol (2 mL) at 0° C. was treated with sodium cyanoborohydride (19 mg), stirred for 3 hours, acidified to pH 3 with 1M HCl, stirred for 15 minutes at 25° C., made basic with 5% Na$_2$CO$_3$, and extracted with dichloromethane. The extract was dried (Na$_2$SO$_4$), filtered, and concentrated; and the concentrate was flash chromatographed on silica gel with 98:2:0.5 dichloromethane/methanol/ammonium hydroxide.

EXAMPLE 26

(1-(S or R),2R,5R,6S,7S,8R,9S,11R,12S,13R,14S)-14-amino-2-ethyl-9-hydroxy-1,5,7,9,11,13-hexamethyl-4-oxo-8-((3,4,6-trideoxy-3-(dimethylamino)-β-D-xylo-hexopyranosyl)oxy)-3,15-dioxabicyclo (10.2.1)pentadec-6-yl 2,6-dideoxy-3-C-methyl-3-O-methyl-4-O-(((2-((pyridin-2-ylmethyl)amino)ethyl) amino)carbonyl)-α-L-ribo-hexopyranoside A solution of EXAMPLE 25 (1.98 g) in methanol (5 mL), was refluxed for 4 hours and concentrated; and the concentrate was flash chromatographed on silica gel with 95:5:0.5 dichloromethane/methanol/ammonium hydroxide.

EXAMPLE 27

(1S,2R,4S,5R,6S,7S,8R,11R,12-(S or R),13S,14R)-13-amino-11-ethyl-4,7-dihydroxy-2,4,6,8,12,14-hexamethyl-9-oxo-10,15-dioxabicyclo(10.2.1)pentadec-5-yl 3,4,6-trideoxy-3-(dimethylamino)-β-D-xylo-hexopyranoside A solution of EXAMPLE 19 (3 g) and 1M HCl (15 mL) in ethanol (3 mL) and water (7 mL) was stirred at 25° C. for 36 hours, poured into 5% NaHCO$_3$ (100 mL), and extracted with chloroform; and the extract was dried (MgSO$_4$), filtered, and concentrated.

EXAMPLE 28 benzyl (1S,2R,4S,5R,6S,7S,8R,11R,12-(S or R),13S,14R)-11-ethyl-4,7-dihydroxy-2,4,6,8,12,14-hexamethyl-9-oxo-5-((3,4,6-trideoxy-3-(dimethylamino)-β-D-xylo-hexopyranosyl)oxy)-10,15-dioxabicyclo(10.2.1)pentadec-13-ylcarbamate A solution of EXAMPLE 27 (63.3 g) and CBZ-NOS (28.2 g) in dichloromethane (1L) was stirred at 25° C. for 48 hours, washed with 0.5M NaOH (100 mL), and dried (MgSO$_4$), filtered, and concentrated.

EXAMPLE 29

A solution of EXAMPLE 28 (78 g), triethylamine (22.8 g) and acetyl chloride (28.8 g) in dichloromethane (1 L) was stirred for 12 hours, washed with saturated NaHCO$_3$ and brine, and dried (MgSO$_4$), filtered, and concentrated; and the concentrate was flash chromatographed on silica gel with 97.5:2:0.5 dichloromethane/methanol/ammonium hydroxide.

EXAMPLE 30

A solution of EXAMPLE 29 (367 mg), isopropylisocyanate (64 µL), and DMAP (61 mg) in toluene (5 mL) was heated at 100° C. for 3 days and concentrated; and the concentrate was flash chromatographed on silica gel with 1:1 acetone/hexane.

EXAMPLE 31

(1-(S or R),2R,5R,6S,7S,8R,9S,11R,12S,13R,14S)-14-amino-2-ethyl-9-hydroxy-1,5,7,9,11,13-hexamethyl-4-oxo-8-((3,4,6-trideoxy-3-(dimethylamino)-β-D-xylo-hexopyranosyl)oxy)-3,15-dioxabicyclo (10.2.1)pentadec-6-yl isopropylcarbamate A solution of EXAMPLE 30, 10% palladium on carbon (50 mg), and ammonium formate (315 mg) in methanol (5 mL) was heated at reflux for 6 hours and cooled, filtered through diatomaceous earth (Celite®), and concentrated; and the concentrate was flash chromatographed on silica gel with 95:4.5:0.5 dichloromethane/methanol/ammonium hydroxide.

EXAMPLE 32

This example was prepared by substituting cyclopentylisocyanate for isopropylisocyanate in EXAMPLE 30.

EXAMPLE 33

(1-(S or R),2R,5R,6S,7S,8R,9S,11R,12S,13R,14S)-14-amino-2-ethyl-9-hydroxy-1,5,7,9,11,13-hexamethyl-4-oxo-8-((3,4,6-trideoxy-3-(dimethylamino)-β-D-xylo-hexopyranosyl)oxy)-3,15-dioxabicyclo(10.2.1)pentadec-6-yl cyclopentylcarbamate This example was prepared by substituting EXAMPLE 32 for EXAMPLE 30 in EXAMPLE 31.

EXAMPLE 34

This example was prepared by substituting cyclohexylisocyanate for isopropylisocyanate in EXAMPLE 30.

EXAMPLE 35

(1-(S or R),2R,5R,6S,7S,8R,9S,11R,12S,13R,14S)-14-amino-2-ethyl-9-hydroxy-1,5,7,9,11,13-hexamethyl-4-oxo-8-((3,4,6-trideoxy-3-(dimethylamino)-β-D-xylo-hexopyranosyl)oxy)-3,15-dioxabicyclo(10.2.1)pentadec-6-yl cyclohexylcarbamate This example was prepared by substituting EXAMPLE 34 for EXAMPLE 30 in EXAMPLE 31.

EXAMPLE 36

This example was prepared by substituting 4-fluorobenzylisocyanate for isopropylisocyanate in EXAMPLE 30.

EXAMPLE 37

(1-(S or R),2R,5R,6S,7S,8R,9S,11R,12S,13R,14S)-14-amino-2-ethyl-9-hydroxy-1,5,7,9,11,13-hexamethyl-4-oxo-8-((3,4,6-trideoxy-3-(dimethylamino)-β-D-xylo-hexopyranosyl)oxy)-3,15-dioxabicyclo(10.2.1)pentadec-6-yl 4-fluorobenzylcarbamate This example was prepared by substituting EXAMPLE 36 for EXAMPLE 30 in EXAMPLE 31.

EXAMPLE 38

This example was prepared by substituting 3,5-dichlorophenylisocyanate for isopropylisocyanate in EXAMPLE 30.

EXAMPLE 39

(1-(S or R),2R,5R,6S,7S,8R,9S,11R,12S,13R,14S)-14-amino-2-ethyl-9-hydroxy-1,5,7,9,11,13-hexamethyl-4-oxo-8-((3,4,6-trideoxy-3-(dimethylamino)-β-D-xylo-hexopyranosyl)oxy)-3,15-dioxabicyclo(10.2.1)pentadec-6-yl 3,5-dichlorophenylcarbamate This example was prepared by substituting EXAMPLE 38 for EXAMPLE 30 in EXAMPLE 31.

EXAMPLE 40 AND EXAMPLE 41

These examples were prepared by substituting trans-phenylcyclopropylisocyanate for isopropylisocyanate in EXAMPLE 30.

EXAMPLE 42 AND EXAMPLE 43

(1-(S or R),2R,5R,6S,7S,8R,9S,11R,12S,13R,14S)-14-amino-2-ethyl-9-hydroxy-1,5,7,9,11,13-hexamethyl-4-oxo-8-((3,4,6-trideoxy-3-(dimethylamino)-β-D-xylo-hexopyranosyl)oxy)-3,15-dioxabicyclo(10.2.1)pentadec-6-yl (1S,2R)-2-phenylcyclopropylcarbamate and (1-(S or R),2R,5R,6S,7S,8R,9S,11R,12S,13R,14S)-14-amino-2-ethyl-9-hydroxy-1,5,7,9,11,13-hexamethyl-4-oxo-8-((3,4,6-trideoxy-3-(dimethylamino)-β-D-xylo-hexopyranosyl)oxy)-3,15-dioxabicyclo(10.2.1)pentadec-6-yl (1R,2S)-2-phenylcyclopropylcarbamate (1:1)

These examples were prepared by substituting EXAMPLE 40 and EXAMPLE 41 for EXAMPLE 30 in EXAMPLE 31.

EXAMPLE 44

This example was prepared by substituting allylisocyanate for isopropylisocyanate in EXAMPLE 30.

EXAMPLE 45

(1-(S or R),2R,5R,6S,7S,8R,9S,11R,12S,13R,14S)-14-amino-2-ethyl-9-hydroxy-1,5,7,9,11,13-hexamethyl-4-oxo-8-((3,4,6-trideoxy-3-(dimethylamino)-β-D-xylo-hexopyranosyl)oxy)-3,15-dioxabicyclo(10.2.1)pentadec-6-yl propylcarbamate This example was prepared by substituting EXAMPLE 44 for EXAMPLE 30 in EXAMPLE 31.

EXAMPLE 46

A suspension of tris(dibenzylideneacetone)dipalladium (0) (4 mg) and dppe (4 mg) in THF (15 mL) was treated with EXAMPLE 30 (500 mg) and tert-butyl allyl carbonate (70 mg), refluxed for 5 hours, treated with more tris(dibenzylideneacetone)dipalladium(0) (4 mg) and tert-butyl allyl carbonate (35 g), refluxed for another 5 hours and cooled, treated with ethyl acetate, washed with saturated NaHCO$_3$, water, and brine, and dried (MgSO$_4$), filtered, and concentrated; and the concentrate was flash chromatographed on silica gel with 85:15:1.5 hexanes/acetone/triethylamine.

EXAMPLE 47

A solution of 4-fluorophenyl oxime (400 g) N-chlorosuccinamide (380 mg) and pyridine (catalytic) in dichloromethane (20 mL) was stirred for 5 hours, added to a solution of EXAMPLE 46 (230 mg) in dichloromethane (5 mL), treated with triethylamine (300 mg), stirred for 12 hours, treated with ethyl acetate, washed with saturated NaHCO$_3$, water, and brine, and dried (MgSO$_4$), filtered, and concentrated; and the concentrate was flash chromatographed on silica gel with 70:30:1.5 hexane/acetone/triethylamine.

EXAMPLE 48

(1S,2R,4S,5R,6S,7S,8R,11R,12-(S or R),13S,14R)-13-amino-11-ethyl-7-((3-(4-fluorophenyl)-4,5-dihydroisoxazol-5-yl)methoxy)-4-hydroxy-2,4,6,8,12,14-hexamethyl-9-oxo-10,15-dioxabicyclo(10.2.1)pentadec-5-yl 3,4,6-trideoxy-3-(dimethylamino)-β-D-xylo-hexopyranoside A solution of EXAMPLE 47 (220 mg) and 10% palladium on carbon (30 mg) in methanol (10 mL) was stirred under hydrogen at 25° C. for 12 hours, filtered through diatomaceous earth (Celite®), and concentrated; and the concentrate was flash chromatographed on silica gel with 97.5:2.5:1 to 95:5:1 dichloromethane/methanol/ammonium hydroxide.

EXAMPLE 49

This example was prepared by substituting 2-pyridyl oxime for 4-fluorophenyl oxime in EXAMPLE 47.

EXAMPLE 50

(1S,2R,4S,5R,6S,7S,8R,11R,12-(S or R),13S,14R)-13-amino-11-ethyl-4-hydroxy-2,4,6,8,12,14-hexamethyl-9-oxo-7-((3-pyridin-2-yl-4,5-dihydroisoxazol-5-yl)methoxy)-10,15-dioxabicyclo(10.2.1)pentadec-5-yl 3,4,6-trideoxy-3-(dimethylamino)-β-D-xylo-hexopyranoside This example was prepared by substituting EXAMPLE 49 for EXAMPLE 47 in EXAMPLE 48.

EXAMPLE 51

A solution of EXAMPLE 29 (5 g) and CDI (2.2 g) in 1:1 dichloromethane/THF (100 mL) was heated at reflux for 12 hours, treated with ethyl acetate, washed with saturated NaHCO₃, water, and brine, and dried (MgSO₄), filtered, and concentrated; and the concentrate was purified by flash chromatography on silica gel with 70:30:1.5 hexane/acetone/triethylamine.

EXAMPLE 52

A solution of EXAMPLE 51 (200 g) and 2-(aminomethyl)pyridine (400 g) in 5:1 acetonitrile/water (6 mL) was stirred for 12 hours, treated with ethyl acetate, washed with saturated NaHCO₃, water, and brine, and dried (MgSO₄), filtered, and concentrated; and the concentrate was flash chromatographed on silica gel with 50:50:1.5 to 70:30:1.5 acetone/hexanes/triethylamine.

EXAMPLE 53

(1-(S or R),2R,5R,6S,7S,8R,9S,11R,12S,13R,14S)-14-amino-2-ethyl-9-hydroxy-1,5,7,9,11,13-hexamethyl-4-oxo-8-((3,4,6-trideoxy-3-(dimethylamino)-β-D-xylo-hexopyranosyl)oxy)-3,15-dioxabicyclo(10.2.1)pentadec-6-yl pyridin-2-ylmethylcarbamate A solution of EXAMPLE 52 and 10% palladium on carbon in methanol (10 mL) at 25° C. was stirred under hydrogen for 12 hours, filtered through diatomaceous earth (Celite®), and concentrated.

EXAMPLE 54

This example was prepared by substituting 2-(2-aminoethyl)pyridine for 2-(aminomethyl)pyridine in EXAMPLE 52.

EXAMPLE 55

(1-(S or R),2R,5R,6S,7S,8R,9S,11R,12S,13R,14S)-14-amino-2-ethyl-9-hydroxy-1,5,7,9,11,13-hexamethyl-4-oxo-8-((3,4,6-trideoxy- 3-(dimethylamino)-β-D-xylo-hexopyranosyl)oxy)-3,15-dioxabicyclo(10.2.1)pentadec-6-yl 2-pyridin-4-ylethylcarbamate This example was prepared by substituting EXAMPLE 54 for EXAMPLE 52 in EXAMPLE 53.

EXAMPLE 56

(1S,2R,4S,5R,6S,7S,8R,11R,12-(S or R),13S,14R)-13-amino-11-ethyl-4-hydroxy-2,4,6,8,12,14-hexamethyl-9-oxo-7-propoxy-10,15-dioxabicyclo(10.2.1)pentadec-5-yl 3,4,6-trideoxy-3-(dimethylamino)-β-D-xylo-hexopyranoside A suspension of EXAMPLE 46 (200 mg) and 10% palladium on carbon (20 mg) in methanol (10 mL) at 25° C. was stirred for 12 hours, filtered through diatomaceous earth (Celite®), and concentrated.

EXAMPLE 57

This example was prepared by substituting phenyl oxime for 4-fluorophenyl oxime in EXAMPLE 47.

EXAMPLE 58

(1S,2R,4S,5R,6S,7S,8R,11R,12-(S or R),13S,14R)-13-amino-11-ethyl-4-hydroxy-2,4,6,8,12,14-hexamethyl-9-oxo-7-((3-phenyl-4,5-dihydroisoxazol-5-yl)methoxy)-10,15-dioxabicyclo(10.2.1)pentadec-5-yl 3,4,6-trideoxy-3-(dimethylamino)-β-D-xylo-hexopyranoside This example was prepared by substituting EXAMPLE 57 for EXAMPLE 52 in EXAMPLE 53.

EXAMPLE 59

This example was prepared by substituting EXAMPLE 44 and phenyl oxime for EXAMPLE 46 and 4-fluorophenyl oxime, respectively, in EXAMPLE 47.

EXAMPLE 60

(1-(S or R),2R,5R,6S,7S,8R,9S,11R,12S,13R,14S)-14-amino-2-ethyl-9-hydroxy-1,5,7,9,11,13-hexamethyl-4-oxo-8-((3,4,6-trideoxy-3-(dimethylamino)-β-D-xylo-hexopyranosyl)oxy)-3,15-dioxabicyclo(10.2.1)pentadec-6-yl (3-phenyl-4,5-dihydroisoxazol-5-yl)methylcarbamate This example was prepared by substituting EXAMPLE 59 for EXAMPLE 52 in EXAMPLE 53.

EXAMPLE 61

This example was prepared by substituting 4-(aminomethyl)pyridine for 2-(aminomethyl)pyridine in EXAMPLE 52.

EXAMPLE 62

(1-(S or R),2R,5R,6S,7S,8R,9S,11R,12S,13R,14S)-14-amino-2-ethyl-9-hydroxy-1,5,7,9,11,13-hexamethyl-4-oxo-8-((3,4,6-trideoxy-3-(dimethylamino)-β-D-xylo-hexopyranosyl)oxy)-3,15-dioxabicyclo(10.2.1)pentadec-6-yl pyridin-4-ylmethylcarbamate This example was prepared by substituting EXAMPLE 61 for EXAMPLE 52 in EXAMPLE 53.

EXAMPLE 63

This example was prepared by substituting 3-(aminomethyl)pyridine for 2-(aminomethyl)pyridine in EXAMPLE 52.

EXAMPLE 64

(1-(S or R),2R,5R,6S,7S,8R,9S,11R,12S,13R,14S)-14-amino-2-ethyl-9-hydroxy-1,5,7,9,11,13-hexamethyl-4-oxo-8-((3,4,6-trideoxy-3-(dimethylamino)-β-D-xylo-hexopyranosyl)oxy)-3,15-dioxabicyclo(10.2.1)pentadec-6-yl pyridin-3-ylmethylcarbamate This example was prepared by substituting EXAMPLE 63 for EXAMPLE 52 in EXAMPLE 53.

EXAMPLE 65

A solution of EXAMPLE 30 (0.5 g), 2-pyridylacetic acid (180 mg), DIEA (120 mg), EDCI (200 mg), and DMAP (catalytic) in dichloromethane (20 mL) was stirred for 12 hours, diluted with ethyl acetate, washed with saturated NaHCO$_3$, water, and brine, and dried (MgSO$_4$), filtered, and concentrated.

EXAMPLE 66

(1-(S or R),2R,5R,6S,7S,8R,9S,11R,12S,13R,14S)-14-amino-2-ethyl-9-hydroxy-1,5,7,9,11,13-hexamethyl-4-oxo-8-((3,4,6-trideoxy-3-(dimethylamino)-β-D-xylo-hexopyranosyl)oxy)-3,15-dioxabicyclo(10.2.1)pentadec-6-yl pyridin-2-ylacetate;

A solution of EXAMPLE 65 and 10% palladium on carbon (50 mg) in methanol (10 mL) at 25° C. was stirred under hydrogen at 25° C. for 12 hours, filtered through diatomaceous earth (Celite®), and concentrated; and the concentrate was flash chromatographed on silica gel with 95:5:1 dichloromethane/methanol/ammonium hydroxide.

EXAMPLE 67

This example was prepared by substituting 3-(2-aminoethyl)pyridine for 2-(aminomethyl)pyridine in EXAMPLE 52.

EXAMPLE 68

(1-(S or R),2R,5R,6S,7S,8R,9S,11R,12S,13R,14S)-14-amino-2-ethyl-9-hydroxy-1,5,7,9,11,13-hexamethyl-4-oxo-8-((3,4,6-trideoxy-3-(dimethylamino)-β-D-xylo-hexopyranosyl)oxy)-3,15-dioxabicyclo(10.2.1)pentadec-6-yl 2-pyridin-3-ylethylcarbamate This example was prepared by substituting EXAMPLE 67 for EXAMPLE 65 in EXAMPLE 66.

EXAMPLE 69

This example was prepared by substituting 2-(2-aminoethyl)pyridine for 2-(aminomethyl)pyridine in EXAMPLE 52.

EXAMPLE 70

(1-(S or R),2R,5R,6S,7S,8R,9S,11R,12S,13R,14S)-14-amino-2-ethyl-9-hydroxy-1,5,7,9,11,13-hexamethyl-4-oxo-8-((3,4,6-trideoxy-3-(dimethylamino)-β-D-xylo-hexopyranosyl)oxy)-3,15-dioxabicyclo(10.2.1)pentadec-6-yl 2-pyridin-2-ylethylcarbamate This example was prepared by substituting EXAMPLE 69 for EXAMPLE 65 in EXAMPLE 66.

EXAMPLE 71

This example was prepared by substituting 3-fluorobenzylisocyanate for isopropylisocyanate in EXAMPLE 30.

EXAMPLE 72

(1-(S or R),2R,5R,6S,7S,8R,9S,11R,12S,13R,14S)-14-amino-2-ethyl-9-hydroxy-1,5,7,9,11,13-hexamethyl-4-oxo-8-((3,4,6-trideoxy-3-(dimethylamino)-β-D-xylo-hexopyranosyl)oxy)-3,15-dioxabicyclo(10.2.1)pentadec-6-yl 3-fluorobenzylcarbamate This example was prepared by substituting EXAMPLE 71 for EXAMPLE 65 in EXAMPLE 66.

EXAMPLE 73

This example was prepared by substituting 2-fluorobenzylisocyanate for isopropylisocyanate in EXAMPLE 30.

EXAMPLE 74

(1-(S or R),2R,5R,6S,7S,8R,9S,11R,12S,13R,14S)-14-amino-2-ethyl-9-hydroxy-1,5,7,9,11,13-hexamethyl-4-oxo-8-((3,4,6-trideoxy-3-(dimethylamino)-β-D-xylo-hexopyranosyl)oxy)-3,15-dioxabicyclo(10.2.1)pentadec-6-yl 2-fluorobenzylcarbamate This example was prepared by substituting EXAMPLE 73 for EXAMPLE 65 in EXAMPLE 66.

EXAMPLE 75

This example was prepared by substituting 4-methylbenzylisocyanate for isopropylisocyanate in EXAMPLE 30.

EXAMPLE 76

(1-(S or R),2R,5R,6S,7S,8R,9S,11R,12S,13R,14S)-14-amino-2-ethyl-9-hydroxy-1,5,7,9,11,13-hexamethyl-4-oxo-8-((3,4,6-trideoxy-3-(dimethylamino)-β-D-xylo-hexopyranosyl)oxy)-3,15-dioxabicyclo(10.2.1)pentadec-6-yl 4-methylbenzylcarbamate This example was prepared by substituting EXAMPLE 75 for EXAMPLE 65 in EXAMPLE 66.

EXAMPLE 77

This example was prepared by substituting 3-pyridylacetic acid for 2-pydidylacetic acid in EXAMPLE 65.

EXAMPLE 78

(1-(S or R),2R,5R,6S,7S,8R,9S,11R,12S,13R,14S)-14-amino-2-ethyl-9-hydroxy-1,5,7,9,11,13-hexamethyl-4-oxo-8-((3,4,6-trideoxy-3-(dimethylamino)-β-D-xylo-hexopyranosyl)oxy)-3,15-dioxabicyclo(10.2.1)pentadec-6-yl 3-pyridin-3-ylpropanoate This example was prepared by substituting EXAMPLE 77 for EXAMPLE 65 in EXAMPLE 66.

EXAMPLE 79

This example was prepared by substituting 4-methoxybenzylisocyanate for isopropylisocyanate in EXAMPLE 4.

EXAMPLE 80

(1-(S or R),2R,5R,6S,7S,8R,9S,11R,12S,13R,14S)-14-amino-2-ethyl-9-hydroxy-1,5,7,9,11,13-hexamethyl-4-oxo-8-((3,4,6-trideoxy-3-(dimethylamino)-β-D-xylo-hexopyranosyl)oxy)-3,15-dioxabicyclo(10.2.1)pentadec-6-yl 4-methoxybenzylcarbamate This example was prepared by substituting EXAMPLE 79 for EXAMPLE 65 in EXAMPLE 66.

EXAMPLE 81

This example was prepared by substituting benzylisocyanate for isopropylisocyanate in EXAMPLE 4.

EXAMPLE 82

(1-(S or R),2R,5R,6S,7S,8R,9S,11R,12S,13R,14S)-14-amino-2-ethyl-9-hydroxy-1,5,7,9,11,13-hexamethyl-4-oxo-8-((3,4,6-trideoxy-3-(dimethylamino)-β-D-xylo-hexopyranosyl)oxy)-3,15-dioxabicyclo(10.2.1)pentadec-6-yl benzylcarbamate This example was prepared by substituting EXAMPLE 81 for EXAMPLE 65 in EXAMPLE 66.

Spectral Data

EXAMPLE 5

$^{13}$C NMR (CDCl$_3$) δ 217.6, 177.0, 157.1, 105.1, 98.2, 84.0, 82.7, 80.1, 80.0, 78.7, 78.3, 73.7, 73.6, 73.2, 70.7, 69.1, 64.6, 63.5, 55.2, 52.3, 48.9, 47.8, 47.7, 47.6, 46.6, 43.5, 42.9, 41.2, 40.4, 36.8, 35.5, 29.4, 26.6, 22.5, 22.2, 21.2, 21.0, 20.9, 19.9, 19.4, 17.2, 15.8, 13.5, 10.8, 10.3.

EXAMPLE 8

NMR (CDCl$_3$) δ 217.6, 177.0, 157.1, 156.4, 132.9, 128.1, 127.6, 126.9, 120.7, 110.6, 105.2, 105.1, 98.2, 84.0, 82.7, 80.1, 80.0, 78.7, 78.3, 73.7, 73.6, 73.2, 70.7, 69.1, 64.6, 63.5, 55.2, 52.3, 49.7, 47.7, 47.6, 46.6, 43.5, 42.9, 41.2, 40.4, 36.8, 35.5, 29.4, 26.6, 22.5, 22.2, 21.2, 21.0, 20.9, 19.9, 19.4, 17.2, 15.8, 13.5, 10.8, 10.3.

EXAMPLE 11

$^{13}$C NMR (CDCl$_3$) δ 217.6, 177.0, 156.4, 151.3, 147.5, 138.9, 134.4, 132.6, 129.2, 129.1, 128.1, 127.9, 127.5, 126.7, 105.3, 98.2, 87.9, 86.9, 84.0, 93.2, 82.8, 80.3, 79.5, 78.8, 78.3, 73.6, 73.2, 70.7, 70.4, 69.3, 69.1, 64.6, 63.5, 62.8, 51.1, 49.7, 49.6, 49.1, 48.7, 47.8, 46.1, 43.3, 42.8, 40.9, 40.3, 36.9, 35.4, 30.8, 29.6, 29.4, 26.6, 24.3, 23.2, 22.5, 21.2, 20.9, 19.9, 19.4, 17.2, 16.8, 15.9, 13.9, 13.5, 12.1, 11.0, 10.8, 10.3.

EXAMPLE 14

$^{13}$C NMR (CDCl$_3$) δ 217.6, 176.9, 156.4, 150.2, 148.2, 145.2, 130.2, 129.1, 128.1, 126.9, 126.6, 123.1, 119.7, 105.3, 98.2, 88.8, 88.0, 86.9, 84.0, 83.2, 82.8, 80.3, 79.5, 78.9, 78.4, 73.5, 73.2, 70.7, 69.3, 69.1, 65.3, 64.5, 63.5, 62.8, 49.7, 49.2, 47.8, 43.5, 43.3, 42.8, 40.9, 40.3, 37.0, 35.4, 30.8, 29.6, 29.4, 26.5, 23.2, 22.5, 21.1, 20.9, 19.8, 19.4, 17.2, 16.0, 13.9, 13.5, 12.1, 10.8, 10.3.

EXAMPLE 17

$^{13}$C NMR (CDCl$_3$) δ 217.6, 177.0, 159.4, 156.4, 149.3, 138.9, 136.4, 128.2, 122.2, 122.0, 105.3, 105.1, 98.2, 88.8, 87.7, 86.9, 84.0, 82.8, 80.1, 78.7, 78.3, 73.6, 73.2, 70.7, 70.4, 69.3, 69.1, 63.6, 62.8, 54.6, 49.7, 49.1, 48.5, 47.7, 46.1, 43.5, 42.8, 40.9, 40.4, 36.9, 35.5, 30.8, 29.6, 29.4, 26.5, 24.3, 23.2, 22.6, 21.2, 20.9, 19.9, 19.4, 17.2, 16.8, 15.8, 15.6, 13.5, 12.1, 11.0, 10.8, 10.3.

EXAMPLE 26

$^{1}$H NMR (CDCl$_3$) δ 8.64 (m, 1H), 7.80 (m, 1H), 7.25 (m, 1H), 7.17 (m, 1H), 5.46 (m, 1H), 5.09 (m, 1H), 4.88 (m, 1H), 4.56 (m, 1H), 4.43–4.36 (m, 1H), 3.89 (m, 1H), 3.60–3.15 (m, 11H), 2.80 (m, 2H), 2.56 (m, 1H), 2.45–2.05 (m, 9H), 1.70–1.48 (m, 11H), 1.48–1.24 (m, 3H), 1.18–1.06 (m, 11H), 1.02 (m, 6H), 0.85 (m, 6H).

EXAMPLE 27

$^{13}$C NMR (CDCl$_3$) δ 176.2, 106.1, 93.9, 88.0, 83.6, 78.5, 76.5, 74.2, 70.4, 69.8, 65.3, 55.4, 45.0, 40.2, 38.2, 36.8, 31.4, 28.0, 27.6, 23.6, 23.0, 21.0, 18.0, 15.2, 14.8, 11.0, 7.8.

EXAMPLE 28

$^{13}$C NMR (CDCl$_3$) δ 176.5, 155.7, 136.3, 128.5, 128.2, 128.0, 106.1, 94.6, 88.6, 83.1, 78.5, 76.2, 74.2, 70.4, 69.6, 67.0, 65.2, 55.6, 45.2, 40.2, 38.6, 36.6, 32.3, 28.0, 27.8, 23.2, 23.0, 21.0, 19.6, 15.4, 14.6, 10.7, 7.6.

EXAMPLE 33

$^{13}$C NMR (CDCl$_3$) δ 174.3, 155.6, 104.1, 86.6, 85.5, 84.4, 78.6, 77.4, 73.9, 70.5, 69.4, 65.9, 54.4, 44.1, 40.2, 37.2, 36.1, 34.4, 33.6, 33.4, 28.6, 28.5, 25.3, 24.1, 23.7, 23.5, 21.1, 20.5, 16.8, 15.5, 14.4, 10.8, 9.4.

EXAMPLE 35

$^{13}$C NMR (CDCl$_3$) δ 174.2, 155.4, 104.1, 86.5, 85.7, 84.3, 78.3, 77.4, 73.9, 70.5, 69.3, 65.8, 54.4, 49.6, 44.1, 40.2, 37.2, 36.1, 34.4, 33.8, 33.6, 33.3, 28.7, 28.5, 25.4, 25.3, 24.7, 24.6, 24.0, 21.1, 20.5, 16.8, 15.4, 14.5, 10.9, 9.4.

EXAMPLE 37

$^{13}$C NMR (CDCl$_3$) δ 174.3, 163.5, 156.3, 134.8, 129.3, 129.2, 115.3, 115.1, 103.6, 86.4, 85.1, 84.4, 78.9, 77.4, 74.1, 74.0, 70.5, 69.1, 65.2, 54.2, 43.9, 40.1, 37.0, 36.0, 34.1, 28.7, 28.4, 25.1, 24.0, 20.8, 20.4, 16.7, 15.2, 14.4, 10.8, 9.3.

EXAMPLE 39

$^{13}$C NMR (CDCl$_3$) δ 174.0, 153.1, 138.2, 128.9, 123.0, 118.2, 104.1, 86.6, 85.7, 84.3, 79.5, 77.5, 74.1, 70.4, 69.3, 65.7, 54.4, 47.5, 43.7, 40.1, 37.2, 36.1, 34.3, 28.6, 28.3, 25.3, 24.0, 20.9, 20.5, 16.8, 15.5, 14.5, 10.9, 9.4.

EXAMPLE 42 AND EXAMPLE 43

$^{13}$C NMR (CDCl$_3$) δ two sets of peaks at 174.2, 155.3, 137.9, 129.4, 128.3, 126.4, 104.0, 86.5, 85.3, 84.3, 78.4, 77.4, 73.9, 70.5, 69.4, 65.8, 54.4, 47.9, 44.2, 42.9, 40.2, 37.2, 36.1, 34.3, 28.6, 25.3, 24.0, 21.1, 20.5, 16.8, 15.4, 14.7, 10.8, 9.5.

EXAMPLE 45

$^{13}$C NMR (CDCl$_3$) δ 174.2, 156.2, 104.2, 86.6, 85.6, 84.4, 78.6, 77.4, 74.0, 70.5, 69.4, 65.9, 54.5, 44.2, 42.7, 40.3, 37.3, 36.2, 34.4, 29.7, 28.8, 28.6, 25.4, 24.1, 23.3, 21.1, 20.6, 16.9, 15.5, 14.6, 11.3, 10.9, 9.5.

EXAMPLE 48

$^{13}$C NMR (CDCl$_3$) δ 175.8, 164.7, 162.7, 155.2, 128.6, 128.5, 115.9, 115.8, 115.7, 103.3, 102.3, 86.7, 85.1, 84.7, 84.5, 84.4, 80.1, 80.0, 75.0, 74.4, 74.3, 70.8, 70.9, 69.3, 69.0, 65.5, 65.2, 54.4, 45.4, 40.3, 40.2, 38.8, 38.7, 37.6, 36.8, 36.1, 33.9, 29.7, 28.9, 28.7, 25.6, 24.0, 21.2, 21.0, 20.6, 16.8, 15.6, 15.0, 11.0, 9.1, 8.9.

EXAMPLE 50

$^{13}$C NMR (CDCl$_3$) δ 175.9, 175.8, 158.1, 149.6, 149.5, 149.3, 149.2, 136.3, 136.2, 124.1, 124.0, 121.7, 121.6, 103.2, 102.5, 86.7, 84.9, 84.7, 84.3, 84.2, 83.9, 80.8, 80.7, 75.0, 74.4, 71.0, 70.9, 69.2, 68.9, 65.4, 65.1, 54.3, 45.4, 40.3, 38.7, 37.0, 36.3, 36.1, 34.0, 33.9, 29.7, 29.1, 28.8, 28.7, 28.6, 25.6, 25.5, 24.0, 21.2, 20.6, 16.8, 15.5, 15.0, 10.9, 8.9, 8.8.

EXAMPLE 53

$^{13}$C NMR (CDCl$_3$) δ 174.3, 157.1, 156.3, 149.1, 136.7, 122.3, 121.8, 103.9, 86.6, 85.0, 84.4, 79.0, 76.7, 74.0, 70.6, 69.3, 65.6, 54.5, 46.1, 44.1, 40.3, 40.2, 37.3, 36.2, 34.4, 29.7, 28.8, 28.6, 25.3, 24.1, 21.1, 20.6, 16.8, 15.4, 14.6, 10.9, 9.4.

EXAMPLE 55

$^{13}$C NMR (CDCl$_3$) δ 174.2, 156.1, 150.1, 149.9, 147.8, 124.1, 123.5, 104.2, 86.6, 85.5, 84.4, 78.8, 74.0, 70.6, 69.5, 65.9, 54.5, 44.1, 1.2, 40.3, 37.4, 36.2, 35.6, 34.5, 29.6, 29.2, 28.8, 28.6, 25.4, 24.0, 21.1, 20.5, 16.9, 15.4, 14.7, 10.9, 9.5.

EXAMPLE 56

$^{13}$C NMR (CDCl$_3$) δ 176.0, 101.6, 87.0, 84.7, 83.5, 77.3, 75.7, 74.5, 73.6, 68.8, 62.9, 60.2, 45.2, 40.2. 38.1, 36.6, 35.9, 33.8, 33.2, 32.4, 28.5, 25.4, 23.8, 23.7, 20.8, 20.7, 17.2, 15.1, 14.6, 11.0, 10.7, 9.0.

EXAMPLE 58

$^{13}$C NMR (CDCl$_3$) δ 176.0, 130.1, 128.0, 126.2, 126.1, 102.5, 86.6, 84.7, 79.9, 79.8, 74.3, 74.0, 70.8, 70.7, 68.9, 65.4, 65.3, 54.3, 45.4, 40.3 38.6, 36.7, 36.0. 33.8, 2937, 29.6, 28.7, 28.6, 25.5, 25.4, 23.9, 21.1. 20.6, 16.8, 16.7, 14.9, 14.8, 10.9, 9.0.

EXAMPLE 60

$^{13}$C NMR (CDCl$_3$) δ 174.23, 156.2, 130.2, 129.6, 128.7, 128.6, 126.6, 126.5, 104.2, 86.6, 86.5, 85.7, 85.6, 84.4, 84.3, 79.8, 79.7, 79.0, 76.8, 73.9, 73.8, 70.6, 69.3, 65.56, 5435, 54.4, 44.2, 44.0, 43.9, 40.2, 40.1, 37.8, 37.2, 36.2, 36.1, 34.5, 34.8, 29.7, 29.6, 28.9, 28.6, 25.3, 24.0, 21.1, 21.0, 20.6, 20.5, 17.0, 16.9, 15.4, 14.6, 14.1, 10.9, 9.4, 9.3.

EXAMPLE 62

$^{13}$C NMR (CDCl$_3$) δ 174.0, 150.02, 147.2, 122.2, 104.2, 86.6, 85.6, 84.3, 79.5, 74.0, 70.56, 69.41, 65.8, 54.5, 44.1, 40.32, 37.5, 36.1, 28.6, 28.5, 24.0, 21.12 21.1, 20.5, 16.8, 15.5, 14.7, 10.9, 9.6.

EXAMPLE 64

$^{13}$C NMR (CDCl$_3$) δ 174.2, 149.0, 148.9, 123.0, 104.2, 86.6, 85.7, 84.3, 74.0, 70.5, 69.4, 65.7, 54.5, 44.1, 42.6, 40.3, 37.3, 36.1, 28.6, 28.5, 25.3, 24.0, 21.1, 20.5, 16.9, 15.5, 14.6, 10.9, 9.5.

EXAMPLE 66

$^{13}$C NMR (CDCl$_3$) δ 174.1, 169.6, 154.5, 149.2, 136.4, 124.2, 122.0, 104.3, 86.5, 85.2, 84.3, 79.0, 74.1, 70.7, 69.3, 65.5, 54.4, 43.9, 40.3, 37.5, 36.1, 34.0, 28.6, 25.3, 23.9, 21.1, 20.6, 16.8, 15.5, 14.9, 10.9, 9.4.

EXAMPLE 68

$^{13}$C NMR (CDCl$_3$) δ 174.3, 156.1, 150.1, 148.0, 136.3, 123.5, 104.2, 86.6, 85.5, 84.4, 78.8, 74.0, 70.6, 69.5, 35.8, 54.5, 44.1, 41.9, 40.3, 37.4, 36.2, 34.5, 33.5, 29.6, 28.8, 25.4, 24.0, 21.1, 20.5, 16.9, 15.4, 14.7, 10.9, 9.5.

EXAMPLE 70

$^{13}$C NMR (CDCl$_3$) δ 176.3, 165.1, 149.3, 144.0, 136.3, 116.5, 110.2, 107.2, 86.6, 85.5, 84.4, 78.8, 74.0, 70.6, 69.5, 35.8, 51.5, 44.1, 41.9, 40.3, 37.4, 36.2, 34.5, 33.5, 29.6, 28.6, 27.7, 25.4, 24.0, 20.9, 20.5, 16.9, 15.4, 14.7, 10.9, 9.5.

EXAMPLE 72

$^{13}$C NMR (CDCl$_3$) δ 174.2, 163.2, 161.7, 156.3, 130.2, 130.1, 123.1, 114.3, 114.2, 104.2, 86.6, 85.5, 54.4, 79.3, 76.7, 74.0, 70.6, 69.4, 65.7, 54.6, 44.6, 44.1, 41.8, 40.3, 3838, 37.3, 36.2, 34.4, 29.7, 28.6, 27.1, 25.4, 24.1, 21.1, 20.6, 16.9, 15.5, 14.6, 10.9, 9.5.

EXAMPLE 74

$^{13}$C NMR (CDCl$_3$) δ 174.2, 161.9, 160.0, 156.1, 130.3, 129.3, 129.2, 125.8, 125.6, 124.2, 115.3, 115.1, 103.8, 86.5, 85.1, 84.3, 79.2, 73.9, 70.4, 69.2, 65.6, 54.4, 44.0, 40.3, 39.2, 37.0, 36.1, 34.2, 29.6, 28.6, 28.5, 25.3, 24.0, 21.1, 20.6, 16.7, 15.5, 14.6, 10.9, 9.4.

EXAMPLE 76

$^{13}$C NMR (CDCl$_3$) δ 174.4, 156.5, 136.7, 135.6, 129.0, 127.4, 103.3, 86.3, 84.6, 84.4, 78.6, 76.7, 74.23, 74.1, 70.5, 68.9, 64.8, 54.0, 48.9, 48.8, 48.6, 44.5, 44.4, 43.9, 40.0, 36.9, 35.9, 33.9, 29.0, 28.3, 24.9, 23.98, 20.7, 20.2, 16.6, 15.0, 14.2, 10.7, 9.0.

EXAMPLE 78

$^{13}$C NMR (CDCl$_3$) δ 174.2, 171.2, 149.8, 147.9, 135.9, 123.4, 104.6, 86.5, 85.8, 78.6, 74.1, 70.4, 69.6, 65.9, 54.4, 43.7, 40.3, 37.5, 36.2, 35.4, 34.1, 28.6, 28.4, 25.4, 24.0, 21.2, 20.6, 16.8, 15.5, 14.9, 10.9, 9.6, 5.1.

EXAMPLE 80

$^{13}$C NMR (CDCl$_3$) δ 174.3, 158.9, 156.1, 130.9, 129.0, 113.9, 103.9, 86.5, 85.4, 84.3, 79.0, 77.4, 74.0, 70.5, 69.2, 65.6, 55.2, 54.4, 44.5, 44.1, 40.3, 37.2, 36.1, 34.3, 28.5, 25.3, 24.0, 21.1, 20.5, 16.8, 15.5, 14.6, 10.9, 9.5.

EXAMPLE 82

$^{13}$C NMR (CDCl$_3$) δ 174.2, 156.2, 138.8, 128.6, 127.6, 127.4, 104.0, 86.6, 85.4, 84.4, 79.1, 74.0, 70.6, 69.3, 65.7, 54.5, 45.1, 44.1, 40.3, 37.3, 36.1, 34.4, 28.7, 28.6, 25.4, 24.1, 21.1, 20.6, 16.8, 15.5, 14.7, 10.9, 9.5.

The foregoing is merely illustrative of the invention and is not intended to limit the same to the disclosed compounds and processes. Variations and changes which are obvious to one skilled in the art are intended to be within the scope and nature of the invention as defined in the claims.

What is claimed is:

1. A compound, or a salt, prodrug, or salt of a prodrug thereof, having formula (I)

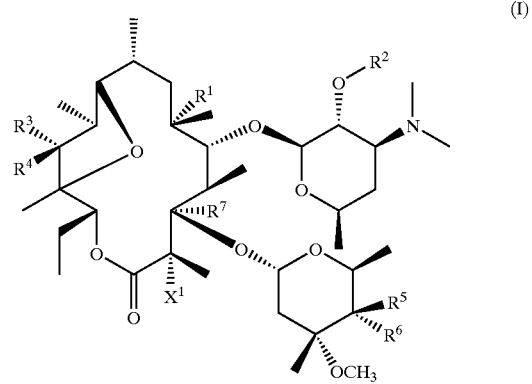

(I)

or formula (II)

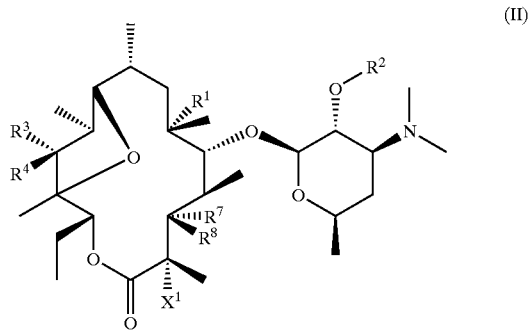

(II)

in which $R^1$ is hydrogen, —OH, —OC(O)OR$^9$, —OC(O)NH$_2$, —OC(O)NHR$^{10}$, —OC(O)NR$^{10}$R$^{11}$, —OCH$_2$R$^{12}$, —OC(O)OCH$_2$R$^{12}$, —OC(O)NHCH$_2$R$^{12}$, or —OC(O)N(CH$_2$R$^{12}$)$_2$;

$R^2$ is hydrogen or R$^P$, in which R$^P$ is a hydroxyl protecting moiety;

one of $R^3$ and $R^4$ is hydrogen, and the other is —OH, —OR$^{13}$, —OC(O)OR$^{13}$, —NH$_2$, —NHC(O)OR$^{14}$, —NHR$^{15}$, —NR$^{15}$R$^{16}$, —OC(O)NH$_2$, —OC(O)NHR$^{15}$, —OC(O)NR$^{15}$R$^{16}$, —N(R$^{17}$)C(O)NH$_2$, —N(R$^{17}$)C(O)NHR$^{15}$, —N(R$^{17}$)C(O)NR$^{15}$R$^{16}$, —OCH$_2$R$^{18}$, NHCH$_2$R$^{18}$, —N(CH$_2$R$^{18}$)$_2$, —OC(O)OCH$_2$R$^{18}$, —OC(O)NHCH$_2$R$^{18}$, —OC(O)N(CH$_2$R$^{18}$)$_2$, —N(R$^{17}$)C(O)NHCH$_2$R$^{18}$, or —N(R$^{17}$)C(O)N(CH$_2$R$^{18}$)$_2$; or $R^3$ and $R^4$ together are =O or =NOR$^{19}$;

one of $R^5$ and $R^6$ is hydrogen, and the other is —OH, —OR$^{20}$, —OC(O)OR$^{20}$, —NH$_2$, —NHC(O)OR$^{14}$, —NHR$^{21}$, —NR$^{21}$R$^{22}$, —OC(O)NH$_2$, —OC(O)NHR$^{21}$, —OC(O)NR$^{21}$R$^{22}$, —N(R$^{23}$)C(O)NH$_2$, —N(R$^{23}$)C(O)NHR$^{21}$, —N(R$^{23}$)C(O)NR$^{21}$R$^{22}$, —OCH$_2$R$^{24}$, —NHCH$_2$R$^{24}$, —N(CH$_2$R$^{24}$)$_2$, —OC(O)OCH$_2$R$^{24}$, —OC(O)NHCH$_2$R$^{24}$, —OC(O)N(CH$_2$R$^{24}$)$_2$, —N(R$^{23}$)C(O)NHCH$_2$R$^{24}$, or —N(R$^{23}$)C(O)N(CH$_2$R$^{24}$)$_2$; or R[5] and R[6] together are =O;

R[7] is hydrogen and R[8] is —OH, —OR[25], —OC(O)R[25], —OC(O)OR[25], —OC(O)NH$_2$, —OC(O)NHR[26], —OC(O)NR[26]R[27], —OCH$_2$R[28], or —OC(O)OCH$_2$R[28]; or R[7] and R[8] together are =O;

R[9], R[13], R[19], R[20], and R[25] are independently alkyl, cycloalkyl, —(CH$_2$)alkenyl, —(CH$_2$)alkynyl, alkyl substituted with one substituent selected from the group consisting of cycloalkyl, aryl, heteroaryl, and heterocyclyl, —(CH$_2$)alkenyl substituted with one substituent selected from the group consisting of cycloalkyl, aryl, heteroaryl, and heterocyclyl, or —(CH$_2$)alkynyl substituted with one substituent selected from the group consisting of cycloalkyl, aryl, heteroaryl, and heterocyclyl;

R[10], R[11], R[15], R[16], R[21], R[22], R[26], and R[27] are independently alkyl, cycloalkyl, —(CH$_2$)alkenyl, —(CH$_2$)alkynyl, aryl, heteroaryl, heterocyclyl, alkyl substituted with one substituent selected from the group consisting of cycloalkyl, aryl, heteroaryl, heterocyclyl, —NH$_2$, —NHR[31], and —NR[31]R[32], —(CH$_2$)alkenyl substituted with one substituent selected from the group consisting of cycloalkyl, aryl, heteroaryl, heterocyclyl, —NH$_2$, —NHR[31], and —NR[31]R[32], or —(CH$_2$)alkynyl substituted with one substituent selected from the group consisting of cycloalkyl, aryl, heteroaryl, heterocyclyl, —NH$_2$, —NHR[31], and —NR[31]R[32]; or R[10] and R[11] together, R[15] and R[16] together, R[21] and R[22] together, or R[26] and R[27] together are independently C$_3$–C$_6$-alkylene, C$_5$–C$_6$-alkylene interrupted with one moiety selected from the group consisting of —O—, —NH—, —N(alkyl)-, —S—, —S(O)—, and —SO$_2$—, C$_3$–C$_6$-alkylene substituted with one substituent selected from the group consisting of —OH, —O(alkyl), =O, —NH$_2$, —NH(alkyl), and —N(alkyl)$_2$, or C$_5$–C$_6$-alkylene interrupted with one moiety selected from the group consisting of —O—, —NH—, —N(alkyl)-, —S—, —S(O)—, and —SO$_2$— and substituted with one substituent selected from the group consisting of —OH, —O(alkyl), =O, —NH$_2$, —NH(alkyl), and —N(alkyl)$_2$;

R[12], R[18], R[24], and R[28] are independently alkyl interrupted with one, two, or three moieties independently selected from the group consisting of —O—, —NH—, —N(alkyl)-, —S—, —S(O)—, and —SO$_2$— or alkyl interrupted with one, two, or three moieties independently selected from the group consisting of —O—, —NH—, —N(alkyl)-, —S—, —S(O)—, and —SO$_2$— and substituted with one, two, or three substituents independently selected from the group consisting of cycloalkyl, halo, aryl, heteroaryl, heterocyclyl —OH, =O, —O(alkyl), —NH$_2$, —NH(alkyl), and —N(alkyl)$_2$;

R[14] is alkyl or alkyl substituted with one or two independently selected aryl substituents;

R[17] and R[23] are independently hydrogen or alkyl;

R[31] and R[32] are independently alkyl, cycloalkyl, aryl, heteroaryl, heterocyclyl, —(CH$_2$)alkenyl, —(CH$_2$)alkynyl, alkyl substituted with one substituent selected from the group consisting of cycloalkyl, aryl, heteroaryl, heterocyclyl, —NH$_2$, —NH(alkyl), and —N(alkyl)$_2$, —(CH$_2$)alkenyl substituted with one substituent selected from the group consisting of cycloalkyl, aryl, heteroaryl, heterocyclyl, —NH$_2$, —NH(alkyl), and —N(alkyl)$_2$, or —(CH$_2$)alkynyl substituted with one substituent selected from the group consisting of cycloalkyl, aryl, heteroaryl, heterocyclyl, —NH$_2$, —NH(alkyl), and —N(alkyl)$_2$; or R[31] and R[32] together are C$_3$–C$_6$-alkylene, C$_5$–C$_6$-alkylene interrupted with one moiety selected from the group consisting of —O—, —NH—, —N(alkyl)-, —S—, —S(O)—, and —SO$_2$—, C$_3$–C$_6$-alkylene substituted with one substituent selected from the group consisting of —OH, —O(alkyl), =O, —NH$_2$, —NH(alkyl), and —N(alkyl)$_2$, or C$_5$–C$_6$-alkylene interrupted with one moiety selected from the group consisting of —O—, —NH—, —N(alkyl)-, —S—, —S(O)—, and —SO$_2$— and substituted with one substituent selected from the group consisting of —OH, —O(alkyl), =O, —NH$_2$, —NH(alkyl), and —N(alkyl)$_2$; and X[1] is hydrogen, fluoride, chloride, or bromide.

2. The compound of claim 1, or the salt, prodrug, or salt of the prodrug thereof having the stereochemistry shown in the compound having formula (I)-f

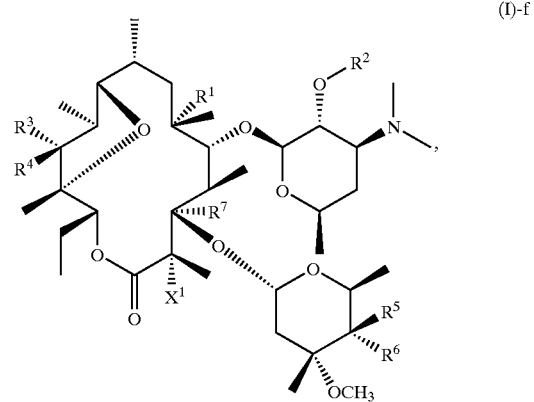

(I)-f the compound having formula (I)-g

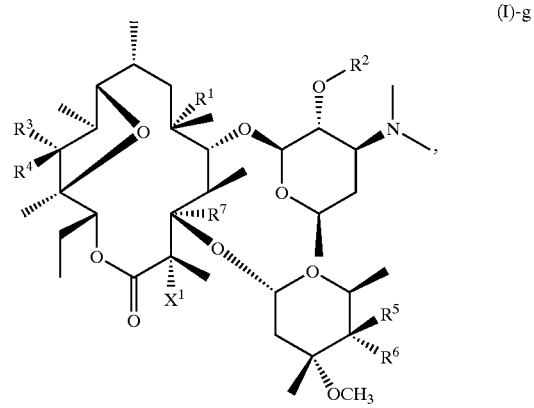

(I)-g the compound having formula (II)-f

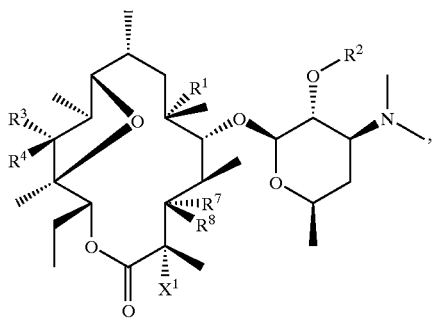

(II)-f or the compound having formula (II)-g

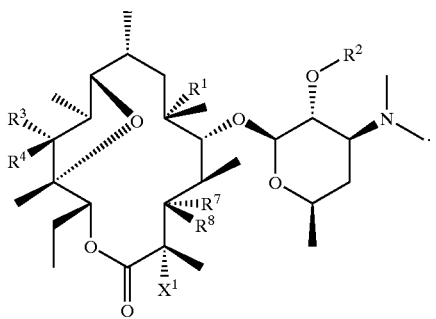

(II)-g

3. The compound of claim 1, or the salt, prodrug, or salt of the prodrug thereof, having formula (I) or formula (II), in which $R^1$ is —OH, —OC(O)OR$^9$, —OC(O)NH$_2$, —OC(O)NHR$^{10}$, or —OC(O)NR$^{10}$R$^{11}$;

$R^2$ is hydrogen or $R^P$, in which $R^P$ is a hydroxyl protecting moiety;

one of $R^3$ and $R^4$ is hydrogen, and the other is —OH, —OR$^{13}$, —OC(O)OR$^{13}$, —NH$_2$, —NHC(O)OR$^{14}$, —NHR$^{15}$, —NR$^{15}$R$^{16}$, —OC(O)NH$_2$, —OC(O)NHR$^{15}$, —OC(O)NR$^{15}$R$^{16}$, —N(R$^{17}$)C(O)NH$_2$, —N(R$^{17}$)C(O)NHR$^{15}$, or —N(R$^{17}$)C(O)NR$^{15}$R$^{16}$; or $R^3$ and $R^4$ together are =O or =NOR$^{19}$;

one of $R^5$ and $R^6$ is hydrogen, and the other is —OH, —OR$^{20}$, —OC(O)OR$^{20}$, —NH$_2$, —NHC(O)OR$^{14}$, —NHR$^{21}$, —NR$^{21}$R$^{22}$, —OC(O)NH$_2$, —OC(O)NHR$^{21}$, —OC(O)NR$^{21}$R$^{22}$, —N(R$^{23}$)C(O)NH$_2$, —N(R$^{23}$)C(O)NHR$^{21}$, or —N(R$^{23}$)C(O)NR$^{21}$R$^{22}$; or $R^5$ and $R^6$ together are =O;

$R^7$ is hydrogen and $R^8$ is —OH, —OR$^{25}$, —OC(O)R$^{25}$, —OC(O)OR$^{25}$, —OC(O)NH$_2$, —OC(O)NHR$^{26}$, or —OC(O)NR$^{26}$R$^{27}$; or $R^7$ and $R^8$ together are =O;

$R^9$, $R^{13}$, $R^{19}$, $R^{20}$, and $R^{25}$ are independently alkyl, cycloalkyl, —(CH$_2$)alkenyl, —(CH$_2$)alkynyl, alkyl substituted with one substituent selected from the group consisting of cycloalkyl, aryl, heteroaryl, and heterocyclyl, —(CH$_2$)alkenyl substituted with one substituent selected from the group consisting of cycloalkyl, aryl, heteroaryl, and heterocyclyl, or —(CH$_2$)alkynyl substituted with one substituent selected from the group consisting of cycloalkyl, aryl, heteroaryl, and heterocyclyl;

$R^{10}$, $R^{11}$, $R^{15}$, $R^{16}$, $R^{21}$, $R^{22}$, $R^{26}$, and $R^{27}$ are independently alkyl, cycloalkyl, —(CH$_2$)alkenyl, —(CH$_2$)alkynyl, aryl, heteroaryl, heterocyclyl, alkyl substituted with one substituent selected from the group consisting of cycloalkyl, aryl, heteroaryl, heterocyclyl, —NH$_2$, —NHR$^{31}$, and —NR$^{31}$R$^{32}$, —(CH$_2$)alkenyl substituted with one substituent selected from the group consisting of cycloalkyl, aryl, heteroaryl, heterocyclyl, —NH$_2$, —NHR$^{31}$, and —NR$^{31}$R$^{32}$, or —(CH$_2$)alkynyl substituted with one substituent selected from the group consisting of cycloalkyl, aryl, heteroaryl, heterocyclyl, —NH$_2$, —NHR$^{31}$, and —NR$^{31}$R$^{32}$;

$R^{14}$ is alkyl or alkyl substituted with one or two independently selected aryl substituents;

$R^{17}$ and $R^{23}$ are independently hydrogen or alkyl;

$R^{31}$ and $R^{32}$ are independently alkyl, cycloalkyl, aryl, heteroaryl, heterocyclyl, —(CH$_2$)alkenyl, —(CH$_2$)alkynyl, alkyl substituted with one substituent selected from the group consisting of cycloalkyl, aryl, heteroaryl, heterocyclyl, —NH$_2$, —NH(alkyl), and —N(alkyl)$_2$, —(CH$_2$)alkenyl substituted with one substituent selected from the group consisting of cycloalkyl, aryl, heteroaryl, heterocyclyl, —NH$_2$, —NH(alkyl), and —N(alkyl)$_2$, or —(CH$_2$)alkynyl substituted with one substituent selected from the group consisting of cycloalkyl, aryl, heteroaryl, heterocyclyl, —NH$_2$, —NH(alkyl), and —N(alkyl)$_2$; and $X^1$ is hydrogen, fluoride, chloride, or bromide.

4. The compound of claim 3, or the salt, prodrug, or salt of the prodrug thereof, having formula (I) or formula (II), in which $R^1$ is —OH or;

$R^2$ is hydrogen or $R^P$, in which $R^P$ is a hydroxyl protecting moiety;

one of $R^3$ and $R^4$ is hydrogen, and the other is —OH, —OR$^{13}$, —OC(O)OR$^{13}$, —NH$_2$, —NHC(O)OR$^{14}$, —NHR$^{15}$, —NR$^{15}$R$^{16}$, —OC(O)NH$_2$, —OC(O)NHR$^{15}$, —OC(O)NR$^{15}$R$^{16}$, —N(R$^{17}$)C(O)NH$_2$, —N(R$^{17}$)C(O)NHR$^{15}$, or —N(R$^{17}$)C(O)NR$^{15}$R$^{16}$; or $R^3$ and $R^4$ together are =O;

one of $R^5$ and $R^6$ is hydrogen, and the other is —OH, —OR$^{20}$, —OC(O)OR$^{20}$, —NH$_2$, —NHC(O)OR$^{14}$, —NHR$^{21}$, —NR$^{21}$R$^{22}$, —OC(O)NH$_2$, —OC(O)NHR$^{21}$, —OC(O)NR$^{21}$R$^{22}$, —N(R$^{23}$)C(O)NH$_2$, —N(R$^{23}$)C(O)NHR$^{21}$, or —N(R$^{23}$)C(O)NR$^{21}$R$^{22}$; or $R^5$ and $R^6$ together are =O;

$R^7$ is hydrogen and $R^8$ is —OH, —OR$^{25}$, —OC(O)R$^{25}$, —OC(O)OR$^{25}$, —OC(O)NH$_2$, —OC(O)NHR$^{26}$, or —OC(O)NR$^{26}$R$^{27}$; or $R^7$ and $R^8$ together are =O;

$R^9$, $R^{13}$, $R^{20}$, and $R^{25}$ are independently alkyl, cycloalkyl, —(CH$_2$)alkenyl, —(CH$_2$)alkynyl, alkyl substituted with one substituent selected from the group consisting of cycloalkyl, aryl, heteroaryl, and heterocyclyl, —(CH$_2$)alkenyl substituted with one substituent selected from the group consisting of cycloalkyl, aryl, heteroaryl, and heterocyclyl, or —(CH$_2$)alkynyl substituted with one substituent selected from the group consisting of cycloalkyl, aryl, heteroaryl, and heterocyclyl;

$R^{15}$, $R^{16}$, $R^{21}$, $R^{22}$, $R^{26}$, and $R^{27}$ are independently alkyl, cycloalkyl, —(CH$_2$)alkenyl, —(CH$_2$)alkynyl, aryl, heteroaryl, heterocyclyl, alkyl substituted with one substituent selected from the group consisting of cycloalkyl, aryl, heteroaryl, heterocyclyl, —NH$_2$, —NHR$^{31}$, and —NR$^{31}$R$^{32}$, —(CH$_2$)alkenyl substituted with one substituent selected from the group consisting of of cycloalkyl, aryl, heteroaryl, heterocyclyl, —NH$_2$, —NHR$^{31}$, and —NR$^{31}$R$^{32}$, or —(CH$_2$)alkynyl substituted with one substituent selected from the group consisting of cycloalkyl, aryl, heteroaryl, heterocyclyl, —NH$_2$, —NHR$^{31}$, and —NR$^{31}$R$^{32}$;

R$^{14}$ is alkyl or alkyl substituted with one or two independently selected aryl substituents;

R$^{17}$ and R$^{23}$ are independently hydrogen or alkyl;

R$^{31}$ and R$^{32}$ are independently alkyl, cycloalkyl, aryl, heteroaryl, heterocyclyl, —(CH$_2$)alkenyl, —(CH$_2$) alkynyl, alkyl substituted with one substituent selected from the group consisting of cycloalkyl, aryl, heteroaryl, heterocyclyl, —NH$_2$, —NH(alkyl), and —N(alkyl)$_2$, —(CH$_2$)alkenyl substituted with one substituent selected from the group consisting of cycloalkyl, aryl, heteroaryl, heterocyclyl, —NH$_2$, —NH(alkyl), and —N(alkyl)$_2$, or —(CH$_2$)alkynyl substituted with one substituent selected from the group consisting of cycloalkyl, aryl, heteroaryl, heterocyclyl, —NH$_2$, —NH(alkyl), and —N(alkyl)$_2$; and X$^1$ is hydrogen, fluoride, chloride, or bromide.

5. The compound of claim 4, or the salt, prodrug, or salt of the prodrug thereof, having formula (I) or formula (II), in which R$^1$ is —OH;

R$^2$ is hydrogen;

one of R$^3$ and R$^4$ is hydrogen, and the other is —OH, —OR$^{13}$, —NH$_2$, —NHC(O)OR$^{14}$, —NHR$^{15}$, —NR$^{15}$R$^{16}$OC(O)NH$_2$, —OC(O)NHR$^{15}$, or —OC(O)NR$^{15}$R$^{16}$; or R$^3$ and R$^4$ together are =O;

one of R$^5$ and R$^6$ is hydrogen, and the other is —OH, —OR$^{20}$, —OC(O)OR$^{20}$, —OC(O)NH$_2$, —OC(O)NHR$^{21}$, or —OC(O)NR$^{21}$R$^{22}$; or R$^5$ and R$^6$ together are =O;

R$^7$ is hydrogen and R$^8$ is —OH, —OR$^{25}$, —OC(O)R$^{25}$, —OC(O)OR$^{25}$, —OC(O)NH$_2$, —OC(O)NHR$^{26}$, or —OC(O)NR$^{26}$R$^{27}$; or R$^7$ and R$^8$ together are =O;

R$^9$, R$^{13}$, R$^{20}$, and R$^{25}$ are independently alkyl, —(CH$_2$) alkenyl, —(CH$_2$)alkynyl, alkyl substituted with one substituent selected from the group consisting of aryl, heteroaryl, and heterocyclyl, —(CH$_2$)alkenyl substituted with one substituent selected from the group consisting of aryl, heteroaryl, and heterocyclyl, or —(CH$_2$)alkynyl substituted with one substituent selected from the group consisting of aryl, heteroaryl, and heterocyclyl;

R$^{15}$, R$^{16}$, R$^{21}$, R$^{22}$, R$^{26}$, and R$^{27}$ are independently alkyl, cycloalkyl, —(CH$_2$)alkenyl, —(CH$_2$)alkynyl, aryl, heteroaryl, heterocyclyl, alkyl substituted with one substituent selected from the group consisting of aryl, heteroaryl, heterocyclyl, —NH$_2$, —NHR$^{31}$, and —NR$^{31}$R$^{32}$, —(CH$_2$)alkenyl substituted with one substituent selected from the group consisting of aryl, heteroaryl, heterocyclyl, —NH$_2$, —NHR$^{31}$, and —NR$^{31}$R$^{32}$, or —(CH$_2$)alkynyl substituted with one substituent selected from the group consisting of aryl, heteroaryl, heterocyclyl, —NH$_2$, —NHR$^{31}$, and —NR$^{31}$R$^{32}$;

R$^{14}$ is alkyl or alkyl substituted with phenyl;

R$^{31}$ and R$^{32}$ are independently alkyl, —(CH$_2$)alkenyl, —(CH$_2$)alkynyl, alkyl substituted with one substituent selected from the group consisting of aryl and heteroaryl, —(CH$_2$)alkenyl substituted with one substituent selected from the group consisting of aryl and heteroaryl, or —(CH$_2$)alkynyl substituted with one substituent selected from the group consisting of aryl and heteroaryl; and X$^1$ is hydrogen, fluoride, chloride, or bromide.

6. The compound of claim 5, or the salt, prodrug, or salt of the prodrug thereof, having formula (I) or formula (II), in which R$^1$ is —OH;

R$^2$ is hydrogen;

one of R$^3$ and R$^4$ is hydrogen, and the other is —OH, —NH$_2$, —NHR$^{15}$, —NR$^{15}$R$^{16}$ or —NHC(O)OR$^{14}$; or R$^3$ and R$^4$ together are =O;

R$^5$ is hydrogen, and R$^6$ is —OH, —OC(O)NH$_2$, —OC(O)NHR$^{21}$, or —OC(O)NR$^{21}$R$^{22}$;

R$^7$ is hydrogen and R$^8$ is —OH, —OR$^{25}$, —OC(O)R$^{25}$, —OC(O)NH$_2$, —OC(O)NHR$^{26}$, or —OC(O)NR$^{26}$R$^{27}$;

R$^{21}$ and R$^{22}$ are independently methyl, ethyl, propyl, butyl, prop-2-enyl, or prop-2-ynyl, each of which is independently unsubstituted or substituted with one substituent selected from the group consisting of —NH and —NHR$^{31}$;

R$^{15}$, R$^{16}$, R$^{26}$ and R$^{27}$ are independently methyl, ethyl, propyl, butyl, prop-2-enyl, prop-2-ynyl, cyclopropyl, cyclopentyl, cyclohexyl, cyclopropyl substituted with phenyl, phenyl substituted with two independently selected halo substituents, or methyl, ethyl, propyl, butyl, prop-2-enyl, or prop-2-ynyl, each of which is substituted with one substituent selected from the group consisting of (4,5-dihydroisoxazol-5-yl), phenyl, pyridyl, pyrimidinyl, thienyl, isoxazolyl, oxazolyl, quinolyl and isoquinolyl, in which substituent is unsubstituted or substituted with one substituent selected from the group consisting of —F, —Cl, —Br, methyl, —OH, (methyl)O—, phenyl, pyridyl, pyrimidinyl, thienyl and isoxazolyl;

R$^9$ and R$^{25}$ are independently methyl, ethyl, propyl, butyl, prop-2-enyl, or prop-2-ynyl, each of which is independently unsubstituted or substituted with one substituent selected from the group consisting of thienyl, isoxazolyl, 4,5-dihydroisoxazol-5-yl, phenyl, pyridyl, pyrimidinyl, quinolyl, and isoquinolyl, in which each substituent is independently unsubstituted or substituted with one substituent selected from the group consisting of phenyl, pyridyl, pyrimidinyl, thienyl, isoxazolyl, quinolyl, isoquinolyl, and phenyl substituted with one substituent selected from the group consisting of methyl, —OH, (methyl)O—, —F, —Cl, and —Br;

R$^{14}$ is tert-butyl or phenylmethyl;

R$^{31}$ is methyl, ethyl, or propyl, each of which is independently unsubstituted or substituted with one substituent selected from the group consisting of phenyl, pyridyl, quinolyl, isoquinolyl, thienyl, pyrimidinyl, isoxazolyl, and oxazolyl, in which each substituent is unsubstituted or substituted with one or two or three substituents independently selected from the group consisting of —F, —Cl, —Br, —I, methyl, —OH, and (methyl)O—; and X$^1$ is hydrogen, fluoride, chloride, or bromide.

7. The compound of claim 6, or the salt, prodrug, or salt of the prodrug thereof, having formula (I) or formula (II), in which R$^1$ is —OH;

R$^2$ is hydrogen;

R$^3$ is hydrogen; and R$^4$ is —OH, —NH$_2$, (tert-butyl)OC (O)NH—, (phenylmethyl)OC(O)NH—, (methyl) NH—, (methyl)$_2$N—, (ethyl)NH—, (propyl)NH—, (butyl) NH—, (prop-2-ynyl)NH—, (prop-2-enyl) NH—, (methyl)(phenylmethyl)N—, (3-(quinolin-3-yl)

prop-2-enyl)NH—, (3-(3-pyridin-2-ylisoxazol-5-yl)prop-2-ynyl)NH-(3-(5-(pyrimidin-2-yl)thien-2-yl)prop-2-ynyl)NH-(3-(quinolin-3-yl)propyl)NH-(3-(quinolin-3-yl)butyl)NH— or (4-(quinolin-3-yl)butyl)NH—; or $R^3$ and $R^4$ together are =O;

$R^5$ is hydrogen, and $R^6$ is (2-aminoethyl)NHC(O)O—, (2-(dimethylamino)ethyl)NHC(O)O—, (3-aminopropyl)NHC(O)O—, (4-aminobutyl)NHC(O)O—, (2-((1-(2-methoxyphenyl)ethyl)amino)ethyl)NHC(O)O—, (2-((quinolin-3-ylmethyl)amino)ethyl)NHC(O)O—, (2-((quinolin-4-ylmethyl)amino)ethyl)NHC(O)O—, or (2-((pyridin-2-ylmethyl)amino)ethyl)NHC(O)O—;

$R^7$ is hydrogen;

$R^8$ is —OH, (methyl)O—, (ethyl)O—, (propyl)O—, (prop-2-ynyl)O—, (prop-2-enyl)O—, (3-(5-(pyridin-2-yl)thien-2-yl)prop-2-ynyl)O—, (3-(quinolin-3-yl)prop-2-enyl)O—, (3-(3-(pyridin-2-yl)isoxazol-5-yl)prop-2-ynyl)O—, (3-(5-(pyrimidin-2-yl)thien-2-yl)prop-2-ynyl)O—, (3-phenyl-4,5-dihydroisoxazol-5-yl)CH$_2$O—, (3-(pyridin-2-yl)-4,5-dihydroisoxazol-5-yl)CH$_2$O—, (3-(4-fluorophenyl)-4,5-dihydroisoxazol-5-yl)CH$_2$O—, ((pyridin-2-yl)methyl)C(O)O—, (2-(pyridin-3-yl)ethyl)C(O)O—, (ethyl)NHC(O)O—, (propyl)NHC(O)O—, (isopropyl)NHC(O)O—, (3,5-dichlorophenyl)NHC(O)O—, (cyclopropyl)NHC(O)O—, (cyclopentyl)NHC(O)O—, (cyclohexyl)NHC(O)O—, (2-phenylcyclopropyl)NHC(O)O—, (phenylmethyl)NHC(O)O—, (2-fluorophenylmethyl)NHC(O)O—, (3-fluorophenylmethyl)NHC(O)O—, (4-fluorophenylmethyl)NHC(O)O—, ((4-methylphenyl)methyl)NHC(O)O—, ((4-methoxyphenyl)methyl)NHC(O)O—, ((pyridin-2-yl)methyl)NHC(O)O—, ((pyridin-3-yl)methyl)NHC(O)O—, ((pyridin-4-yl)methyl)NHC(O)O—, ((3-(phenyl)-4,5-dihydroisoxazol-5-yl)methyl)NHC(O)O—, (2-(pyridin-2-yl)ethyl)NHC(O)O—, (2-(pyridin-3-yl)ethyl)NHC(O)O—, (2-(pyridin-4-yl)ethyl)NHC(O)O—, or (quinolin-4-ylmethyl)NHC(O)O—; and $X^1$ is hydrogen, fluoride, chloride, or bromide.

8. The compound of claim 1, or the salt, prodrug, or salt of the prodrug thereof, having formula (I) in which $R^1$ is —OH; $R^2$ is hydrogen; $R^3$ is hydrogen and $R^4$ is —NH$_2$; or $R^3$ and $R^4$ together are =O; $R^5$ and $R^7$ are hydrogen; $R^6$ is —OC(O)NHR$^{21}$; $R^{21}$ is alkyl substituted with one substituent selected from the group consisting of —NH$_2$ and —NHR$^{31}$; $R^{31}$ is alkyl substituted with one substituent selected from the group consisting of phenyl and pyridyl, in which the phenyl is substituted with —O(alkyl) and the pyridyl is unfused or fused with phenyl; and $X^1$ is hydrogen.

9. The compound of claim 1, or a salt, prodrug, or salt of a prodrug thereof, having formula (I) in which $R^1$ is —OH; $R^2$ is hydrogen; $R^3$ is hydrogen and $R^4$ is —NH$_2$; or $R^3$ and $R^4$ together are =O; $R^5$ and $R^7$ are hydrogen; $R^6$ is —OC(O)NHR$^{21}$; $R^{21}$ is C$_2$-alkyl substituted with one substituent selected from the group consisting of —NH$_2$ and —NHR$^{31}$; $R^{31}$ is C$_1$–C$_2$-alkyl substituted with one substituent selected from the group consisting of phenyl and pyridyl, in which the phenyl is substituted with (methyl)O— and the pyridyl is unfused or fused with phenyl; and $X^1$ is hydrogen.

10. The compound of claim 8, or the salt, prodrug, or salt of the prodrug thereof, having formula (I), in which $R^1$ is —OH; $R^2$ is hydrogen; $R^4$ is —NH$_2$; $R^5$ and $R^7$ are hydrogen; $R^6$ is (2-((1-(2-methoxyphenyl)ethyl)amino)ethyl)NHC(O)O—, (2-aminoethyl)NHC(O)O—, (2-((quinolin-3-ylmethyl)amino)ethyl)NHC(O)O—, (2-((quinolin-4-ylmethyl)amino)ethyl)NHC(O)O—, or (2-((pyridin-2-ylmethyl)amino)ethyl)NHC(O)O—; and $X^1$ is hydrogen.

11. The compound of claim 8, or the salt, prodrug, or salt of a prodrug thereof, having formula (I), in which $R^1$ is —OH; $R^2$ is hydrogen; $R^3$ and $R^4$ together are =O; $R^5$ and $R^7$ are hydrogen; $R^6$ is (2-((1-(2-methoxyphenyl)ethyl)amino)ethyl)NHC(O)O—, (2-aminoethyl) NHC(O)O—, (2-((quinolin-3-ylmethyl)amino)ethyl)NHC(O)O—, (2-((quinolin-4-ylmethyl)amino)ethyl)NHC(O)O—, or (2-((pyridin-2-ylmethyl)amino)ethyl)NHC(O)O—; and $X^1$ is hydrogen.

12. The compound of claim 1, or the salt, prodrug, or salt of the prodrug thereof, having formula (II) in which $R^1$ is —OH; $R^2$ is hydrogen; $R^3$ and $R^7$ are hydrogen; $R^4$ is —NH$_2$ or —NHC(O)OR$^{14}$; $R^8$ is —OH, —OR$^{25}$, —OC(O)R$^{25}$, or —OC(O)NHR$^{26}$; $R^{14}$ is alkyl substituted with phenyl; $R^{25}$ is alkyl or alkyl substituted with one substituent selected from the group consisting of pyridyl and 4,5-dihydroisoxazolyl, in which the 4,5-dihydroisoxazolyl is substituted with one substituent selected from the group consisting of pyridyl and phenyl, in which the phenyl is unsubstituted or substituted with one halo substituent; $R^{26}$ is alkyl, cycloalkyl, cycloalkyl substituted with phenyl, phenyl substituted with two independently selected halo substituents, or alkyl substituted with one substituent selected from the group consisting of phenyl, pyridyl, and 4,5-dihydroisoxazolyl, in which the phenyl is unsubstituted or substituted with one substituent selected from the group consisting of alkyl, halo and —O(alkyl), and the 4,5-dihydroisoxazolyl is substituted with phenyl; and $X^1$ is hydrogen.

13. The compound of claim 1, or the salt, prodrug, or salt of the prodrug thereof, having formula (II), in which $R^1$ is —OH; $R^2$, $R^3$ and $R^7$ are hydrogen; $R^4$ is —NH$_2$ or —NHC(O)OR$^{14}$; $R^8$ is —OH, —OR$^{25}$, —OC(O)R$^{25}$, or —OC(O)NHR$^{26}$; $R^{14}$ is phenylmethyl; $R^{25}$ is C$_3$-alkyl or C$_1$–C$_2$-alkyl substituted with one substituent selected from the group consisting of pyridyl and 4,5-dihydroisoxazolyl, in which the 4,5-dihydroisoxazolyl is substituted with one substituent selected from the group consisting of pyridyl and phenyl, in which the phenyl is unsubstituted or substituted with one halo substituent; $R^{26}$ is C$_3$-alkyl, C$_5$–C$_6$-cycloalkyl, C$_3$-cycloalkyl substituted with phenyl, phenyl substituted with two independently selected halo substituents, or C$_1$–C$_2$-alkyl substituted with one substituent selected from the group consisting of phenyl, pyridyl, and 4,5-dihydroisoxazolyl, in which the phenyl is unsubstituted or substituted with one substituent selected from the group consisting of methyl, halo and (methyl)O—, and the 4,5-dihydroisoxazolyl is substituted with phenyl; and $X^1$ is hydrogen.

14. The compound of claim 12, or the salt, prodrug, or salt of the prodrug thereof, having formula (II), in which $R^1$ is —OH; $R^2$, $R^3$ and $R^7$ are hydrogen; $R^4$ is —NH$_2$; $R^8$ is —OH, (3-phenyl-4,5-dihydroisoxazol-5-yl)methoxy, (3-(pyridin-2-yl)-4,5-dihydroisoxazol-5-yl)methoxy, (3-(4-fluorophenyl)-4,5-dihydroisoxazol-5-yl)methoxy, ((pyridin-2-yl)methyl)C(O)O—, (2-(pyridin-3-yl)ethyl)C(O)O—, (propyl)NHC(O)O—, (isopropyl)NHC(O)O—, (cyclopentyl)NHC(O)O—, (cyclohexyl)NHC(O)O—, (2-phenylcyclopropyl)NHC(O)O—, (3,5-dichlorophenyl)NHC(O)O—, (phenylmethyl)NHC(O)O—, ((2-fluorophenyl)methyl)NHC(O)O—, ((3-fluorophenyl)methyl)NHC(O)O—, ((4-fluorophenyl)methyl)NHC(O)O—, ((4-methylphenyl)methyl)NHC(O)O—, ((4-methoxyphenyl)methyl)NHC(O)O—, ((pyridin-2-yl)methyl)NHC(O)O—, ((pyridin-3-yl)methyl)NHC(O)O—, ((pyridin-4-yl)methyl)NHC(O)O—, ((3-(phenyl)-4,5-dihydroisoxazol-5-yl)methyl)NHC(O)

57

O—, (2-(pyridin-2-yl)ethyl)NHC(O)O—, (2-(pyridin-3-yl)ethyl)NHC(O)O—, or (2-(pyridin-4-yl)ethyl)NHC(O)O—; and $X^1$ is hydrogen.

15. The compound of claim 12, or the salt, prodrug, or salt of the prodrug thereof, having formula (II), in which $R^1$ is —OH; $R^2$, $R^3$ and $R^7$ are hydrogen; $R^4$ is (phenylmethyl)OC(O)NH—; $R^8$ is —OH, (propyl)O—, (3-phenyl-4,5-dihydroisoxazol-5-yl)methoxy, (3-(pyridin-2-yl)-4,5-dihydroisoxazol-5-yl)methoxy, (3-(4-fluorophenyl)-4,5-dihydroisoxazol-5-yl)methoxy, ((pyridin-2-yl)methyl)C(O)O—, (2-(pyridin-3-yl)ethyl)C(O)O—, (propyl)NHC(O)O—, (isopropyl)NHC(O)O—, (cyclopentyl)NHC(O)O—, (cyclohexyl)NHC(O)O—, (2-phenylcyclopropyl)NHC(O)O—, (3,5-dichlorophenyl)NHC(O)O—, (phenylmethyl)NHC(O)O—, ((2-fluorophenyl)methyl)NHC(O)O—, ((3-fluorophenyl)methyl)NHC(O)O—, ((4-fluorophenyl)methyl)NHC(O)O—, ((4-methylphenyl)methyl)NHC(O)O—, ((4-methoxyphenyl)methyl)NHC(O)O—, ((pyridin-2-yl)methyl)NHC(O)O—, ((pyridin-3-yl)methyl)NHC(O)O—, ((pyridin-4-yl)methyl)NHC(O)O—, ((3-(phenyl)-4,5-dihydroisoxazol-5-yl)methyl)NHC(O)O—, (2-(pyridin-2-yl)ethyl)NHC(O)O—, (2-(pyridin-3-yl)ethyl)NHC(O)O—, or (2-(pyridin-4-yl)ethyl)NHC(O)O—; and $X^1$ is hydrogen.

16. A composition for treatment of bacterial infections in a fish or a mammal, the composition comprising a therapeutically effective amount of a compound of claim 1.

17. A method for treatment of bacterial infections in a fish or a mammal comprising administering to the fish or the mammal a therapeutically effective amount of a compound of claim 1.

18. The compound of claim 1, or the salt, prodrug, or salt of the prodrug thereof, which is (1-(R or S),2R,5R,6S,7S,8R,9S,11R,12S,13S)-2-ethyl-9-hydroxy-1,5,7,9,11,13-hexamethyl-4,14-dioxo-8-((3,4,6-trideoxy-3-(dimethylamino)-β-D-xylo-hexopyranosyl)oxy)-3,15-dioxabicyclo(10.2.1)pentadec-6-yl 4-O-(((2-aminoethyl)amino)carbonyl)-2,6-dideoxy-3-C-methyl-3-O-methyl-α-L-ribo-hexopyranoside;

(1-(R or S),2R,5R,6S,7S,8R,9S,11R,12S,13R,14S)-14-amino-2-ethyl-9-hydroxy-1,5,7,9,11,13-hexamethyl-4-oxo-8-((3,4,6-trideoxy-3-(dimethylamino)-β-D-xylo-hexopyranosyl)oxy)-3,15-dioxabicyclo(10.2.1) pentadec-6-yl 2,6-dideoxy-4-O-(((2-((1-(2-methoxyphenyl)ethyl)amino)ethyl)amino)carbonyl)-3-C-methyl-3-O-methyl-α-L-ribo-hexopyranoside;

(1-(R or S),2R,5R,6S,7S,8R,9S,11R,12S,13S)-2-ethyl-9-hydroxy-1,5,7,9,11,13-hexamethyl-4,14-dioxo-8-((3,4,6-trideoxy-3-(dimethylamino)-β-D-xylo-hexopyranosyl)oxy)-3,15-dioxabicyclo(10.2.1)pentadec-6-yl 2,6-dideoxy-3-C-methyl-3-O-methyl-4-O-(((2-((quinolin-3-ylmethyl)amino)ethyl)amino)carbonyl)-α-L-ribo-hexopyranoside;

(1-(R or S),2R,5R,6S,7S,8R,9S,11R,12S,13S)-2-ethyl-9-hydroxy-1,5,7,9,11,13-hexamethyl-4,14-dioxo-8-((3,4,6-trideoxy-3-(dimethylamino)-β-D-xylo-hexopyranosyl)oxy)-3,15-dioxabicyclo(10.2.1)pentadec-6-yl 2,6-dideoxy-3-C-methyl-3-O-methyl-4-O-(((2-((quinolin-4-ylmethyl)amino)ethyl)amino)carbonyl)-α-L-ribo-hexopyranoside;

(1-(R or S),2R,5R,6S,7S,8R,9S,11R,12S,13S)-2-ethyl-9-hydroxy-1,5,7,9,11,13-hexamethyl-4,14-dioxo-8-((3,4,6-trideoxy-3-(dimethylamino)-β-D-xylo-hexopyranosyl)oxy)-3,15-dioxabicyclo(10.2.1)pentadec-6-yl 2,6-dideoxy-3-C-methyl-3-O-methyl-4-O-(((2-((pyridin-2-ylmethyl)amino)ethyl)amino)carbonyl)-α-L-ribo-hexopyranoside;

58

(1-(S or R),2R,5R,6S,7S,8R,9S,11R,12S,13R,14S)-14-amino-2-ethyl-9-hydroxy-1,5,7,9,11,13-hexamethyl-4-oxo-8-((3,4,6-trideoxy-3-(dimethylamino)-β-D-xylo-hexopyranosyl)oxy)-3,15-dioxabicyclo(10.2.1) pentadec-6-yl 2,6-dideoxy-3-C-methyl-3-O-methyl-4-O-(((2-((pyridin-2-ylmethyl)amino)ethyl)amino)carbonyl)-α-L-ribo-hexopyranoside;

(1S,2R,4S,5R,6S,7S,8R,11R,12-(S or R),13S,14R)-13-amino-11-ethyl-4,7-dihydroxy-2,4,6,8,12,14-hexamethyl-9-oxo-10,15-dioxabicyclo(10.2.1)pentadec-5-yl 3,4,6-trideoxy-3-(dimethylamino)-β-D-xylo-hexopyranoside;

benzyl (1S,2R,4S,5R,6S,7S,8R,11R,12-(S or R),13S,14R)-11-ethyl-4,7-dihydroxy-2,4,6,8,12,14-hexamethyl-9-oxo-5-((3,4,6-trideoxy-3-(dimethylamino)-β-D-xylo-hexopyranosyl)oxy)-10,15-dioxabicyclo (10.2.1)pentadec-13-ylcarbamate;

(1-(S or R),2R,5R,6S,7S,8R,9S,11R,12S,13R,14S)-14-amino-2-ethyl-9-hydroxy-1,5,7,9,11,13-hexamethyl-4-oxo-8-((3,4,6-trideoxy-3-(dimethylamino)-β-D-xylo-hexopyranosyl)oxy)-3,15-dioxabicyclo(10.2.1) pentadec-6-yl isopropylcarbamate;

(1-(S or R),2R,5R,6S,7S,8R,9S,11R,12S,13R,14S)-14-amino-2-ethyl-9-hydroxy-1,5,7,9,11,13-hexamethyl-4-oxo-8-((3,4,6-trideoxy-3-(dimethylamino)-β-D-xylo-hexopyranosyl)oxy)-3,15-dioxabicyclo(10.2.1) pentadec-6-yl cyclopentylcarbamate;

(1-(S or R),2R,5R,6S,7S,8R,9S,11R,12S,13R,14S)-14-amino-2-ethyl-9-hydroxy-1,5,7,9,11,13-hexamethyl-4-oxo-8-((3,4,6-trideoxy-3-(dimethylamino)-β-D-xylo-hexopyranosyl)oxy)-3,15-dioxabicyclo(10.2.1) pentadec-6-yl cyclohexylcarbamate;

(1-(S or R),2R,5R,6S,7S,8R,9S,11R,12S,13R,14S)-14-amino-2-ethyl-9-hydroxy-1,5,7,9,11,13-hexamethyl-4-oxo-8-((3,4,6-trideoxy-3-(dimethylamino)-β-D-xylo-hexopyranosyl)oxy)-3,15-dioxabicyclo(10.2.1) pentadec-6-yl 4-fluorobenzylcarbamate;

(1-(S or R),2R,5R,6S,7S,8R,9S,11R,12S,13R,14S)-14-amino-2-ethyl-9-hydroxy-1,5,7,9,11,13-hexamethyl-4-oxo-8-((3,4,6-trideoxy-3-(dimethylamino)-β-D-xylo-hexopyranosyl)oxy)-3,15-dioxabicyclo(10.2.1) pentadec-6-yl 3,5-dichlorophenylcarbamate;

(1-(S or R),2R,5R,6S,7S,8R,9S,11R,12S,13R,14S)-14-amino-2-ethyl-9-hydroxy-1,5,7,9,11,13-hexamethyl-4-oxo-8-((3,4,6-trideoxy-3-(dimethylamino)-β-D-xylo-hexopyranosyl)oxy)-3,15-dioxabicyclo(10.2.1) pentadec-6-yl (1S,2R)-2-phenylcyclopropylcarbamate compound with (1-(S or R),2R,5R,6S,7S,8R,9S,11R,12S,13R,14S)-14-amino-2-ethyl-9-hydroxy-1,5,7,9,11,13-hexamethyl-4-oxo-8-((3,4,6-trideoxy-3-(dimethylamino)-β-D-xylo-hexopyranosyl)oxy)-3,15-dioxabicyclo(10.2.1)pentadec-6-yl (1R,2S)-2-phenylcyclopropylcarbamate (1:1);

(1-(S or R),2R,5R,6S,7S,8R,9S,11R,12S,13R,14S)-14-amino-2-ethyl-9-hydroxy-1,5,7,9,11,13-hexamethyl-4-oxo-8-((3,4,6-trideoxy-3-(dimethylamino)-β-D-xylo-hexopyranosyl)oxy)-3,15-dioxabicyclo(10.2.1) pentadec-6-yl propylcarbamate;

(1S,2R,4S,5R,6S,7S,8R,11R,12-(S or R),13S,14R)-13-amino-11-ethyl-7-((3-(4-fluorophenyl)-4,5-dihydroisoxazol-5-yl)methoxy)-4-hydroxy-2,4,6,8,12,14-hexamethyl-9-oxo-10,15-dioxabicyclo(10.2.1) pentadec-5-yl 3,4,6-trideoxy-3-(dimethylamino)-β-D-xylo-hexopyranoside (1S,2R,4S,5R,6S,7S,8R,11R,12-(S or R),13S,14R)-13-amino-11-ethyl-4-hydroxy-2,4,6,8,12,14-hexamethyl-9-oxo-7-((3-pyridin-2-yl-4,5-dihydroisoxazol-5-yl)

methoxy)-10,15-dioxabicyclo(10.2.1)pentadec-5-yl 3,4,6-trideoxy-3-(dimethylamino)-β-D-xylo-hexopyranoside;

(1-(S or R),2R,5R,6S,7S,8R,9S,11R,12S,13R,14S)-14-amino-2-ethyl-9-hydroxy-1,5,7,9,11,13-hexamethyl-4-oxo-8-((3,4,6-trideoxy-3-(dimethylamino)-β-D-xylo-hexopyranosyl)oxy)-3,15-dioxabicyclo(10.2.1)pentadec-6-yl pyridin-2-ylmethylcarbamate;

(1-(S or R),2R,5R,6S,7S,8R,9S,11R,12S,13R,14S)-14-amino-2-ethyl-9-hydroxy-1,5,7,9,11,13-hexamethyl-4-oxo-8-((3,4,6-trideoxy-3-(dimethylamino)-β-D-xylo-hexopyranosyl)oxy)-3,15-dioxabicyclo(10.2.1)pentadec-6-yl 2-pyridin-4-ylethylcarbamate;

(1S,2R,4S,5R,6S,7S,8R,11R,12-(S or R),13S,14R)-13-amino-11-ethyl-4-hydroxy-2,4,6,8,12,14-hexamethyl-9-oxo-7-propoxy-10,15-dioxabicyclo(10.2.1)pentadec-5-yl 3,4,6-trideoxy-3-(dimethylamino)-β-D-xylo-hexopyranoside;

(1S,2R,4S,5R,6S,7S,8R,11R,12-(S or R),13S,14R)-13-amino-11-ethyl-4-hydroxy-2,4,6,8,12,14-hexamethyl-9-oxo-7-((3-phenyl-4,5-dihydroisoxazol-5-yl)methoxy)-10,15-dioxabicyclo(10.2.1)pentadec-5-yl 3,4,6-trideoxy-3-(dimethylamino)-β-D-xylo-hexopyranoside;

(1-(S or R),2R,5R,6S,7S,8R,9S,11R,12S,13R,14S)-14-amino-2-ethyl-9-hydroxy-1,5,7,9,11,13-hexamethyl-4-oxo-8-((3,4,6-trideoxy-3-(dimethylamino)-β-D-xylo-hexopyranosyl)oxy)-3,15-dioxabicyclo(10.2.1)pentadec-6-yl (3-phenyl-4,5-dihydroisoxazol-5-yl)methylcarbamate;

(1-(S or R),2R,5R,6S,7S,8R,9S,11R,12S,13R,14S)-14-amino-2-ethyl-9-hydroxy-1,5,7,9,11,13-hexamethyl-4-oxo-8-((3,4,6-trideoxy-3-(dimethylamino)-β-D-xylo-hexopyranosyl)oxy)-3,15-dioxabicyclo(10.2.1)pentadec-6-yl pyridin-4-ylmethylcarbamate;

(1-(S or R),2R,5R,6S,7S,8R,9S,11R,12S,13R,14S)-14-amino-2-ethyl-9-hydroxy-1,5,7,9,11,13-hexamethyl-4-oxo-8-((3,4,6-trideoxy-3-(dimethylamino)-β-D-xylo-hexopyranosyl)oxy)-3,15-dioxabicyclo(10.2.1)pentadec-6-yl pyridin-3-ylmethylcarbamate;

(1-(S or R),2R,5R,6S,7S,8R,9S,11R,12S,13R,14S)-14-amino-2-ethyl-9-hydroxy-1,5,7,9,11,13-hexamethyl-4-oxo-8-((3,4,6-trideoxy-3-(dimethylamino)-β-D-xylo-hexopyranosyl)oxy)-3,15-dioxabicyclo(10.2.1)pentadec-6-yl pyridin-2-ylacetate;

(1-(S or R),2R,5R,6S,7S,8R,9S,11R,12S,13R,14S)-14-amino-2-ethyl-9-hydroxy-1,5,7,9,11,13-hexamethyl-4-oxo-8-((3,4,6-trideoxy-3-(dimethylamino)-β-D-xylo-hexopyranosyl)oxy)-3,15-dioxabicyclo(10.2.1)pentadec-6-yl 2-pyridin-3-ylethylcarbamate;

(1-(S or R),2R,5R,6S,7S,8R,9S,11R,12S,13R,14S)-14-amino-2-ethyl-9-hydroxy-1,5,7,9,11,13-hexamethyl-4-oxo-8-((3,4,6-trideoxy-3-(dimethylamino)-β-D-xylo-hexopyranosyl)oxy)-3,15-dioxabicyclo(10.2.1)pentadec-6-yl 2-pyridin-2-ylethylcarbamate;

(1-(S or R),2R,5R,6S,7S,8R,9S,11R,12S,13R,14S)-14-amino-2-ethyl-9-hydroxy-1,5,7,9,11,13-hexamethyl-4-oxo-8-((3,4,6-trideoxy-3-(dimethylamino)-β-D-xylo-hexopyranosyl)oxy)-3,15-dioxabicyclo(10.2.1)pentadec-6-yl 3-fluorobenzylcarbamate;

(1-(S or R),2R,5R,6S,7S,8R,9S,11R,12S,13R,14S)-14-amino-2-ethyl-9-hydroxy-1,5,7,9,11,13-hexamethyl-4-oxo-8-((3,4,6-trideoxy-3-(dimethylamino)-β-D-xylo-hexopyranosyl)oxy)-3,15-dioxabicyclo(10.2.1)pentadec-6-yl 2-fluorobenzylcarbamate;

(1-(S or R),2R,5R,6S,7S,8R,9S,11R,12S,13R,14S)-14-amino-2-ethyl-9-hydroxy-1,5,7,9,11,13-hexamethyl-4-oxo-8-((3,4,6-trideoxy-3-(dimethylamino)-β-D-xylo-hexopyranosyl)oxy)-3,15-dioxabicyclo(10.2.1)pentadec-6-yl 4-methylbenzylcarbamate;

(1-(S or R),2R,5R,6S,7S,8R,9S,11R,12S,13R,14S)-14-amino-2-ethyl-9-hydroxy-1,5,7,9,11,13-hexamethyl-4-oxo-8-((3,4,6-trideoxy-3-(dimethylamino)-β-D-xylo-hexopyranosyl)oxy)-3,15-dioxabicyclo(10.2.1)pentadec-6-yl 3-pyridin-3-ylpropanoate;

(1-(S or R),2R,5R,6S,7S,8R,9S,11R,12S,13R,14S)-14-amino-2-ethyl-9-hydroxy-1,5,7,9,11,13-hexamethyl-4-oxo-8-((3,4,6-trideoxy-3-(dimethylamino)-β-D-xylo-hexopyranosyl)oxy)-3,15-dioxabicyclo(10.2.1)pentadec-6-yl 4-methoxybenzylcarbamate; or (1-(S or R),2R,5R,6S,7S,8R,9S,11R,12S,13R,14S)-14-amino-2-ethyl-9-hydroxy-1,5,7,9,11,13-hexamethyl-4-oxo-8-((3,4,6-trideoxy-3-(dimethylamino)-β-D-xylo-hexopyranosyl)oxy)-3,15-dioxabicyclo(10.2.1)pentadec-6-yl benzylcarbamate.

* * * * *